US006835474B2

(12) United States Patent
Okada et al.

(10) Patent No.: US 6,835,474 B2
(45) Date of Patent: Dec. 28, 2004

(54) METHINE COMPOUND, MATERIAL FOR ORGANIC LUMINESCENCE ELEMENT, AND ORGANIC LUMINESCENCE ELEMENT USING THE SAME

(75) Inventors: Hisashi Okada, Ashigara (JP); Terukazu Yanagi, Ashigara (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 10/290,216

(22) Filed: Nov. 8, 2002

(65) Prior Publication Data

US 2003/0134148 A1 Jul. 17, 2003

Related U.S. Application Data

(62) Division of application No. 09/686,363, filed on Oct. 12, 2000, now Pat. No. 6,506,507, which is a division of application No. 09/271,510, filed on Mar. 18, 1999, now Pat. No. 6,458,474.

(30) Foreign Application Priority Data

| Mar. 24, 1998 | (JP) | P. 10-76339 |
| Mar. 25, 1998 | (JP) | P. 10-78167 |
| Apr. 6, 1998 | (JP) | P. 10-93665 |
| Oct. 30, 1998 | (JP) | P. 10-310945 |
| Feb. 9, 1999 | (JP) | P. 11-31718 |

(51) Int. Cl.$^7$ .............................................. H05B 33/14
(52) U.S. Cl. ................... 428/690; 428/917; 313/504; 313/506
(58) Field of Search .................. 428/690, 917; 313/504, 506; 252/301.16, 301.22, 301.26, 301.32; 546/268.1, 268.4, 268.7, 269.1, 276.4, 279.7, 281.7, 329; 549/13, 356, 414, 415, 426

(56) References Cited

U.S. PATENT DOCUMENTS

| 2,965,486 A | 10/1960 | Brooker et al. |
| 3,852,683 A | 12/1974 | Webster et al. |
| 4,145,215 A | 3/1979 | Van Allan et al. |
| 4,769,292 A | 9/1988 | Tang et al. ................. 428/690 |
| 5,281,489 A | 1/1994 | Mori et al. ................. 428/690 |
| 5,624,847 A | 4/1997 | Lakowicz et al. ............ 436/68 |
| 6,451,456 B1 * | 9/2002 | Kim et al. ................... 428/690 |

FOREIGN PATENT DOCUMENTS

| DD | 267117 A1 | 4/1989 |
| JP | 54-21722 A | 2/1979 |
| JP | 62-502548 A | 10/1987 |
| JP | 10-237117 A | 9/1998 |

OTHER PUBLICATIONS

HCAPLUS 1991:217383 (for Matsutani et al., "Laser action in new styryl dyes and their tuning characteristics", Oyo Butsuri (1990), 59(8), 1089–1092).*

MeKhimiya Geterotsiklicheskikh Soedinenii, (1974), No. 7, pp. 897–900.

C.W. Tang, S.A. VanSlyke and C.H. Chen, "Electroluminescence of doped organic thin films," *J. Appl. Phys.* 65 (9), May 1, 1989, pp. 3610–3616.

C.W. Tang and S.A. VanSlyke, "Organic Electroluminescent Diodes," *Appl. Phys. Lett.* 51 (12), Sep. 21, 1987, pp. 913–915.

T. Werner, et al, "Synthesis of . . . benzopyrans and their transformation into polymethine derivatives," *Monatshefte für Chemie*, 125, (1994), pp. 61–70. (no month).

G.A. Lindsay, et al, "Second harmonic generation from new dyes in polymers films," SPIE, vol. 2143, 1994 (no month), pp. 88–98.

* cited by examiner

*Primary Examiner*—Marie Yamnitzky
(74) *Attorney, Agent, or Firm*—Sughrue Mion, PLLC

(57) ABSTRACT

A methine compound which is represented by the following formula (VI):

(VI)

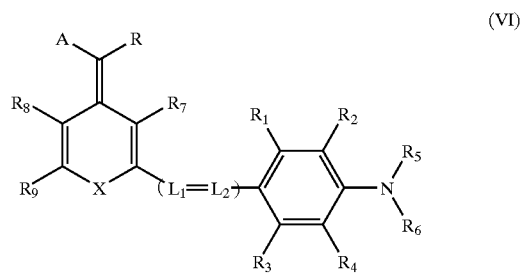

wherein $R_1$, $R_2$, $R_3$, $R_4$, $R_5$, $R_6$, $R_7$, $R_8$, $R_9$ and R each represents a hydrogen atom or a substituent; A represents a heterocyclic ring containing an aromatic ring; X represents an oxygen atom, a sulfur atom, or N—$R_{10}$, wherein $R_{10}$ represents a hydrogen atom or a substituent; $L_1$ and $L_2$ each represents a substituted or unsubstituted methine group; and n represent 1 or 2. Also, a material for organic luminescence element and organic luminescent element using the same are disclosed.

11 Claims, No Drawings

METHINE COMPOUND, MATERIAL FOR ORGANIC LUMINESCENCE ELEMENT, AND ORGANIC LUMINESCENCE ELEMENT USING THE SAME

This is a divisional of application Ser. No. 09/686,363, filed Oct. 12, 2000, now U.S. Pat. No. 6,506,507 which is a divisional of application Ser. No. 09/271,510, filed Mar. 18, 1999, now U.S. Pat. No. 6,458,474 the disclosures of which are incorporated herein by reference.

FIELD OF THE INVENTION

The present invention relates to a novel compound suitable for use as a dye for a filter, a color conversion filter, a dye for a photographic material, a sensitizing dye, a dye for pulp dyeing, a laser dye, a fluorescent medicine for a medical diagnosis, a material for an organic luminescence element, etc., and an organic luminescence element using the same.

BACKGROUND OF THE INVENTION

Prospects of an organic luminescence element in which organic materials are used are promising as a solid luminescent type inexpensive and large area full color display element and development has been tried variously. In general, an organic luminescence element comprises a luminescent layer and a pair of counter electrodes with the luminescent layer between. When electric field is impressed between both electrodes, electrons are injected from the cathode and positive holes are injected from the anode, and the electrons and positive holes are recombined in the luminescent layer. A phenomenon of emitting energy as light when energy level is returned from conduction band to valence band is luminescence.

Organic luminescence elements so far been used require high driving voltage and luminance and luminescent efficacy are low, but various techniques for improving these points are reported in recent years. For example, there is known a luminescence element comprising organic thin layers formed by vapor deposition of organic compounds (*Applied Physics Letters*, Vol. 51, p. 913 (1987)). This organic luminescence element comprises the lamination structure of an electron-transporting material and a positive hole-transporting material, and the luminescent characteristics have been remarkably improved as compared with conventionally used single layer type elements.

Al complex of 8-quinolinol (Alq) is used as a luminescent material in the above element and a luminescent color is green, but when taking into consideration the utilization as a full color display and a light source, it is necessary to get three primary colors or a white color in practical use. As the improved element thereof, an element to which a fluorescent dye is doped is reported (*Journal of Applied Physics*, Vol. 65, p. 3610 (1989)). According to the above report, reddish orange luminescence is obtained by doping 4-(dicyanomethylene)-2-methyl-6-(4-dimethylamino-styryl)-4-H-pyran (DCM), but this element is impracticable as color purity is low and durability is low. Similarly, although various organic luminescence elements which emit light in longer wavelength range than green have been developed by doping fluorescent materials, any of these elements has serious drawbacks that color purity is low as red luminescence and sufficient luminance cannot be obtained. Further, there is another problem that organic luminescence elements in which conventional red fluorescent dyes are used exhibit low durability.

Further, conventionally used elements which have excellent color purity and high luminescent efficacy are those having been doped with a small amount of a fluorescent dye in an electric charge-transporting material. Such elements have drawbacks that characteristics of elements are difficult to be reproduced from the manufacturing technique and the durability of the dye is low, as a result, the luminance is reduced or the color changes after being used for a long period of time. To cope with these problems, development of a material which functions as an electric charge-transporting material and a luminescent material in one has been desired. However, with materials so far been developed, when a fluorescent dye is used in high concentration as an electric-transporting material, emission with high luminance is difficult as quenching due to concentration occurs.

On the other hand, organic luminescence elements which have realized high luminance emission are laminated elements formed by vacuum deposition of organic materials, but from the viewpoint of simplification of producing step, processability, and realization of large area elements, it is desired to produce elements by a coating system. However, elements produced by a coating system so far been used are inferior to those produced by a vapor deposition system in luminance and luminescent efficacy, therefore, high luminance and luminescence with high efficacy have been left as problems to be solved.

Further, in recent years, various materials having fluorescence have been used in a dye for a filter, a color conversion filter, a dye for a photographic material, a sensitizing dye, a dye for pulp dyeing, a laser dye, a fluorescent medicine for a medical diagnosis, a material for an organic luminescence element, etc., and demand for such materials has been increased. However, red fluorescent dyes having high fluorescent strength and high color purity are less, therefore, the development of a novel material has been desired.

SUMMARY OF THE INVENTION

A first object of the present invention is to provide a red fluorescent compound having high color purity and to provide an organic luminescence element using the same.

A second object of the present invention is to provide a material for an organic luminescence element capable of emission of high luminance and high efficacy by low voltage-driving and excellent in stability by repeating use, and to provide an organic luminescence element using the same.

A third object of the present invention is to provide a material emitting a red color necessary to realize white luminescence and to provide an organic luminescence element using the same.

A fourth object of the present invention is to provide a material for an organic luminescence element capable of emission of high luminance and high efficacy even when produced by a coating system and to provide an organic luminescence element using the same.

A fifth object of the present invention is to provide a compound having high fluorescent strength in a reddish orange to near infrared region.

The above objects of the present invention have been achieved by the following means.

(1A) A methine compound represented by the following formula (I):

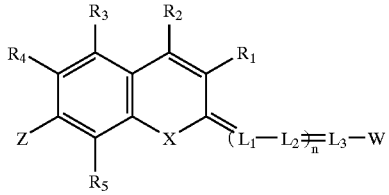

(I)

wherein $R_1$, $R_2$, $R_3$, $R_4$ and $R_5$ each represents a hydrogen atom or a substituent; X represents an oxygen atom, a sulfur atom, or N—$R_6$; Z represents —$NR_7R_8$, or —OG; $R_6$, $R_7$ and $R_8$ each represents a hydrogen atom or a substituent; G represents a hydrogen atom, a cation or a substituent; $L_1$, $L_2$ and $L_3$ each represents a substituted or unsubstituted methine group; n represents 1 or 2; and W represents an electron attractive group (electron withdrawing group).

(2A) A methine compound represented by the following formula (I-a):

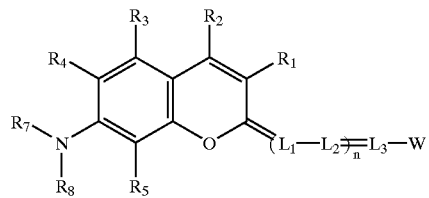

(I-a)

wherein $R_1$, $R_2$, $R_3$, $R_4$, $R_5$, $R_7$ and $R_8$ each represents a hydrogen atom or a substituent; $L_1$, $L_2$ and $L_3$ each represents a substituted or unsubstituted methine group; n represents 1 or 2; and W represents an electron attractive group.

(3A) A methine compound represented by the following formula (I-b):

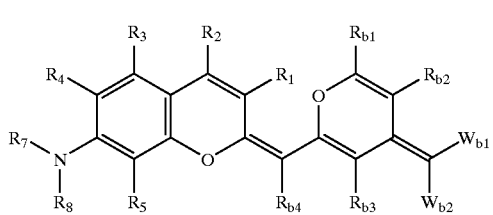

(I-b)

wherein $R_1$, $R_2$, $R_3$, $R_4$, $R_5$, $R_7$, $R_8$, $R_{b1}$, $R_{b2}$, $R_{b3}$ and $R_{b4}$ each represents a hydrogen atom or a substituent; and $W_{b1}$ and $W_{b2}$ each represents an electron attractive group.

(4A) A methine compound represented by the following formula (I-c):

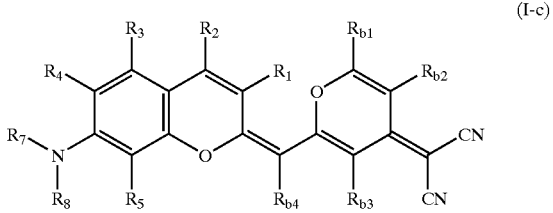

(I-c)

wherein $R_1$, $R_2$, $R_3$, $R_4$, $R_5$, $R_7$, $R_8$, $R_{b1}$, $R_{b2}$, $R_{b3}$ and $R_{b4}$ each represents a hydrogen atom or a substituent.

(5A) A methine compound represented by the following formula (I-d):

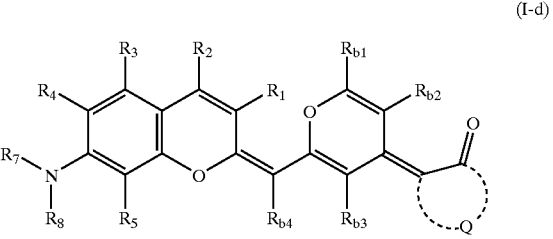

(I-d)

wherein $R_1$, $R_2$, $R_3$, $R_4$, $R_5$, $R_7$, $R_8$, $R_{b1}$, $R_{b2}$, $R_{b3}$ and $R_{b4}$ each represents a hydrogen atom or a substituent; and Q represents an atomic group necessary for forming a 5- or 6-membered ring.

(6A) A methine compound represented by the following formula (I-e):

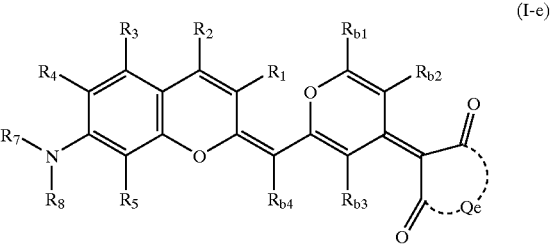

(I-e)

wherein $R_1$, $R_2$, $R_3$, $R_4$, $R_5$, $R_7$, $R_8$, $R_{1b}$, $R_{b2}$, $R_{b3}$ and $R_{b4}$ each represents a hydrogen atom or a substituent; and Qe represents an atomic group necessary for forming a 5- or 6-membered ring.

(7A) A material for an organic luminescence element which is represented by formula (I), (I-a), (I-b), (I-c), (I-d) or (I-e) as described in the above item (1A), (2A), (3A), (4A), (5A) or (6A).

(8A) An organic luminescence element comprising a pair of electrodes having formed therebetween a luminescent layer or a plurality of organic compound thin layers including a luminescent layer, wherein at least one layer is a layer containing a methine compound represented by formula (I), (I-a), (I-b), (I-c), (I-d) or (I-e) as described in the above item (1A), (2A), (3A), (4A), (5A) or (6A).

(9A) An organic luminescence element comprising a pair of electrodes having formed therebetween a luminescent layer or a plurality of organic compound thin layers including a luminescent layer, wherein at least one layer is a layer having dispersed in a polymer a methine compound represented by formula (I), (I-a), (I-b), (I-c), (I-d) or (I-e) as described in the above item (1A), (2A), (3A), (4A), (5A) or (6A).

(1B) A material for an organic luminescence element which is a compound represented by the following formula (II):

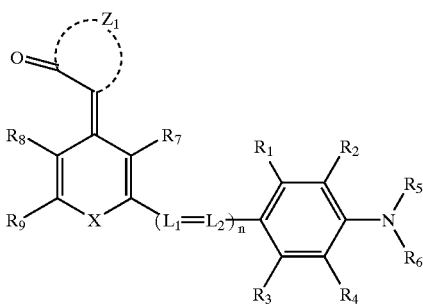

wherein $R_1$, $R_2$, $R_3$, $R_4$, $R_5$, $R_6$, $R_7$, $R_8$ and $R_9$ each represents a hydrogen atom or a substituent; X represents an oxygen atom, a sulfur atom, or N—$R_{10}$ (wherein $R_{10}$ represents a hydrogen atom or a substituent); $Z_1$ represents an atomic group necessary for forming a 5- or 6-membered ring; $L_1$ and $L_2$ each represents a substituted or unsubstituted methine group; and n represents 1 or 2.

(2B) A material for an organic luminescence element which is a compound represented by the following formula (III):

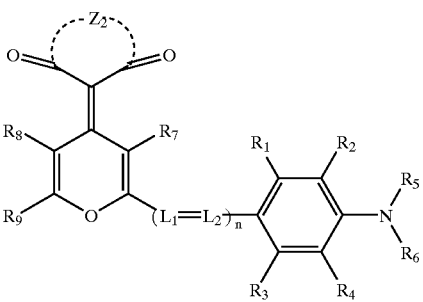

wherein $R_1$, $R_2$, $R_3$, $R_4$, $R_5$, $R_6$, $R_7$, $R_8$ and $R_9$ each represents a hydrogen atom or a substituent; $Z_2$ represents an atomic group necessary for forming a 5- or 6-membered ring; $L_1$ and $L_2$ each represents a substituted or unsubstituted methine group; and n represents 1 or 2.

(3B) A compound represented by the following formula (IV):

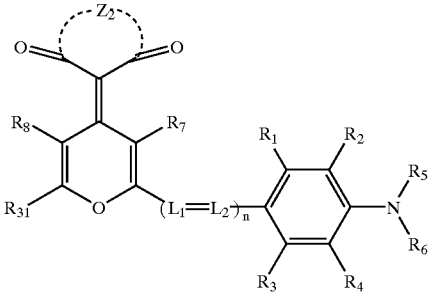

wherein $R_1$, $R_2$, $R_3$, $R_4$, $R_5$, $R_6$, $R_7$ and $R_8$ each represents a hydrogen atom or a substituent; $R_{31}$ represents an alkyl group having 2 or more carbon atoms, or an aryl group having 6 or more carbon atoms; $Z_2$ represents an atomic group necessary for forming a 5- or 6-membered ring; $L_1$ and $L_2$ each represents a substituted or unsubstituted methine group; and n represents 1 or 2.

(4B) A material for an organic luminescence element which is a compound represented by the following formula (IV):

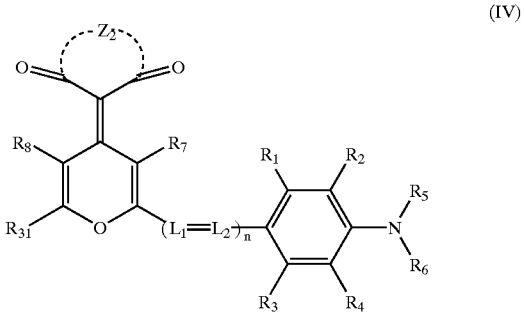

wherein $R_1$, $R_2$, $R_3$, $R_4$, $R_5$, $R_6$, $R_7$ and $R_8$ each represents a hydrogen atom or a substituent; $R_{31}$ represents an alkyl group having 2 or more carbon atoms, or an aryl group having 6 or more carbon atoms; $Z_2$ represents an atomic group necessary for forming a 5- or 6-membered ring; $L_1$ and $L_2$ each represents a substituted or unsubstituted methine group; and n represents 1 or 2.

(5B) A compound represented by the following formula (IV-a):

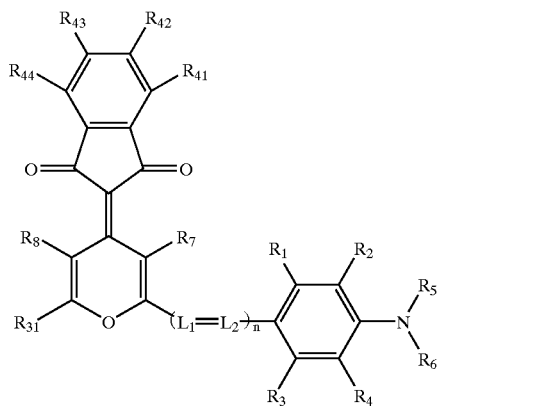

wherein $R_1$, $R_2$, $R_3$, $R_4$, $R_5$, $R_6$, $R_7$, $R_8$, $R_{41}$, $R_{42}$, $R_{43}$ and $R_{44}$ represents a hydrogen atom or a substituent; $R_{31}$ represents an alkyl group having 2 or more carbon atoms, or an aryl group having 6 or more carbon atoms; $L_1$ and $L_2$ each represents a substituted or unsubstituted methine group; and n represents 1 or 2.

(6B) A material for an organic luminescence element which is a compound represented by the following formula (IV-a):

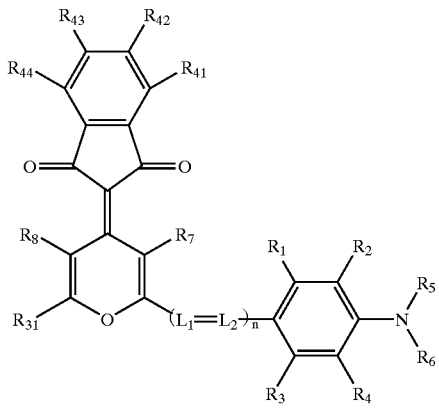

(IV-a)

wherein $R_1$, $R_2$, $R_3$, $R_4$, $R_5$, $R_6$, $R_7$, $R_8$, $R_{41}$, $R_{42}$, $R_{43}$ and $R_{44}$ each represents a hydrogen atom or a substituent; $R_{31}$ represents an alkyl group having 2 or more carbon atoms, or an aryl group having 6 or more carbon atoms; $L_1$ and $L_2$ each represents a substituted or unsubstituted methine group; and n represents 1 or 2.

(7B) A compound represented by the following formula (V):

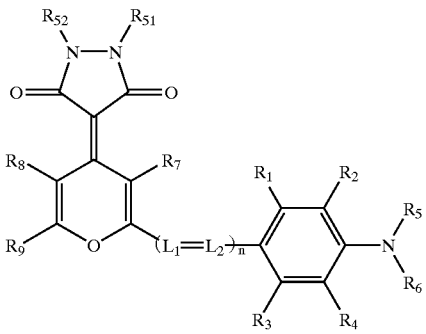

(V)

wherein $R_1$, $R_2$, $R_3$, $R_4$, $R_5$, $R_6$, $R_7$, $R_8$, $R_9$, $R_{51}$, and $R_{52}$ each represents a hydrogen atom or a substituent; $L_1$ and $L_2$ each represents a substituted or unsubstituted methine group; and n represents 1 or 2.

(8B) A material for an organic luminescence element which is a compound represented by the following formula (V):

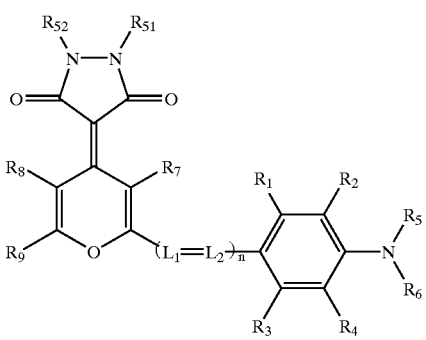

(V)

wherein $R_1$, $R_2$, $R_3$, $R_4$, $R_5$, $R_6$, $R_7$, $R_8$, $R_9$, $R_{51}$, and $R_{52}$ each represents a hydrogen atom or a substituent; $L_1$ and $L_2$ each represents a substituted or unsubstituted methine group; and n represents 1 or 2.

(9B) An organic luminescence element comprising a pair of electrodes having formed therebetween a luminescent layer or a plurality of organic compound thin layers including a luminescent layer, wherein at least one layer is a layer containing a compound represented by formula (II), (III), (IV), (IV-a) or (V) described in the above item (1B), (2B), (4B), (6B) or (8B).

(10B) An organic luminescence element comprising a pair of electrodes having formed therebetween a luminescent layer or a plurality of organic compound thin layers including a luminescent layer, wherein at least one layer is a layer having dispersed in a polymer a compound represented by formula (II), (III), (IV), (IV-a) or (V) described in the above item (1B), (2B), (4B), (6B) or (8B).

(1C) A methine compound represented by the following formula (VI):

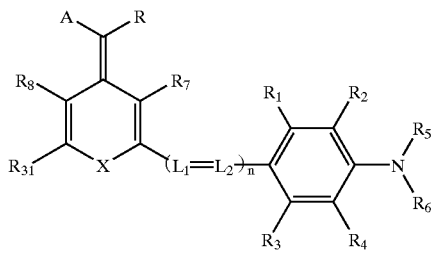

(VI)

wherein $R_1$, $R_2$, $R_3$, $R_4$, $R_5$, $R_6$, $R_7$, $R_8$, $R_9$ and R each represents a hydrogen atom or a substituent; A represents a heterocyclic ring containing an aromatic ring; X represents an oxygen atom, a sulfur atom, or N—$R_{10}$ (wherein $R_{10}$ represents a hydrogen atom or a substituent); $L_1$ and $L_2$ each represents a substituted or unsubstituted methine group; and n represents 1 or 2.

(2C) A material or an organic luminescence element represented by formula (VI) described in item (1C).

(3C) An organic luminescence element comprising a pair of electrodes having formed therebetween a luminescent layer or a plurality of organic compound thin layers including a luminescent layer, wherein at least one layer is a layer containing a methine compound described in item (1C).

(4C) An organic luminescence element comprising a pair of electrodes having formed therebetween a luminescent layer or a plurality of organic compound thin layers including a luminescent layer, wherein at least one layer is a layer having dispersed in a polymer a methine compound described in item (1C).

DETAILED DESCRIPTION OF THE INVENTION

The compound represented by formula (I) of the present invention is described in detail below.

$R_1$, $R_2$, $R_3$, $R_4$ and $R_5$ each represents a hydrogen atom or a substituent. Examples of the substituents represented by $R_1$, $R_2$, $R_3$, $R_4$ and $R_5$ include an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, 2,4,6-trimethylphenyl, naphthyl), an amino group (preferably an amino group having from 0 to 20, more preferably from 0 to 10, and particularly preferably from 0 to 6, carbon atoms, e.g., amino, methylamino, dimethylamino, diethylamino, benzylamino), an alkoxyl group (preferably an alkoxyl group having from 1 to 20, more preferably from 1 to 12, and particularly preferably from 1 to 8, carbon atoms, e.g., methoxy, ethoxy, butoxy), an aryloxy group (preferably an aryloxy group having from 6 to 20, more preferably from 6 to 16, and particularly preferably from 6 to 12, carbon atoms, e.g., phenyloxy, 2-naphthyloxy), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e.g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), an acyloxy group (preferably an acyloxy group having from 2 to 20, more preferably from 2 to 16, and particularly preferably from 2 to 10, carbon atoms, e.g., acetoxy, benzoyloxy), an acylamino group (preferably an acylamino group having from 2 to 20, more preferably from 2 to 16, and particularly preferably from 2 to 10, carbon atoms, e.g., acetylamino, benzoylamino), an alkoxycarbonylamino group (preferably an alkoxycarbonylamino group having from 2 to 20, more preferably from 2 to 16, and particularly preferably from 2 to 12, carbon atoms, e.g., methoxycarbonylamino), an aryloxycarbonylamino group (preferably an aryloxycarbonylamino group having from 7 to 20, more preferably from 7 to 16, and particularly preferably from 7 to 12, carbon atoms, e.g., phenyloxycarbonylamino), a sulfonylamino group (preferably a sulfonylamino group having from 1 to 20, more preferably from 1 to 16, and particularly preferably from 1 to 12, carbon atoms, e.g., methanesulfonylamino, benzenesulfonylamino), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenylsulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenylcarbamoyl), an alkylthio group (preferably an alkylthio group having from 1 to 20, more preferably from 1 to 16, and particularly preferably from 1 to 12, carbon atoms, e.g., methylthio, ethylthio), an arylthio group (preferably an arylthio group having from 6 to 20, more preferably from 6 to 16, and particularly preferably from 6 to 12, carbon atoms, e.g., phenylthio), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), a ureido group (preferably a ureido group having from 1 to 20, more preferably from 1 to 16, and particularly preferably from 1 to 12, carbon atoms, e.g., ureido, methylureido, phenylureido), a phosphoric acid amido group (preferably a phosphoric acid amido group having from 1 to 20, more preferably from 1 to 16, and particularly preferably from 1 to 12, carbon atoms, e.g., diethylphosphoric acid amido, phenylphosphoric acid amido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, and a heterocyclic group (preferably a heterocyclic group having from 1 to 20, and more preferably from 1 to 12, carbon atoms; as hetero atoms, e.g., nitrogen, oxygen, sulfur, and specifically, e.g., imidazolyl, pyridyl, furyl, thienyl, piperidyl, morpholino, benzoxazolyl, benzimidazolyl, benzothiazolyl can be exemplified). These substituents may further be substituted. When there are two or more substituents, they may be the same or different. Substituents may be linked together to form a ring, if possible.

Preferred examples of the substituents include an alkyl group, an alkenyl group, an aralkyl group, an aryl group, an acyl group, an alkoxycarbonyl group, an aryloxycarbonyl group, a carbonylamino group, a sulfonylamino group, a sulfamoyl group, a carbamoyl group, a cyano group, a halogen atom, a hydroxyl group, and a heterocyclic group, more preferred examples include an alkyl group, an aralkyl group, an aryl group, an acyl group, an alkoxycarbonyl group, a carbonylamino group, a sulfonylamino group, a cyano group, a halogen atom, and a heterocyclic group, and still more preferred examples include an alkyl group, an aryl group, an alkoxycarbonyl group, a cyano group, and an azole group.

$R_1$ preferably represents a hydrogen atom, an alkoxycarbonyl group, a cyano group, or an azole group, and more preferably represents a hydrogen atom.

$R_2$ preferably represents a hydrogen atom or an alkyl group, more preferably a hydrogen atom or a lower alkyl group, and particularly preferably a hydrogen atom or a methyl group.

$R_3$ preferably represents a hydrogen atom, an alkyl group, or a halogen atom, and more preferably a hydrogen atom.

$R_4$ and $R_5$ each preferably represents a hydrogen atom, an alkyl group, or an alkylene group, more preferably a hydrogen atom, a lower alkyl group (having from 1 to 4 carbon atoms), or an alkylene group, and still more preferably a hydrogen atom or an alkylene group which is formed by linking with $R_7$ or $R_8$ to form a 6-membered ring as described later.

X represents an oxygen atom, a sulfur atom, or N—$R_6$, wherein $R_6$ represents a hydrogen atom or a substituent. Examples of the substituents represented by $R_6$ include, for example, an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from2 to 8, carbon atoms, e.g., vinyl, allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, naphthyl), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e.g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenylsulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenylcarbamoyl), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), and a heterocyclic group (preferably a heterocyclic group having from 1 to 20, and more preferably from 1 to 12, carbon atoms; as hetero atoms, e.g., nitrogen, oxygen, sulfur, and specifically, e.g., imidazolyl, pyridyl, furyl, thienyl, piperidyl, morpholino, benzoxazolyl, benzimidazolyl, benzothiazolyl can be exemplified) These substituents may further be substituted. When there are two or more substituents, they may be the same or different. Substituents may be linked together to form a ring, if possible.

Preferred examples of the substituents represented by $R_6$ include an alkyl group, an alkenyl group, an alkynyl group, an aryl group, and a heterocyclic group, more preferred are an alkyl group, an aryl group, and an aromatic heterocyclic group, and still more preferred examples include an alkyl group and an aryl group.

X preferably represents an oxygen atom or N—$R_6$, and more preferably an oxygen atom.

Z represents —$NR_7R_8$, or —OG, wherein $R_7$ and $R_8$ each represents a hydrogen atom or a substituent, G represents a hydrogen atom, a cation or a substituent.

As the substituents represented by $R_7$ and $R_8$, those described in $R_6$ can be applied. $R_7$ and $R_8$ each preferably represents an alkyl group, an alkylene group, an aryl group, or a heterocyclic group, more preferably an alkyl group, an alkylene group, an aryl group, or an aromatic heterocyclic group, and still more preferably an alkyl group, an aryl group, or an alkylene group formed by linking $R_4$ with $R_7$ and $R_5$ with $R_8$ to form a 6-membered ring.

$R_7$ and $R_8$ each preferably represents a hydrogen atom, an alkyl group, an alkylene group, an aryl group, or an aromatic heterocyclic group, and more preferably a hydrogen atom, an alkyl group, an alkylene group which is formed by linking $R_4$ with $R_7$ and $R_5$ with $R_8$ to form a 6-membered ring, or an aryl group, and particularly preferably a lower alkyl group (having from 1 to 4 carbon atoms), an alkylene group formed by linking $R_4$ with $R_7$ and $R_5$ with $R_8$ to form a 6-membered ring, or an aryl group.

The cation represented by G is not particularly limited and, for example, a metal cation (e.g., a lithium ion, a sodium ion, a potassium ion, a cesium ion, a magnesium ion, a calcium ion, an aluminum ion, an europium ion), and an ammonium ion (preferably having from 0 to 30, more preferably from 0 to 20, and still more preferably from 0 to 10, carbon atoms, e.g., a tetrabutylammonium ion) can be exemplified. These metal cations may have ligands.

As the substituents represented by G, those described in $R_6$ can be cited, preferably an alkyl group (preferably an alkyl group having from 1 to 30, more preferably from 1 to 20, and still more preferably from 1 to 10, carbon atoms, e.g., methyl, ethyl, n-propyl, isopropyl, methoxyethoxymethyl), or an aryl group (preferably an aryl group having from 6 to 30, more preferably from 6 to 20, and still more preferably from 6 to 10, carbon atoms, e.g., phenyl, p-methoxyphenyl), and more preferably an alkyl group.

G preferably represents a hydrogen atom, an alkyl group, an aryl group, an alkali metal ion, an alkaline earth metal ion, an aluminum ion, a zinc ion, an europium ion, or a quaternary ammonium ion, more preferably a hydrogen atom, an alkyl group, or an aryl group, and still more preferably a hydrogen atom.

Z preferably represents —$NR_7R_8$.

$L_1$, $L_2$ and $L_3$ each represents a substituted or unsubstituted methine group. $L_1$ and $L_2$ may respectively form 4- to 6-membered rings via the substituent of the substituted methine group, or $L_1$ and $L_2$, $L_2$ and $L_3$, and $L_3$ and W may be respectively linked to each other to form 4- to 6-membered rings.

As the substituents of the substituted methine group, e.g., those exemplified as the substituents for $R_1$ to $R_5$ can be applied, preferably an alkyl group, an aryl group, an aralkyl group, an alkoxyl group, an aryloxy group, an alkylthio group, an arylthio group, a cyano group, or a halogen atom, more preferably an alkyl group or an alkoxyl group, and still more preferably a lower alkyl group (preferably having from 1 to 4 carbon atoms).

$L_1$, $L_2$ and $L_3$ each preferably represents an unsubstituted methine group, an alkyl-substituted methine group, or an alkoxyl-substituted methine group.

n represents 1 or 2, preferably 2.

W represents an electron attractive group, e.g., a cyano group, a carbonyl group, a thiocarbonyl group, an aryl group (e.g., phenyl, naphthyl), an aromatic heterocyclic group (e.g., pyridyl, quinolyl, furyl, thienyl, oxazolyl, thiazolyl, imidazolyl, oxadiazolyl, thiadiazolyl, triazolyl, benzoxazolyl, benzimidazolyl, benzothiazolyl, benzoselenazolyl, pyrimidyl), a sulfonyl group, a carbamoyl group, a sulfamoyl group can be exemplified.

Preferred examples of the electron attractive groups represented by W are a cyano group, a carbonyl group, a sulfonyl group, and an aromatic heterocyclic group, and more preferred are a cyano group and a carbonyl group.

The compound represented by formula (I) is preferably represented by formula (I-a):

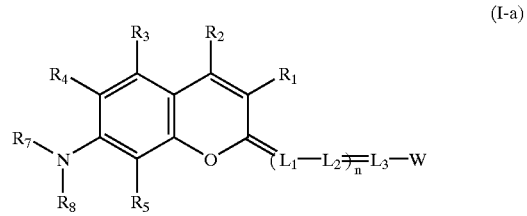

(I-a)

wherein $R_1$, $R_2$, $R_3$, $R_4$, $R_5$, $R_7$, $R_8$, $L_1$, $L_2$, $L_3$, n and W each has the same meaning as defined in formula (I), and the preferred range is also the same.

The compound represented by formula (I) is more preferably represented by formula (I-b):

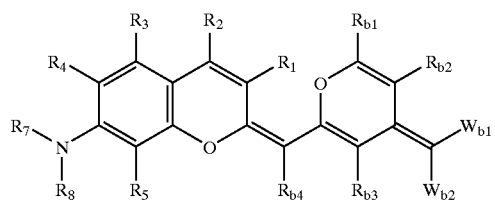

(I-b)

wherein $R_1$, $R_2$, $R_3$, $R_4$, $R_5$, $R_7$ and $R_8$ each has the same meaning as defined in formula (I), and the preferred range is also the same. $W_{b1}$ and $W_{b2}$ each has the same meaning as W in formula (I), and the preferred range is also the same. $R_{b1}$, $R_{b2}$, $R_{b3}$ and $R_{b4}$ each represents a hydrogen atom or a substituent. As the substituents represented by $R_{b1}$, $R_{b2}$, $R_{b3}$ and $R_{b4}$, e.g., those exemplified as the substituents for $R_1$ to $R_5$ in formula (I) can be applied. $R_{b1}$ preferably represents a hydrogen atom, an alkyl group, an aryl group, or a heterocyclic group, and more preferably an alkyl group (preferably an alkyl group having from 1 to 20, more preferably from 1 to 16 carbon atoms, still more preferably from 1 to 12, carbon atoms, and particularly preferably a methyl group or a tert-butyl group), or an aryl group (preferably an aryl group having from 6 to 30 carbon atoms, more preferably a phenyl group having from 6 to 30 carbon atoms and substituted with an alkyl group at the o-position, still more preferably a 2,6-dialkyl-substituted phenyl group, and particularly preferably a 2,6-dimethyl-substituted phenyl group). $R_{b1}$ particularly preferably represents a methyl group, a tert-butyl group or a 2,4,6-trimethylphenyl group, and most preferably a tert-butyl group. $R_{b2}$, $R_{b3}$ and $R_{b4}$ each preferably represents a hydrogen atom, an alkyl group, an aryl group, or a heterocyclic group, more preferably a hydrogen atom, or a lower alkyl group, and particularly preferably a hydrogen atom. $R_{b1}$ and $R_{b2}$ maybe linked to each other to form a 6-membered ring.

The compound represented by formula (I) is still more preferably represented by formula (I-c) or (I-d):

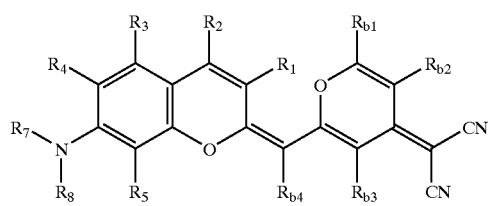

(I-c)

wherein $R_1$, $R_2$, $R_3$, $R_4$, $R_5$, $R_7$ and $R_8$ each has the same meaning as defined in formula (I), and the preferred range is also the same. $R_{b1}$, $R_{b2}$, $R_{b3}$ and $R_{b4}$ each has the same meaning as defined in formula (I-b), and the preferred range is also the same;

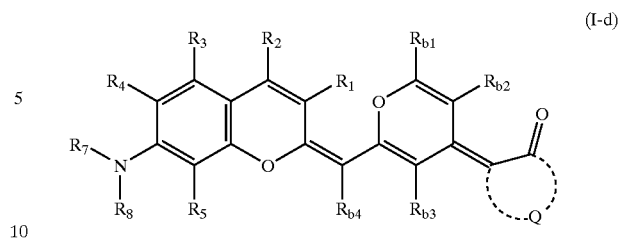

(I-d)

wherein $R_1$, $R_2$, $R_3$, $R_4$, $R_5$, $R_7$ and $R_8$ each has the same meaning as defined in formula (I), and the preferred range is also the same. $R_{b1}$, $R_{b2}$, $R_{b3}$ and $R_{b4}$ each has the same meaning as defined in formula (I-b), and the preferred range is also the same. Q represents an atomic group necessary for forming a 5- or 6-membered ring. Specific examples of the 5- or 6-membered rings formed by Q include the following:

(a) A 1,3-dicarbonyl nucleus: e.g., 1,3-cyclopentanedione, 1,3-indanedione, 1,3-cyclohexanedione, 5,5-dimethyl-1,3-cyclohexanedione, 1,3-dioxane-4,6-dione, etc.

(b) A pyrazolinone nucleus: e.g., 1-phenyl-2-pyrazolin-5-one, 3-methyl-1-phenyl-2-pyrazolin-5-one, 1-(2-benzothiazolyl)-3-methyl-2-pyrazolin-5-one, etc.

(c) An isooxazolinone nucleus: e.g., 3-phenyl-2-isooxazolin-5-one, 3-methyl-2-isooxazolin-5-one, etc.

(d) An oxyindole nucleus: e.g., 1-alkyl-2,3-dihydro-2-oxyindole, etc.

(e) A 2,4,6-triketohexahydropyrimidine nucleus: e.g., barbituric acid or 2-thiobarbituric acid and derivatives thereof, and as derivatives, e.g., 1-alkyl form such as 1-methyl, 1-ethyl; 1,3-dialkyl form such as 1,3-dimethyl, 1,3-diethyl, 1,3-dibutyl; 1,3-diaryl form such as 1,3-diphenyl, 1,3-di(p-chlorophenyl), 1,3-di(p-ethoxycarbonylphenyl); 1-alkyl-1-aryl form such as 1-ethyl-3-phenyl; and 1,3-di-heterocyclic group substitution product such as 1,3-di(2-pyridyl) can be exemplified.

(f) A 2-thio-2,4-thiazolidinedione nucleus: e.g., rhodanine and derivatives thereof, and as derivatives, e.g., 3-alkylrhodanine such as 3-methylrhodanine, 3-ethylrhodanine, 3-allylrhodanine; 3-arylrhodanine such as 3-phenylrhodanine; and 3-heterocyclic group-substituted rhodanine such as 3-(2-pyridyl)rhodanine can be exemplified.

(g) A 2-thio-2,4-oxazolidinedione (2-thio-2,4-(3H,5H)-oxazoledione) nucleus: e.g., 3-ethyl-2-thio-2,4-oxazolidinedione, etc.

(h) A thianaphthenone nucleus: e.g., 3-(2H)-thianaphthenone-1,1-dioxide, etc.

(i) A 2-thio-2,5-thiazolidinedione nucleus: e.g., 3-ethyl-2-thio-2,5-thiazolidinedione, etc.

(j) A 2,4-thiazolidinedione nucleus: e.g., 2,4-thiazolidinedione, 3-ethyl-2,4-thiazolidinedione, 3-phenyl-2,4-thiazolidinedione, etc.

(k) A thiazolin-4-one nucleus: e.g., 4-thiazolinone, 2-ethyl-4-thiazolinone, etc.

(l) A 4-thiazolidinone nucleus: e.g., 2-ethylmercapto-5-thiazolin-4-one, 2-alkylphenylamino-5-thiazolin-4-one, etc.

(m) A 2,4-imidazolidinedione (hydantoin) nucleus: e.g., 2,4-imidazolidinedione, 3-ethyl-2,4-imidazolidinedione, etc.

(n) A 2-thio-2,4-imidazolidinedione (2-thiohydantoin) nucleus: e.g., 2-thio-2,4-imidazolidinedione, 3-ethyl-2-thio-2,4-imidazolidinedione, etc.

(o) An imidazolin-5-one nucleus: e.g., 2-propylmercapto-2-imidazolin-5-one, etc.

(p) A 3,5-pyrazolidinedione nucleus: e.g., 1,2-diphenyl-3,5-pyrazolidinedione, 1,2-dimethyl-3,5-pyrazolidinedione, etc.

Preferred examples of the rings formed by Q include a 1,3-dicarbonyl nucleus, a pyrazolinone nucleus, a 2,4,6-triketohexahydropyrimidine nucleus (including a thioketone form), a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, a 2-imidazolin-5-one nucleus, and a 3,5-pyrazolidinedione nucleus, more preferred are a 1,3-dicarbonyl nucleus, a 2,4,6-triketohexahydropyrimidine nucleus (including a thioketone form), and a 3,5-pyrazolidinedione nucleus, still more preferred are a cyclic 1,3-dicarbonyl nucleus, a barbituric acid derivative, a 2-thiobarbituric acid derivative, and a 3,5-pyrazolidinedione nucleus, particularly preferred are 1,3-indanedione and 1,2-diphenyl-3,5-pyrazolidinedione, and most preferred is 1,3-indanedione.

The compound represented by formula (I-d) is more preferably represented by formula (I-e):

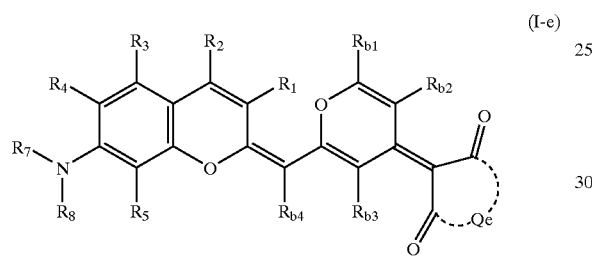

wherein $R_1$, $R_2$, $R_3$, $R_4$, $R_5$, $R_7$ and $R_8$ each has the same meaning as defined in formula (I), and the preferred range is also the same. $R_{b1}$, $R_{b2}$, $R_{b3}$ and $R_{b4}$ each has the same meaning as defined in formula (I-b), and the preferred range is also the same. Qe represents an atomic group necessary for forming a 5- or 6-membered ring. Qe represents an atomic group necessary for forming a 5- or 6-membered ring, as the 5- or 6-membered rings formed by Qe, e.g., among the rings formed by Q in formula (I-d), those having 1,3-dicarbonyl structure in the ring, e.g., 1,3-cyclopentanedione, 1,3-cyclohexanedione, and 1,3-indanedione can be exemplified, and preferred is 1,3-indanedione.

The compound represented by formula (I) may be a low molecular weight compound, may be a high molecular weight compound the polymer main chain of which is connected with the residue represented by formula (I) (preferably having a weight average molecular weight of from 1,000 to 5,000,000, more preferably from 5,000 to 2,000,000, and still more preferably from 10,000 to 1,000,000, calculated in terms of polystyrene), or may be a high molecular weight compound whose main chain has the skeleton of formula (I) (preferably having a weight average molecular weight of from 1,000 to 5,000,000, more preferably from 5,000 to 2,000,000, and still more preferably from 10,000 to 1,000,000, calculated in terms of polystyrene). The high molecular weight compound may be a homopolymer or a copolymer with other monomers.

The compound represented by formula (I) is preferably a low-molecular weight compound. Further, formula (I) is conveniently represented as an extreme structural formula but the compound may be a tautomer. When there exists a geometrical isomer, the compound may be either one.

Specific examples of the compound represented by formula (I) are shown below but the present invention is not limited thereto.

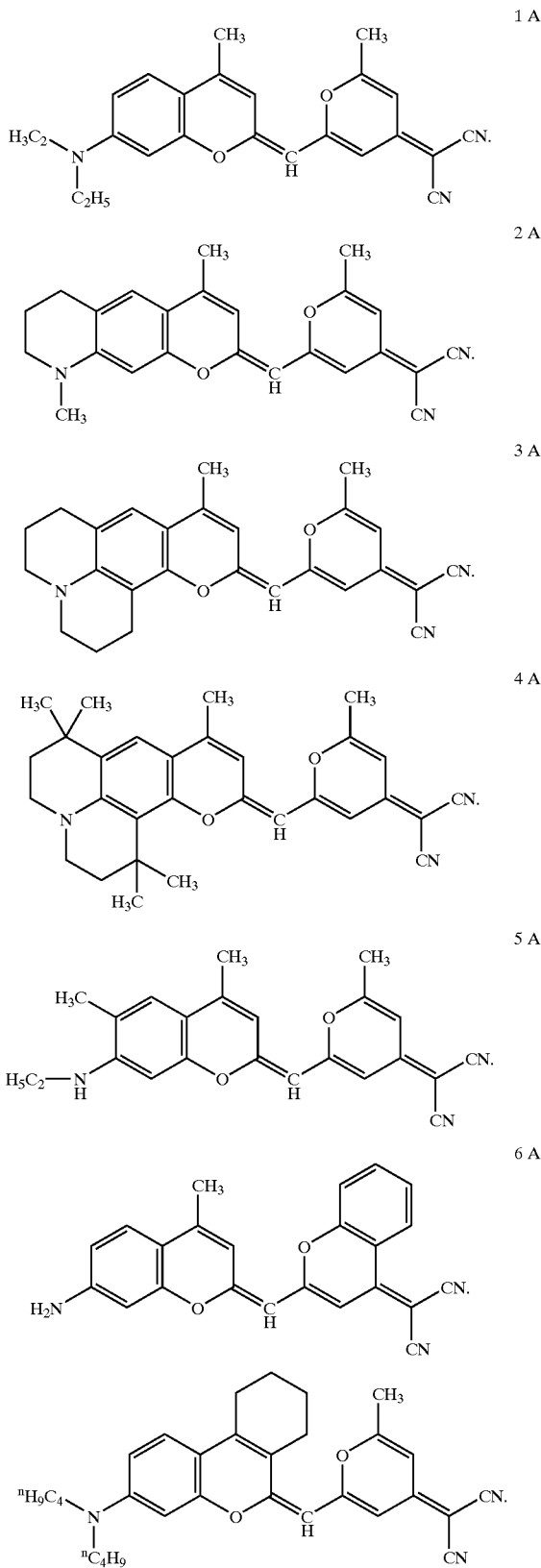

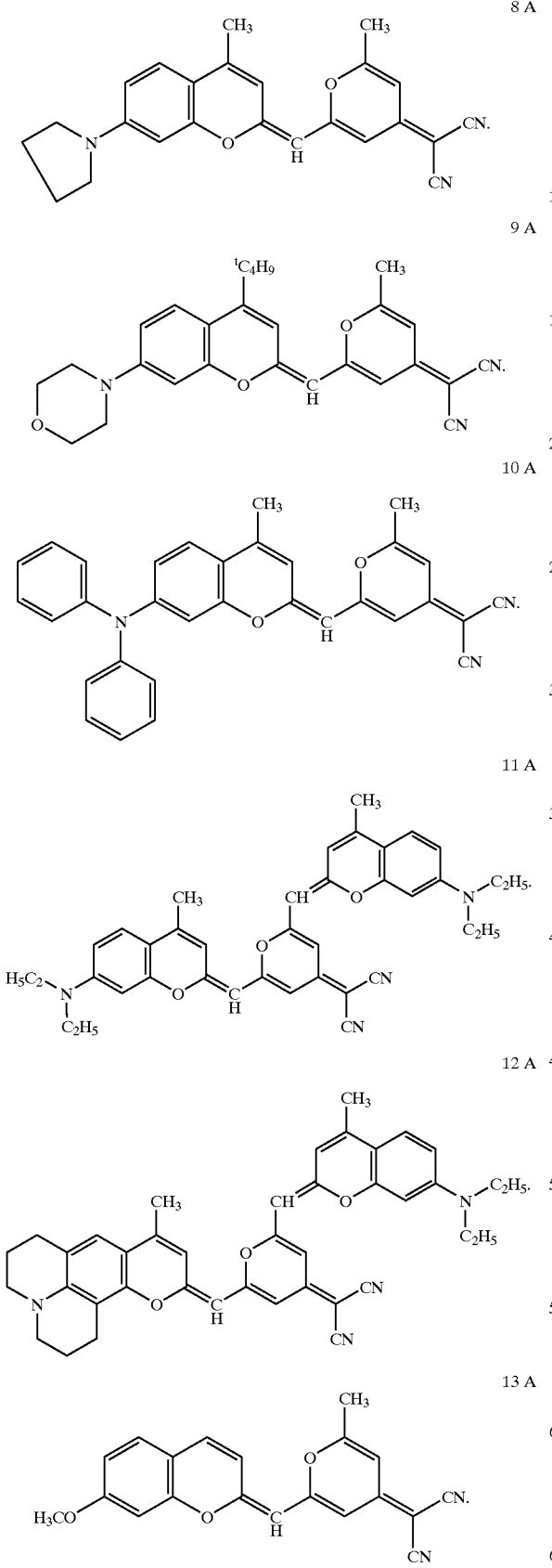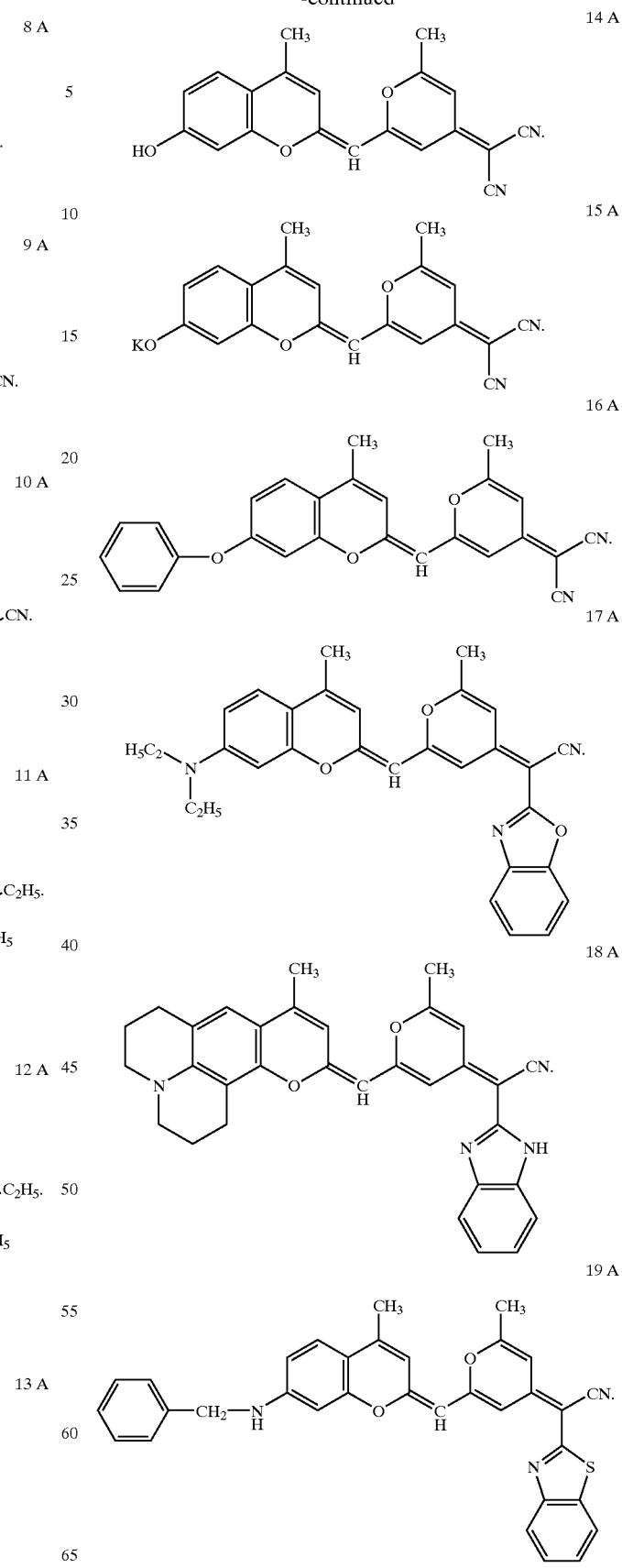

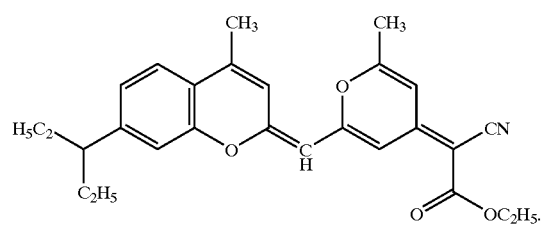
20 A
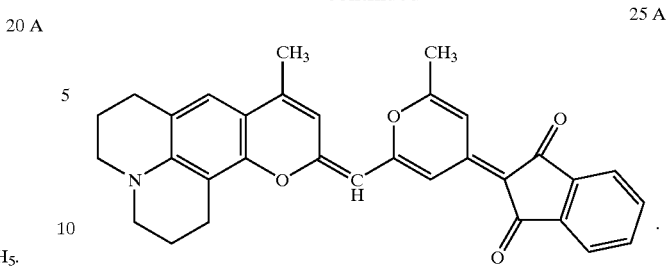
25 A
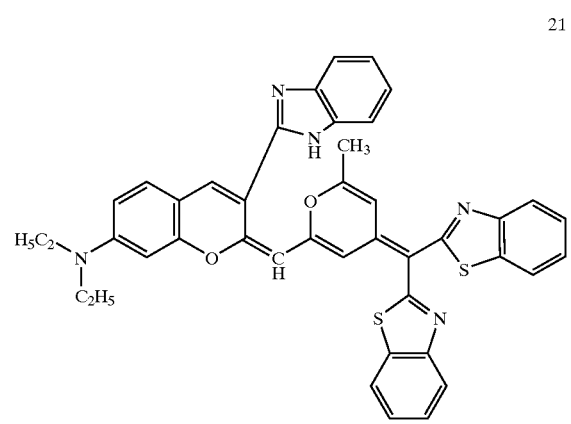
21 A
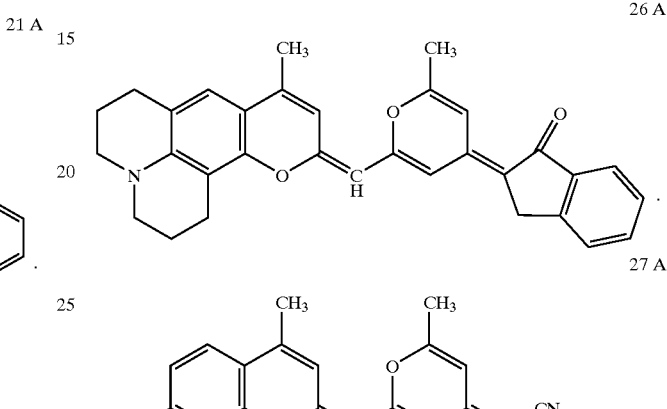
26 A
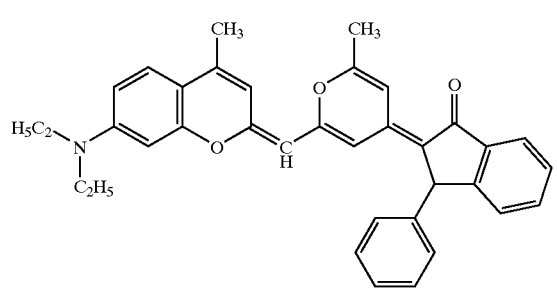
22 A
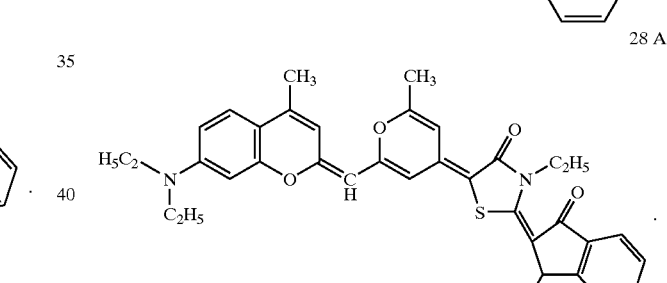
27 A
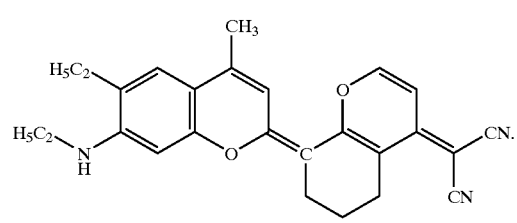
23 A
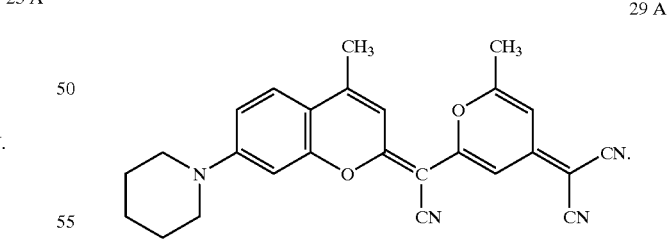
28 A
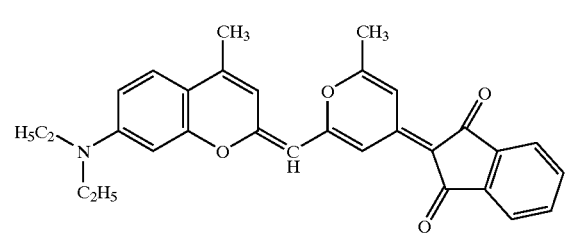
24 A
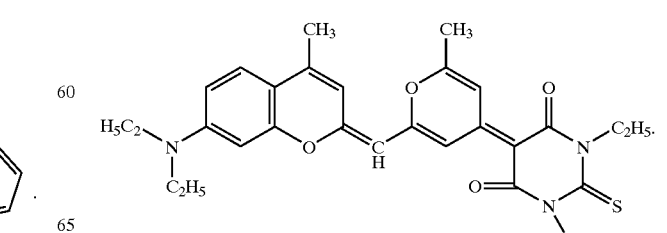
29 A
30 A 31 A
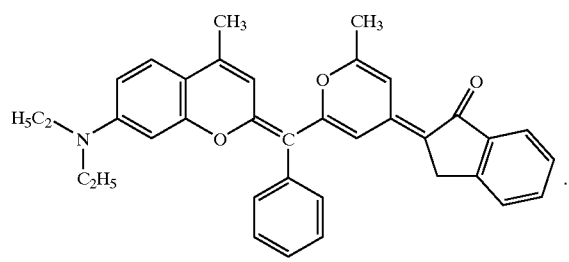
32 A
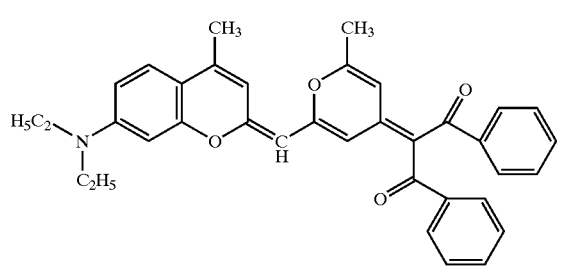
33 A
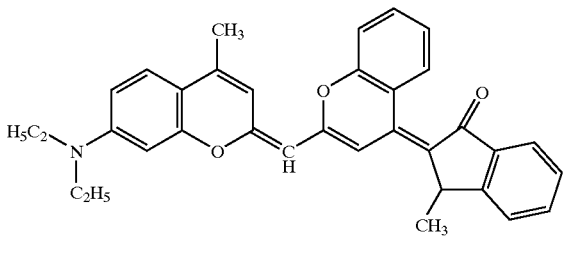
34 A
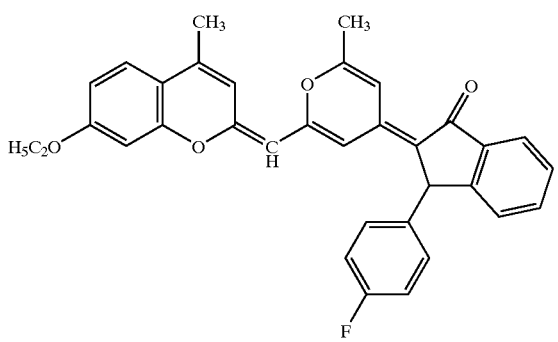
35 A
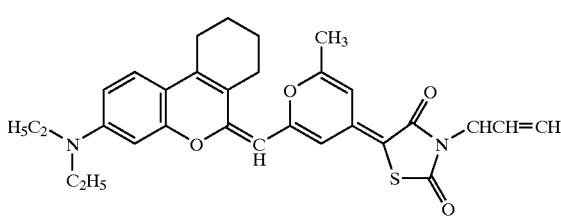
36 A
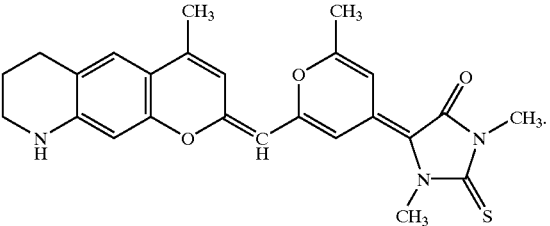
37 A
38 A
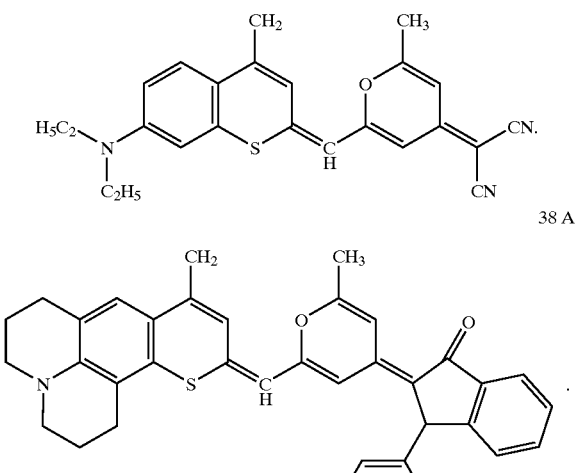
39 A
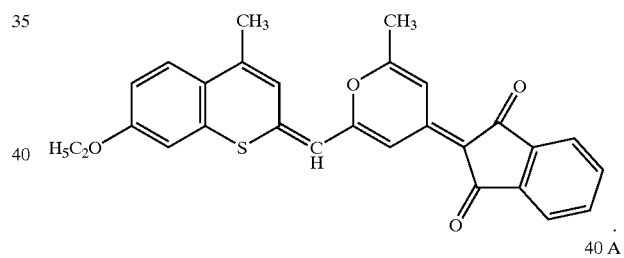
40 A
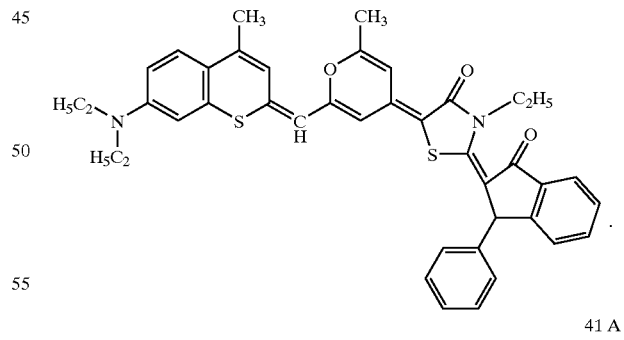
41 A
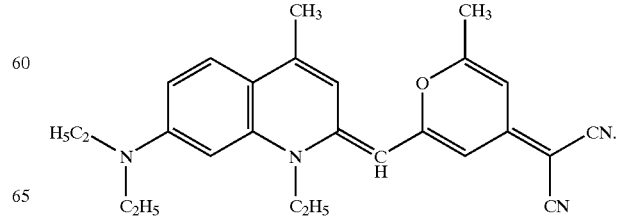

42 A
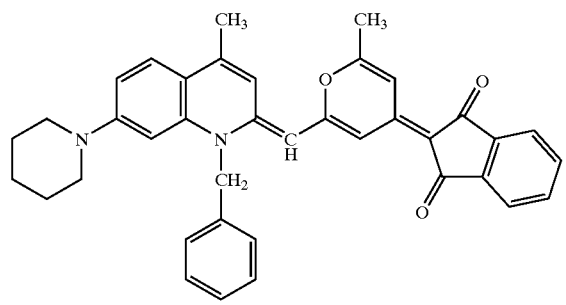
43 A
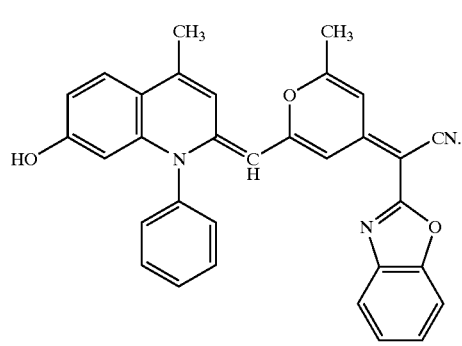
44 A
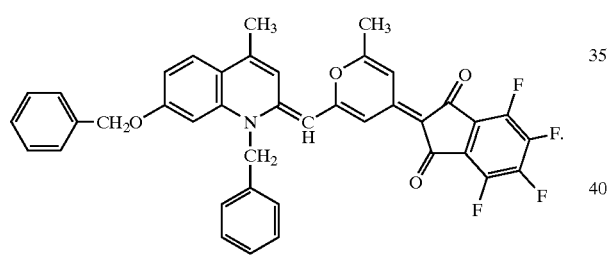
45 A
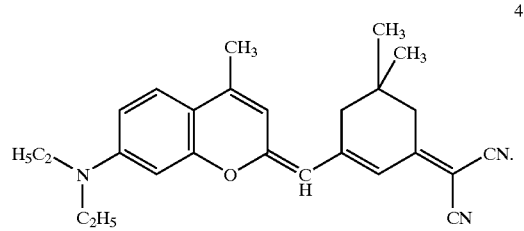
46 A
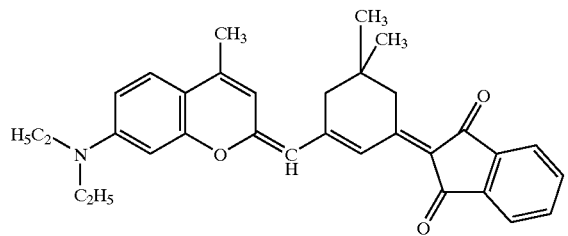
47 A
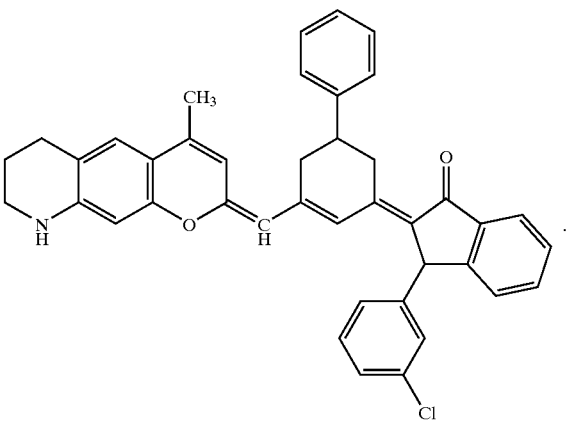
48 A
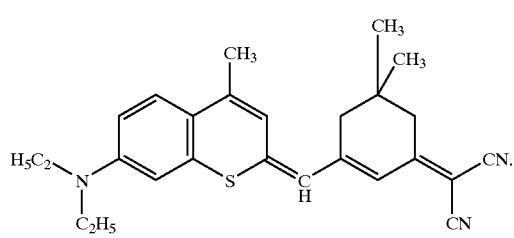
49 A
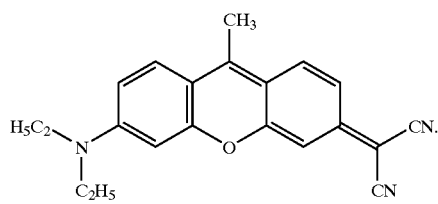
50 A
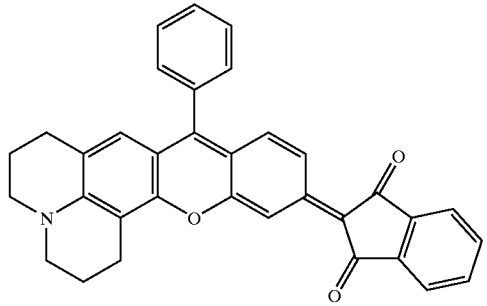
51 A
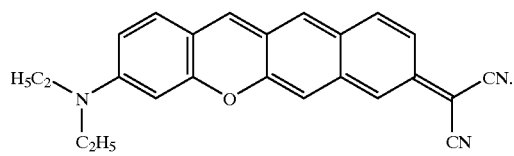

-continued
52 A
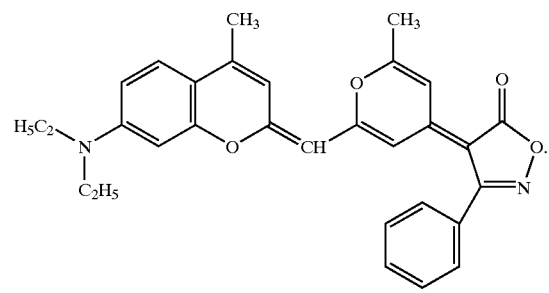
53 A
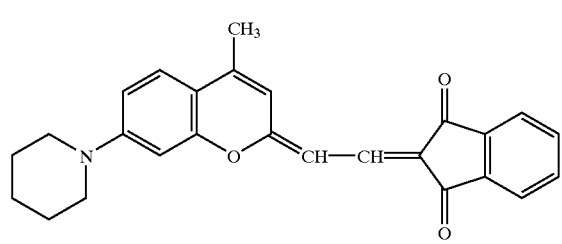
54 A
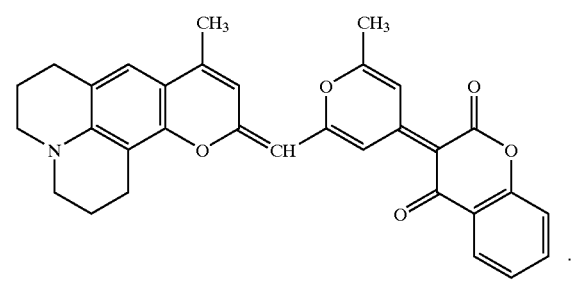
55 A
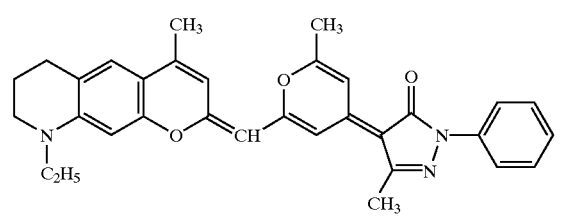
56 A
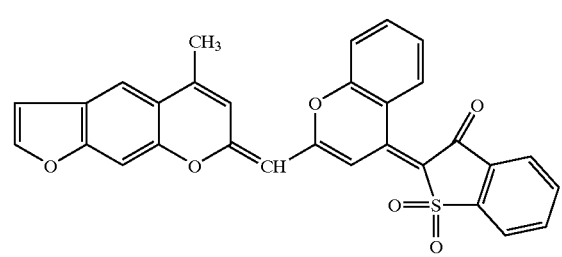
57 A
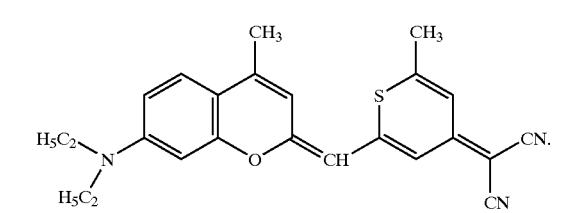
-continued
58 A
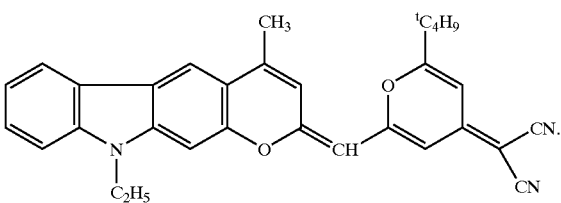
59 A
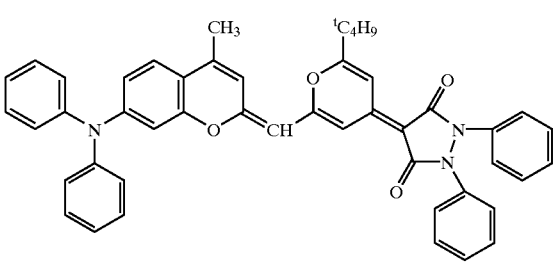
60 A
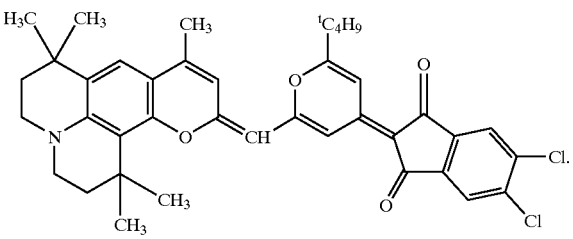
61 A
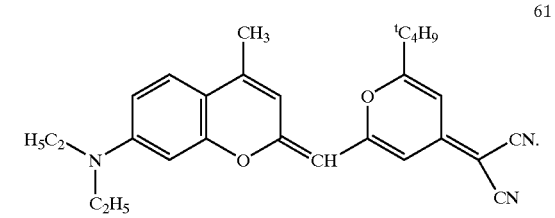
62 A
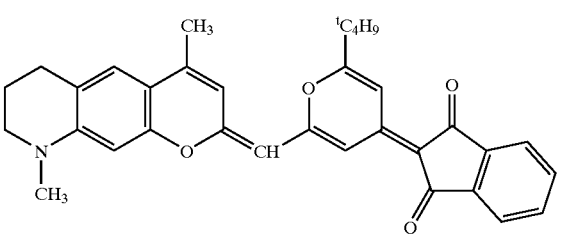
63 A
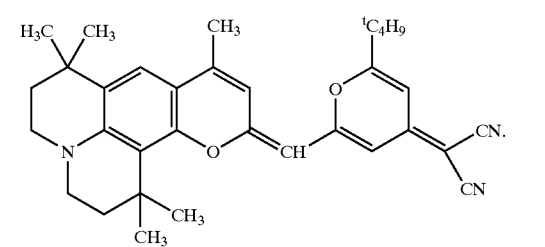

64A
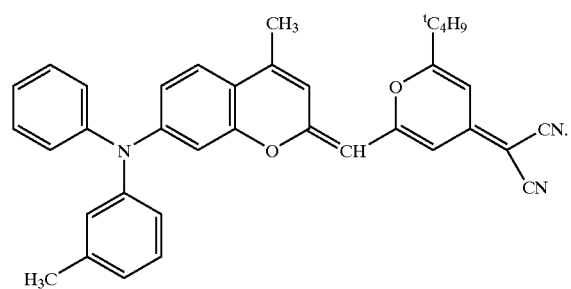
65A
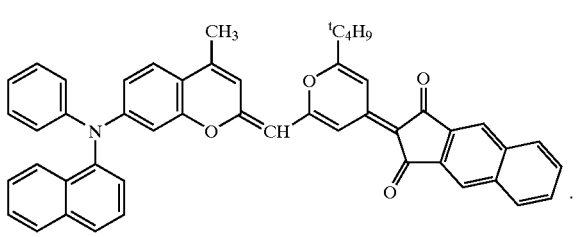
66A
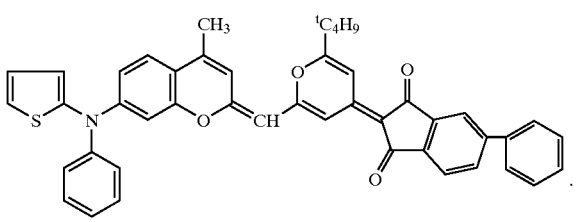
67A
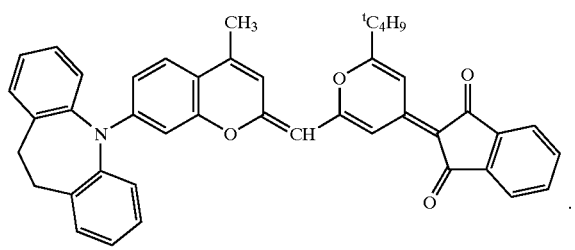
68A
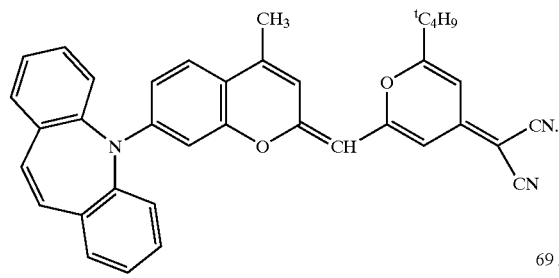
69A
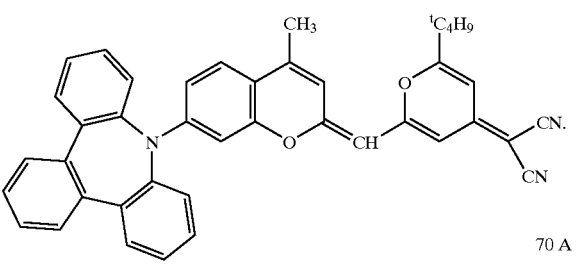
70A
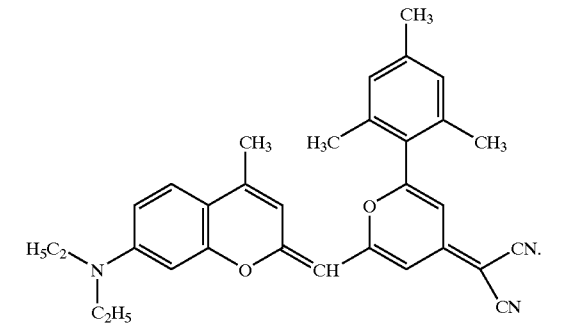
71A
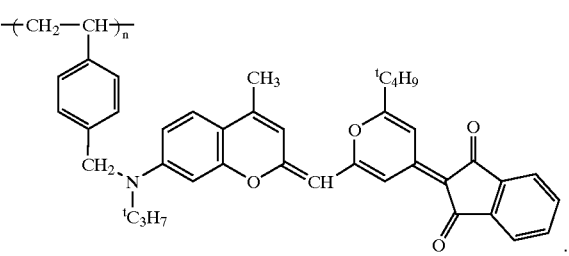
Weight average molecular weight: 13,000 (calculated in terms of polystyrene)
72A
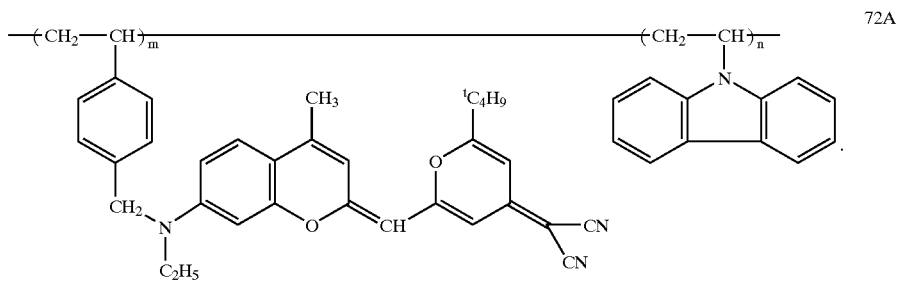

Weight average molecular weight: 11,800 (calculated in terms of polystyrene)

m/n=1/100 (by weight)

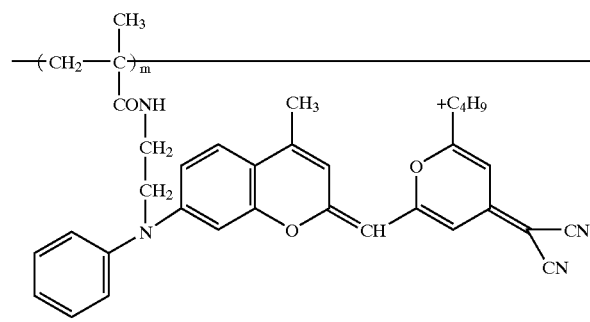

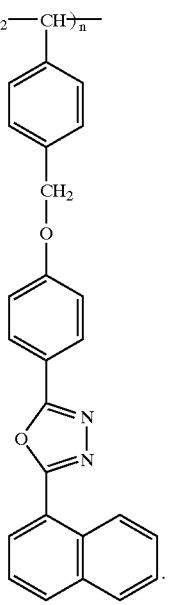

73A

Weight average molecular weight: 21,000 (calculated in terms of polystyrene)

m/n=1/98 (by weight)

The above-described compounds may be tautomers thereof.

The compound represented by formula (I) can be synthesized according to various synthesis methods. For example, a method of converting the carbonyl group of a coumarin derivative to a thiocarbonyl group and reacting it with an activated methylene compound can be applied.

The compound represented by formula (II) of the present invention is described in detail below.

$R_1$, $R_2$, $R_3$, $R_4$, $R_5$, $R_6$, $R_7$, $R_8$ and $R_9$ each represents a hydrogen atom or a substituent. Examples of the substituents represented by $R_1$, $R_2$, $R_3$, $R_4$, $R_5$, $R_6$, $R_7$, $R_8$ and $R_9$ include an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, 2,4,6-trimethylphenyl, naphthyl), an amino group (preferably an amino group having from 0 to 20, more preferably from 0 to 10, and particularly preferably from 0 to 6, carbon atoms, e.g., amino, methylamino, dimethylamino, diethylamino, benzylamino), an alkoxyl group (preferably an alkoxyl group having from 1 to 20, more preferably from 1 to 12, and particularly preferably from 1 to 8, carbon atoms, e.g., methoxy, ethoxy, butoxy), an aryloxy group (preferably an aryloxy group having from 6 to 20, more preferably from 6 to 16, and particularly preferably from 6 to 12, carbon atoms, e.g., phenyloxy, 2-naphthyloxy), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e.g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), an acyloxy group (preferably an acyloxy group having from 2 to 20, more preferably from 2 to 16, and particularly preferably from 2 to 10, carbon atoms, e.g., acetoxy, benzoyloxy), an acylamino group (preferably an acylamino group having from 2 to 20, more preferably from 2 to 16, and particularly preferably from 2 to 10, carbon atoms, e.g., acetylamino, benzoylamino), an alkoxycarbonylamino group (preferably an alkoxycarbonylamino group having from 2 to 20, more preferably from 2 to 16, and particularly preferably from 2 to 12, carbon atoms, e.g., methoxycarbonylamino), an aryloxycarbonylamino group (preferably an aryloxycarbonylamino group having from 7 to 20, more preferably from 7 to 16, and particularly preferably from 7 to 12, carbon atoms, e.g., phenyloxycarbonylamino), a sulfonylamino group (preferably a sulfonylamino group having from 1 to 20, more preferably from 1 to 16, and particularly preferably from 1 to 12, carbon atoms, e.g., methanesulfonylamino, benzenesulfonylamino), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenylsulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenylcarbamoyl), an alkylthio group (preferably an alkylthio group having from 1 to 20, more preferably from 1 to 16, and particularly preferably from 1 to 12, carbon atoms, e.g., methylthio, ethylthio), an arylthio group (preferably an arylthio group having from 6 to 20, more preferably from 6 to 16, and particularly preferably from 6 to 12, carbon atoms, e.g., phenylthio), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), a ureido group (preferably a ureido group having from 1 to 20, more preferably from 1 to 16, and particularly preferably from 1 to 12, carbon atoms, e.g., ureido, methylureido, phenylureido), a phosphoric acid amido group (preferably a phosphoric acid amido group having from 1 to 20, more preferably from 1 to 16, and particularly preferably from 1 to 12, carbon atoms, e.g., diethylphosphoric acid amido, phenylphosphoric acid amido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, and a heterocyclic group (preferably a heterocyclic group having from 1 to 20, and more preferably from 1 to 12, carbon atoms; as hetero atoms, e.g., nitrogen, oxygen, sulfur, and specifically, e.g., imidazolyl, pyridyl, furyl, piperidyl, morpholino, benzoxazolyl, benzimidazolyl, benzothiazolyl can be exemplified). These substituents may further be substituted. When there are two or more substituents, they may be the same or different. Substituents may be linked together to form a ring, if possible.

Preferred examples of the substituents include an alkyl group, an alkenyl group, an aralkyl group, an aryl group, an acyl group, an alkoxycarbonyl group, an aryloxycarbonyl group, a carbonylamino group, a sulfonylamino group, a sulfamoyl group, a carbamoyl group, a cyano group, a halogen atom, a hydroxyl group, and a heterocyclic group, more preferred examples include an alkyl group, an alkenyl group, an aralkyl group, an aryl group, an acyl group, an alkoxycarbonyl group, a carbonylamino group, a sulfonylamino group, a cyano group, a halogen atom, and a heterocyclic group, and still more preferred examples include an alkyl group, an aryl group, an alkoxycarbonyl group, a cyano group, and an azole group.

$R_1$ and $R_3$ each preferably represents a hydrogen atom, an alkyl group, an alkoxyl group, an alkoxycarbonyl group, a cyano group, or a condensed ring formed by the linkage of $R_1$ with $R_2$, or $R_3$ with $R_4$, and more preferably a methyl group or a hydrogen atom.

$R_2$ and $R_4$ each preferably represents a hydrogen atom, an alkyl group, or a condensed ring formed by the linkage of $R_2$ with $R_1$, $R_4$ with $R_3$, $R_2$ with $R_5$, or $R_4$ with $R_6$, more preferably a hydrogen atom, a methyl group, or a condensed ring formed by the linkage of $R_2$ with $R_5$, or $R_4$ with $R_6$, and still more preferably a hydrogen atom or a 6-membered ring formed by the linkage of $R_2$ with $R_5$, or $R_4$ with $R_6$, via an alkylene group.

$R_5$ and $R_6$ each preferably represents a hydrogen atom, an alkyl group, an alkylene group, or an aryl group, more preferably an alkyl group, an alkylene group, or an aryl group, still more preferably a methyl group, an ethyl group, or a 6-membered ring formed by the linkage of $R_5$ with $R_2$, or $R_6$ with $R_4$, via an alkylene group, and particularly preferably a methyl group or a 6-membered ring formed by the linkage of $R_5$ with $R_2$, or $R_6$ with $R_4$, via an alkylene group.

$R_7$ preferably represents a hydrogen atom, an alkyl group, an aryl group, a halogen atom, or a cyano group, more preferably a hydrogen atom or an alkyl group, and still more preferably a hydrogen atom.

$R_8$ preferably represents a hydrogen atom, an alkyl group, an aryl group, a halogen atom, a cyano group, or a ring formed by linking with $R_9$, more preferably a hydrogen atom or an alkyl group, and still more preferably a hydrogen atom.

$R_9$ preferably represents a hydrogen atom, an alkyl group, an aryl group, a ring formed by linking with $R_8$, or

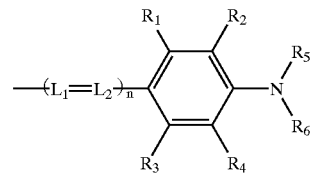

(wherein $R_1$, $R_2$, $R_3$, $R_4$, $R_5$, $R_6$, $L_1$, $L_2$, and n each has the same meaning as in formula (II)), more preferably an alkyl group (preferably an alkyl group having from 2 to 20 carbon atoms, more preferably a branched or cyclic alkyl group having from 3 to 20 carbon atoms, still more preferably a branched or cyclic alkyl group having from 4 to 12 quaternary carbon atoms, and particularly preferably a tert-butyl group), an aryl group (preferably an aryl group having from 6 to 30 carbon atoms and substituted at the opposition, more preferably a phenyl group having from 6 to 30 carbon atoms and substituted with an alkyl group at the o-position, and still more preferably a 2,6-dimethyl-substituted phenyl group), or

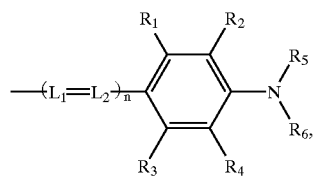

still more preferably an alkyl group (preferably an alkyl group having from 2 to 20 carbon atoms, more preferably a branched alkyl group having from 3 to 20 carbon atoms, still more preferably a branched alkyl group having from 4 to 12 quaternary carbon atoms, and particularly preferably a tert-butyl group), an aryl group (preferably an aryl group having from 6 to 30 carbon atoms and substituted at the o-position, more preferably a phenyl group having from 6 to 30 carbon atoms and substituted with an alkyl group at the o-position, still more preferably a 2,6-dimethyl-substituted phenyl group, and particularly preferably a 2,4,6-trimethylphenyl group), and $R_9$ particularly preferably represents a tert-butyl group or a 2,4,6-trimethylphenyl group, and most preferably a tert-butyl group.

X represents an oxygen atom, a sulfur atom, or N—$R_{10}$, wherein $R_{10}$ represents a hydrogen atom or a substituent. Examples of the substituents represented by $R_{10}$ include, for example, an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl, allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, naphthyl), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e.g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenylsulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenylcarbamoyl), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), and a heterocyclic group (preferably a heterocyclic group having from 1 to 20, and more preferably from 1 to 12, carbon atoms; as hetero atoms, e.g., nitrogen, oxygen, sulfur, and specifically, e.g., imidazolyl, pyridyl, furyl, piperidyl, morpholino, benzoxazolyl, benzimidazolyl, benzothiazolyl can be exemplified). These substituents may further be substituted. When there are two or more substituents, they may be the same or different. Substituents may be linked together to form a ring, if possible.

Preferred examples of the substituents represented by $R_{10}$ include an alkyl group, an alkenyl group, an alkynyl group, an aryl group, and a heterocyclic group, more preferred are an alkyl group, an aryl group, and an aromatic heterocyclic group, and still more preferred examples are an alkyl group and an aryl group.

X preferably represents an oxygen atom or N—$R_{10}$, and more preferably an oxygen atom.

$Z_1$ represents an atomic group necessary for forming a 5- or 6-membered ring. Specific examples of the 5- or 6-membered rings formed by $Z_1$ include the following:

(a) A 1,3-dicarbonyl nucleus: e.g., 1,3-cyclopentanedione, 1,3-indanedione, 1,3-cyclohexanedione, 5,5-dimethyl-1,3-cyclohexanedione, 1,3-dioxane-4,6-dione, etc.

(b) A pyrazolinone nucleus: e.g., 1-phenyl-2-pyrazolin-5-one, 3-methyl-1-phenyl-2-pyrazolin-5-one, 1-(2-benzothiazolyl)-3-methyl-2-pyrazolin-5-one, etc.

(c) An isooxazolinone nucleus: e.g., 3-phenyl-2-isooxazolin-5-one, 3-methyl-2-isooxazolin-5-one, etc.

(d) An oxyindole nucleus: e.g., 1-alkyl-2,3-dihydro-2-oxyindole, etc.

(e) A 2,4,6-triketohexahydropyrimidine nucleus: e.g., barbituric acid or 2-thiobarbituric acid and derivatives thereof, and as derivatives, e.g., 1-alkyl form such as 1-methyl, 1-ethyl; 1,3-dialkyl form such as 1,3-dimethyl, 1,3-diethyl, 1,3-dibutyl; 1,3-diaryl form such as 1,3-diphenyl, 1,3-di(p-chlorophenyl), 1,3-di(p-ethoxycarbonylphenyl); 1-alkyl-1-aryl form such as 1-ethyl-3-phenyl; and 1,3-diheterocyclic ring substitution product such as 1,3-di(2-pyridyl) can be exemplified.

(f) A 2-thio-2,4-thiazolidinedione nucleus: e.g., rhodanine and derivatives thereof, and as derivatives, e.g., 3-alkylrhodanine such as 3-methylrhodanine, 3-ethylrhodanine, 3-allylrhodanine; 3-arylrhodanine such as 3-phenylrhodanine; and 3-heterocyclic ring substituted rhodanine such as 3-(2-pyridyl)rhodanine can be exemplified.

(g) A 2-thio-2,4-oxazolidinedione (2-thio-2,4-(3H,5H)-oxazoledione) nucleus: e.g., 3-ethyl-2-thio-2,4-oxazolidinedione, etc.

(h) A thianaphthenone nucleus: e.g., 3-(2H)-thianaphthenone-1,1-dioxide, etc.

(i) A 2-thio-2,5-thiazolidinedione nucleus: e.g., 3-ethyl-2-thio-2,5-thiazolidinedione, etc.

(j) A 2,4-thiazolidinedione nucleus: e.g., 2,4-thiazolidinedione, 3-ethyl-2,4-thiazolidinedione, 3-phenyl-2,4-thiazolidinedione, etc.

(k) A thiazolin-4-one nucleus: e.g., 4-thiazolinone, 2-ethyl-4-thiazolinone, etc.

(l) A 4-thiazolidinone nucleus: e.g., 2-ethylmercapto-5-thiazolin-4-one, 2-alkylphenylamino-5-thiazolin-4-one, etc.

(m) A 2,4-imidazolidinedione (hydantoin) nucleus: e.g., 2,4-imidazolidinedione, 3-ethyl-2,4-imidazolidinedione, etc.

(n) A 2-thio-2,4-imidazolidinedione (2-thiohydantoin) nucleus: e.g., 2-thio-2,4-imidazolidinedione, 3-ethyl-2-thio-2,4-imidazolidinedione, etc.

(o) An imidazolin-5-one nucleus: e.g., 2-propylmercapto-2-imidazolin-5-one, etc.

(p) A 3,5-pyrazolidinedione nucleus: e.g., 1,2-diphenyl-3,5-pyrazolidinedione, 1,2-dimethyl-3,5-pyrazolidinedione, etc.

Preferred examples of the rings formed by $Z_1$ include a 1,3-dicarbonyl nucleus, a pyrazolinone nucleus, a 2,4,6-triketohexahydropyrimidine nucleus (including a thioketone form), a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, a 2-imidazolin-5-one nucleus, and a 3,5-pyrazolidinedione nucleus, more preferred are a 1,3-dicarbonyl nucleus, a 2,4,6-triketohexahydropyrimidine nucleus (including a thioketone form), and a 3,5-pyrazolidinedione nucleus, still more preferred are a cyclic 1,3-dicarbonyl nucleus, a barbituric acid derivative, a 2-thiobarbituric acid derivative, and a 3,5-pyrazolidinedione nucleus, and particularly preferred are 1,3-indanedione and 1,2-diphenyl-3,5-pyrazolidinedione.

$L_1$ and $L_2$ each represents a substituted or unsubstituted methine group. $L_1$ and $L_2$ may respectively form 4- to 6-membered rings via the substituent of the substituted methine group, or $L_1$ and $L_2$ may be linked to each other to form a 4- to 6-membered ring.

As the substituents of the substituted methine group, e.g., those exemplified as the substituents for $R_1$ to $R_9$ can be applied, preferably an alkyl group, an aryl group, an aralkyl group, an alkoxyl group, an aryloxy group, an alkylthio group, an arylthio group, a cyano group, or a halogen atom, more preferably an alkyl group or an alkoxyl group, and still more preferably a lower alkyl group (preferably having from 1 to 4 carbon atoms).

$L_1$ and $L_2$ each preferably represents an unsubstituted methine group, an alkyl-substituted methine group, or an alkoxyl-substituted methine group, and more preferably an unsubstituted methine group.

n represents 1 or 2, preferably 1.

The compound represented by formula (II) is preferably represented by formula (III):

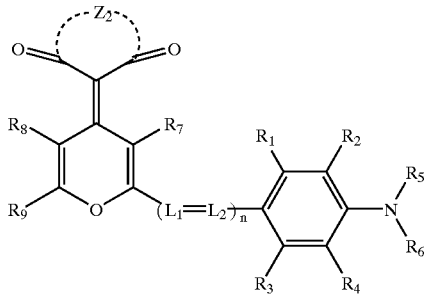

(III)

wherein $R_1$, $R_2$, $R_3$, $R_4$, $R_5$, $R_6$, $R_7$, $R_8$, $R_9$, $L_1$, $L_2$ and n each has the same meaning as defined in formula (II), and the preferred range is also the same. $Z_2$ represents an atomic group necessary for forming a 5- or 6-membered ring, as the 5- or 6-membered rings formed by $Z_2$, e.g., among the rings formed by $Z_1$ in formula (II), those having 1,3-dicarbonyl structure in the ring, e.g., 1,3-cyclopentanedione, 1,3-cyclohexanedione, 1,3-indanedione, and 3,5-pyrazolidinedione can be exemplified, and preferred are 1,3-indanedione and 1,2-diphenyl-3,5-pyrazolidinedione.

The compound represented by formula (II) is more preferably represented by formula (IV) or (V):

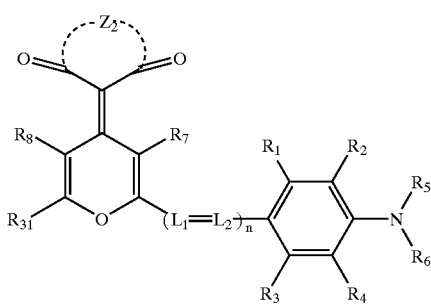

(IV)

wherein $R_1$, $R_2$, $R_3$, $R_4$, $R_5$, $R_6$, $R_7$, $R_8$, $L_1$, $L_2$, $Z_2$ and n each the same meaning as defined in formula (III), and the preferred range is also the same. $R_{13}$ represents an alkyl group having 2 or more carbon atoms (preferably an alkyl group having from 2 to 20 carbon atoms, more preferably a branched or cyclic alkyl group having from 3 to 20 carbon atoms, still more preferably a branched or cyclic alkyl group having from 4 to 12 quaternary carbon atoms, and particularly preferably a tert-butyl group), an aryl group (preferably an aryl group having from 6 to 30 carbon atoms, more preferably an aryl group having from 6 to 30 carbon atoms and substituted at the o-position, and still more preferably an o-alkyl-substituted phenyl group (e.g., a 2,6-dimethylphenyl group, a 2,4,6-trimethylphenyl group), and particularly preferably a 2,4,6-trimethylphenyl group.

When $R_7$ and $R_8$ both represent a hydrogen atom, $R_{31}$ more preferably represents a tert-butyl group, a 2,6-dimethylphenyl group or a 2,4,6-trimethylphenyl group, and still more preferably represents a tert-butyl group.

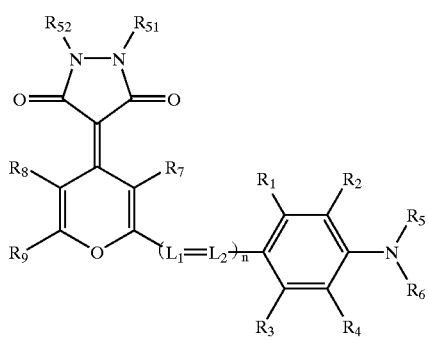

(V)

wherein $R_1$, $R_2$, $R_3$, $R_4$, $R_5$, $R_6$, $R_7$, $R_8$, $R_9$, $L_1$, $L_2$ and n each has the same meaning as defined in formula (II), and the preferred range is also the same. As the substituents represented by $R_{51}$ and $R_{52}$, e.g., those exemplified as the substituents for $R_1$ to $R_9$ in formula (II) can be applied, preferably a hydrogen atom, an alkyl group (preferably an alkyl group having from 1 to 20, more preferably from 1 to 12, and still more preferably from 1 to 8, carbon atoms), an aryl group (preferably an aryl group having from 6 to 30, more preferably from 6 to 20, and still more preferably from 6 to 12, carbon atoms), or a heterocyclic group, more preferably an alkyl group, an aryl group, or a heterocyclic group, still more preferably a methyl group, an ethyl group, or a substituted or unsubstituted phenyl group, particularly preferably a methyl group or a substituted or unsubstituted phenyl group, and most preferably a phenyl group. $R_{51}$ and $R_{52}$ may be linked together to form a ring, if possible.

The compound represented by formula (IV) is more preferably represented by formula (IV-a):

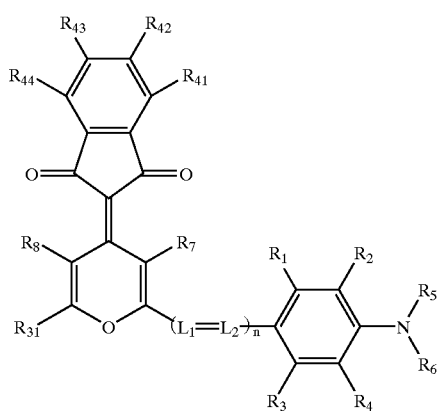

(IV-a)

wherein $R_1$, $R_2$, $R_3$, $R_4$, $R_5$, $R_6$, $R_7$, $R_8$, $L_1$, $L_2$ and n each has the same meaning as defined in formula (II), and the preferred range is also the same. $R_{31}$ has the same meaning as defined in formula (IV) and the preferred range is also the same. As the substituents represented by $R_{41}$, $R_{42}$, $R_{43}$ and $R_{44}$, e.g., those exemplified as the substituents for $R_1$ to $R_9$ in formula (II) can be applied. $R_{41}$ to $R_{44}$ may be linked together to form a ring, if possible. $R_{41}$ to $R_{44}$ each prefer ably represents a hydrogen atom, an alkyl group, an aryl group, a heterocyclic group, a halogen atom, a cyano group, an alkoxyl group, an aryloxy group, an alkoxycarbonyl group, or an aryloxycarbonyl group, more preferably a hydrogen atom, an alkyl group, an aryl group, a heterocyclic group, a halogen atom, or a cyano group, and particularly preferably a hydrogen atom.

The compound represented by formula (II) may be a low molecular weight compound, may be a high molecular weight compound the polymer main chain of which is connected with the residue represented by formula (II) (preferably having a weight average molecular weight of from 1,000 to 5,000,000, more preferably from 5,000 to 2,000,000, and still more preferably from 10,000 to 1,000,000), or may be a high molecular weight compound whose main chain has the skeleton of formula (II) (preferably having a weight average molecular weight of from 1,000 to 5,000,000, more preferably from 5,000 to 2,000,000, and still more preferably from 10,000 to 1,000,000). The high molecular weight compound may be a homopolymer or a copolymer with other monomers.

The compound represented by formula (II) is preferably a low molecular weight compound. Further, formula (II) is conveniently represented as an extreme structural formula but the compound may be a tautomer. When there exists a geometrical isomer, the compound may be either one.

Specific examples of the compound represented by formula (II) are shown below but the present invention is not limited thereto.

1 B

3 B

4 B

2 B

5 B

6 B

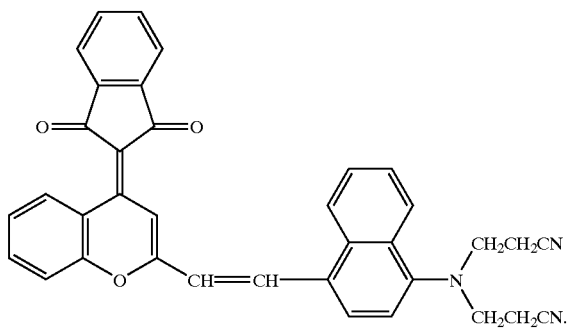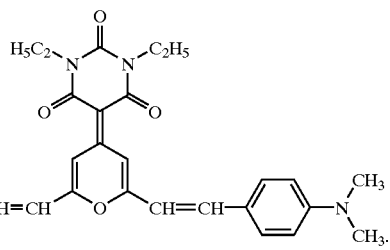

16 B
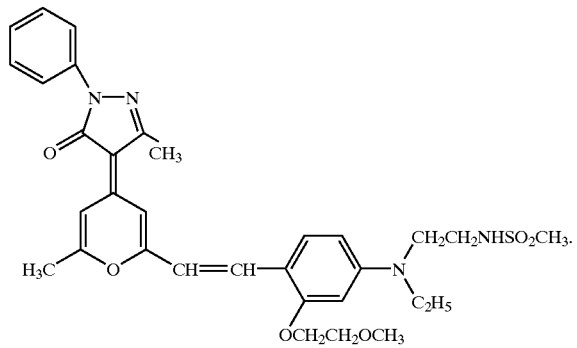
17 B
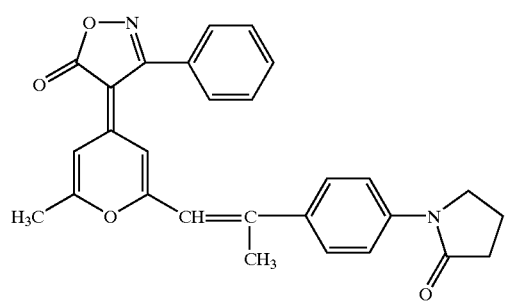
18 B
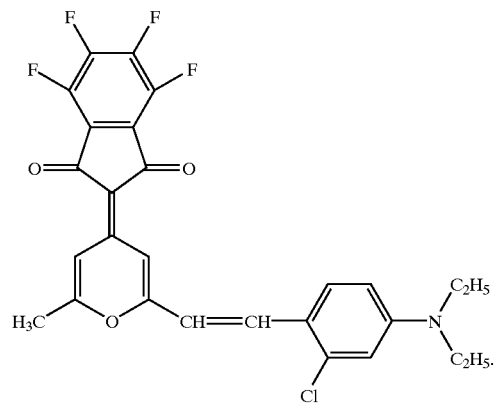
19 B
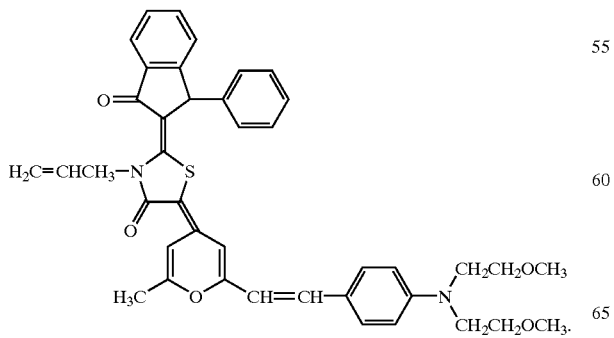
20 B
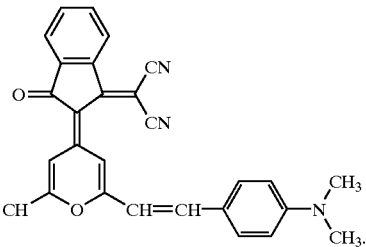
21 B
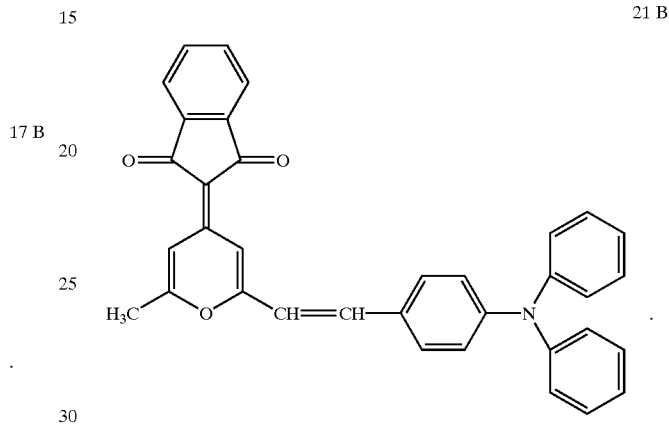
22 B
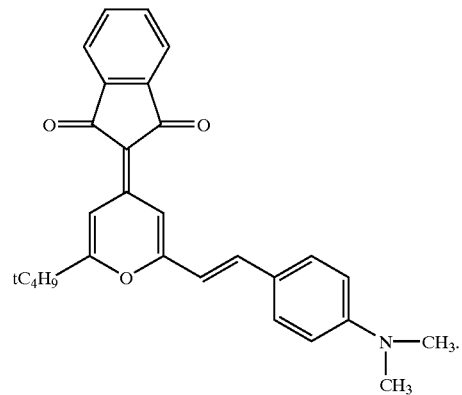
23 B
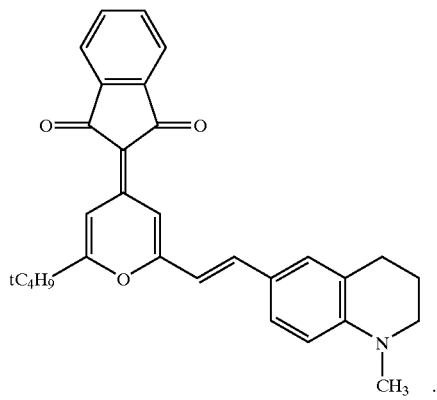

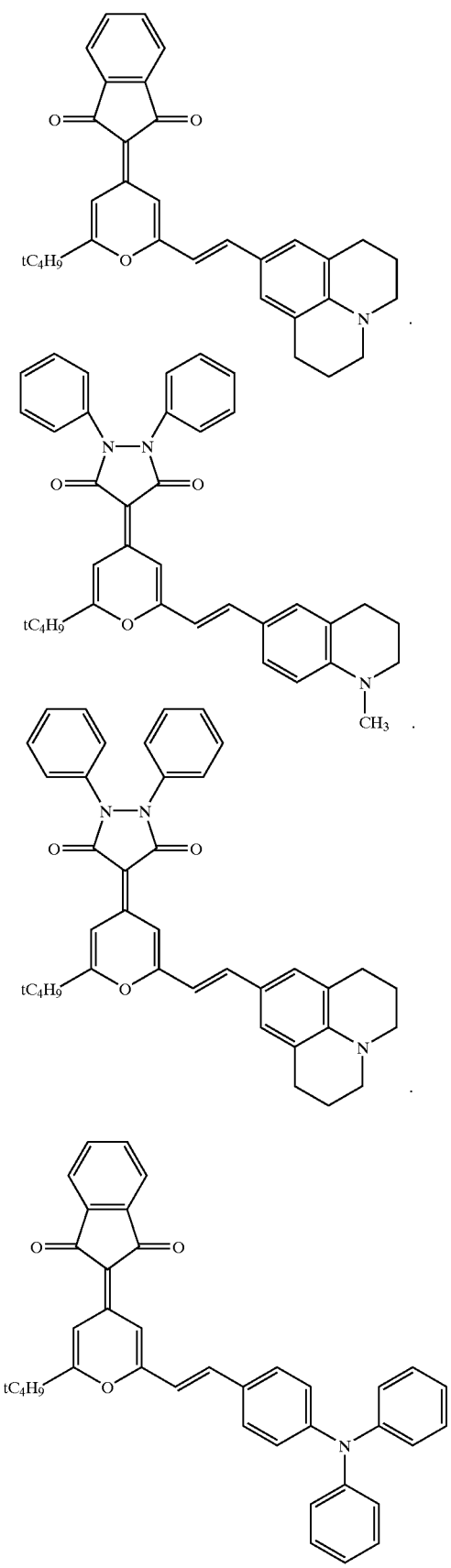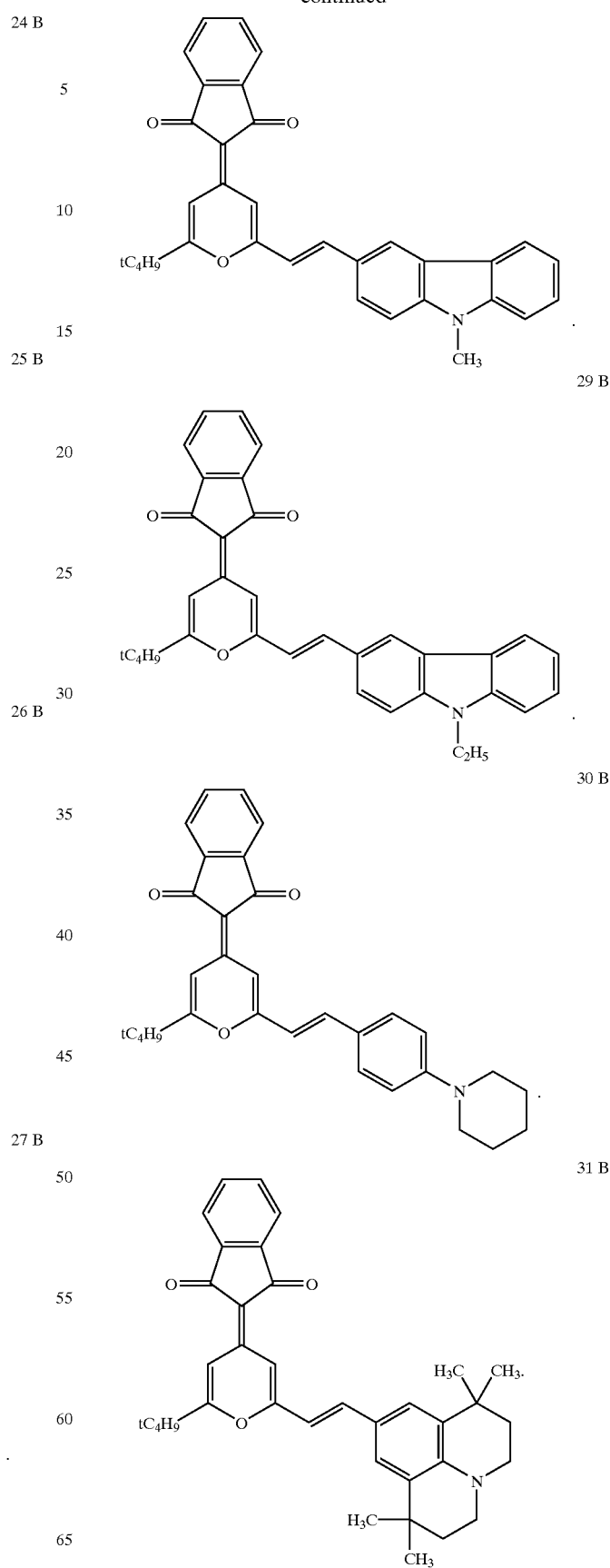

-continued
32 B
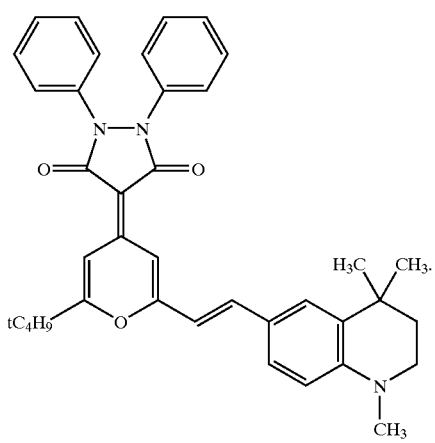
33 B
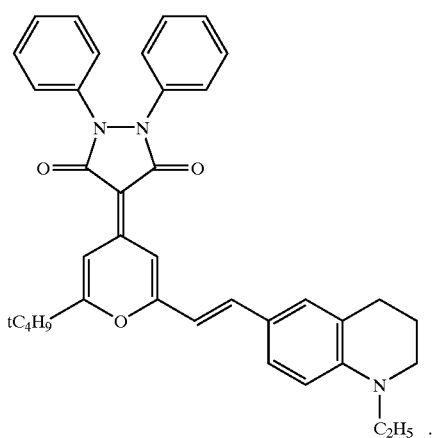
34 B
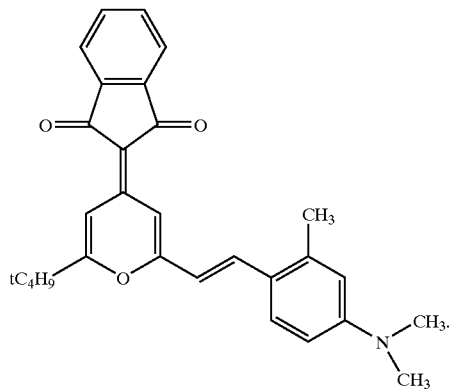
35 B
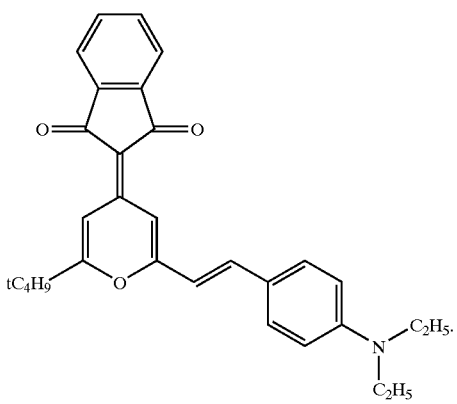
-continued
36 B
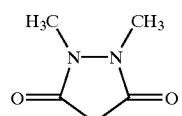
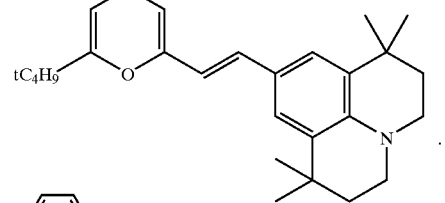
37 B
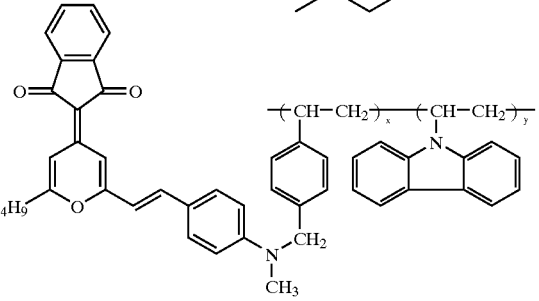
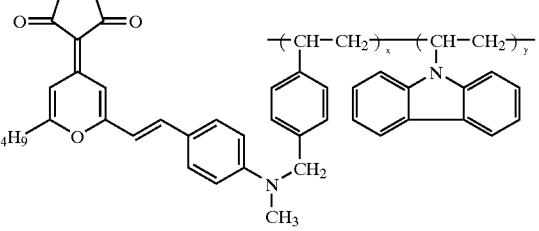
Weight average molecular weight (12,000, calculated in terms of polystyrene)
x/y=1/100 (by weight)
38 B
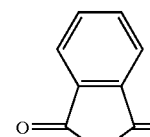
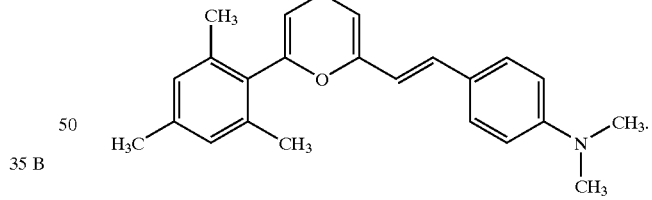
39 B
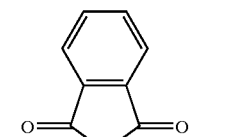
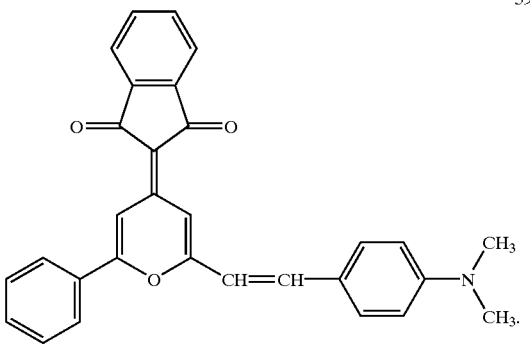

47

-continued

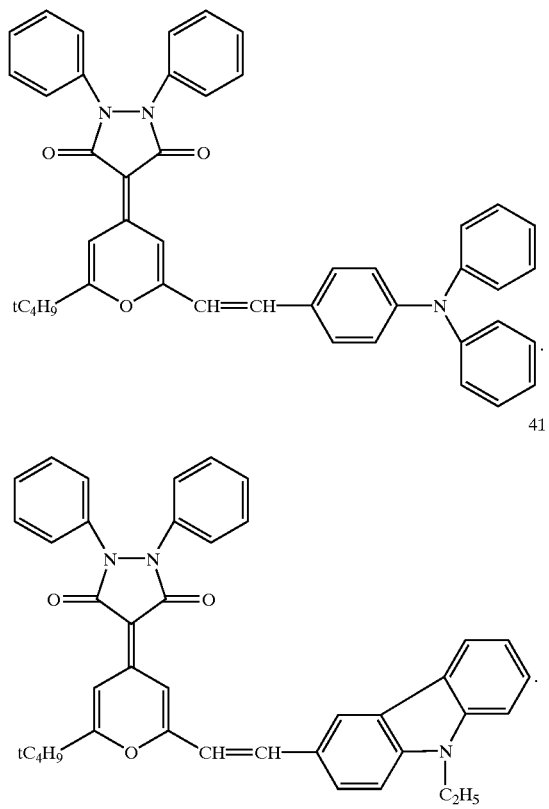

40 B

41 B

The above-described compounds may be tautomers thereof.

Synthesis methods of the compounds according to the present invention will be described below. Representative synthesis methods are shown in Schemes 1 to 3 below.

Synthesis Method of Intermediate (D)

Scheme 1

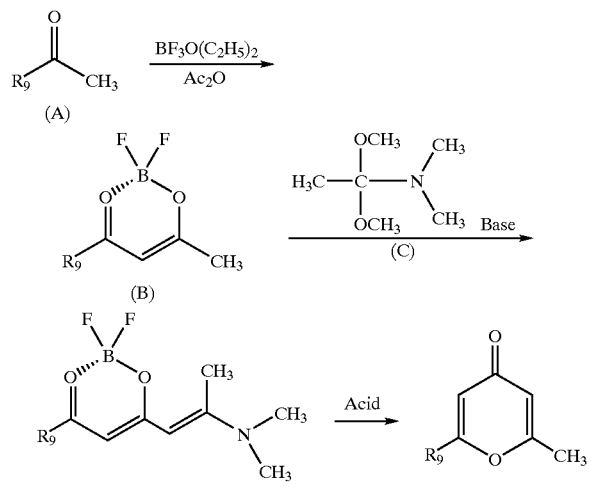

wherein $R_9$ has the same meaning as defined in Formula (II).

48

In Scheme 1, the synthesis of (A) to (B) is a synthesis method using ketone compound (A) and an acid anhydride in the presence of a boron trifluoride complex (see *Zeitschrift Chemie*, Vol. 28, p. 23 (1988)), the synthesis of (B) to (D) is a method using (B) and acetal compound (C) in the presence of a base, and the synthesis of (D) to (E) is a synthesis method based on the method of cyclization under the acidic conditions.

Synthesis Method of Intermediate (H)

Scheme 2

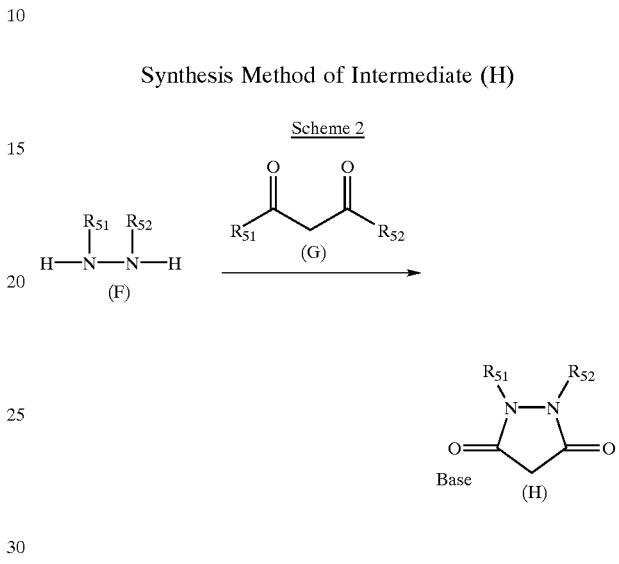

wherein $R_{51}$ and $R_{52}$ each has the same meaning as defined in formula (V).

In Scheme 2, the synthesis of (F) to (H) is a synthesis method based on the method of amidation of hydrazine derivative (F) and malonic acid derivative (G) in the presence of a base, and the synthesis can be performed according to the method described in *J. Gen. Chem. USSR*, Vol. 28, p. 2841 (1958).

Synthesis Method of Compound (L)

Scheme 3

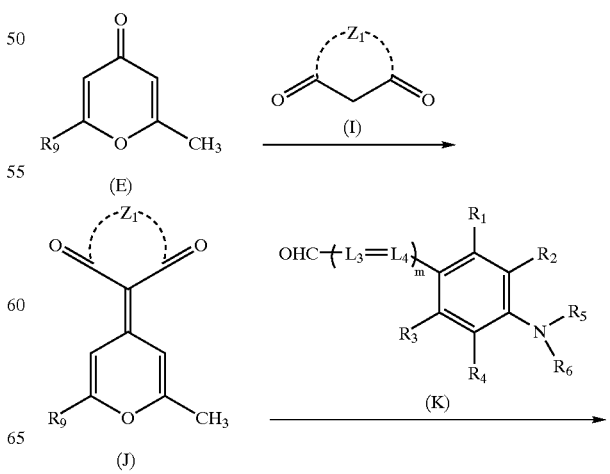

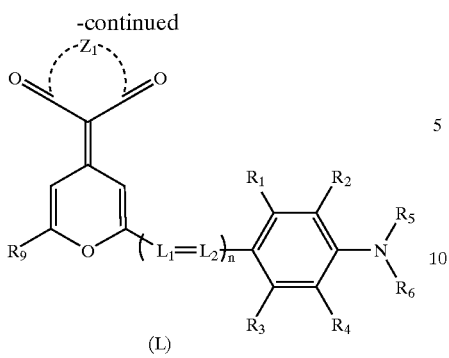

(L)

wherein $R_1$, $R_2$, $R_3$, $R_4$, $R_5$, $R_6$, $R_7$, $R_8$, $R_9$, $L_1$, $L_2$, $Z_1$ and n each has the same meaning as defined in formula (II), $L_3$ and $L_4$ each represents a substituted or unsubstituted methine group, and m represents 0 or 1.

In Scheme 3, the synthesis of (E) to (L) is a synthesis method based on a dehydration condensation reaction using acid anhydrides $R_8$ and $R_9$ to ketone compound (I) and intermediate (E) (see *J. Amer. Chem. Soc.*, Vol. 80, p. 1440 (1958). The synthesis of (J) to (L) is a synthesis method based on the Knoevenagl reaction of subjecting activated methylene and aldehyde to a dehydration condensation reaction in the presence of a base (see JP-A-60-83035) (the term "JP-A" as used herein means an "unexamined published Japanese patent application").

Specific examples of syntheses of the compounds represented by formula (II) according to the present invention are described below.

SYNTHESIS EXAMPLES

Synthesis of Intermediate d

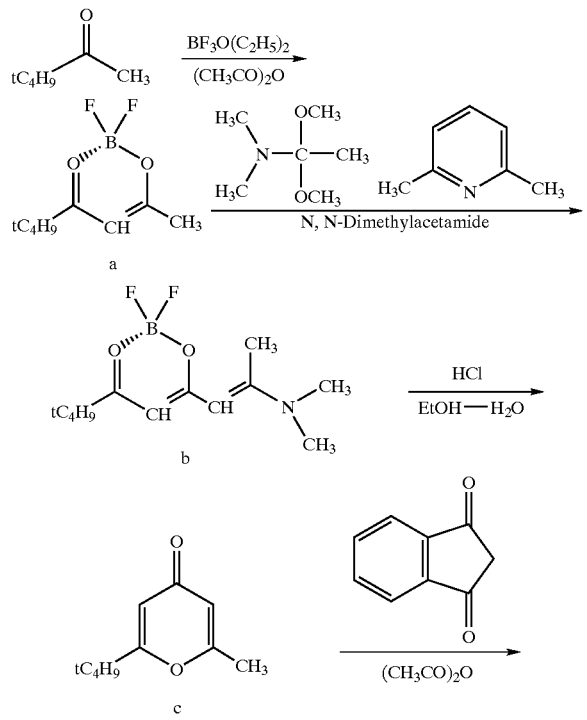

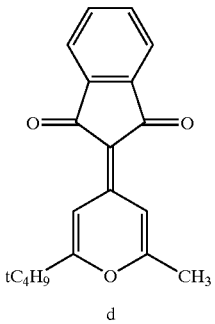

d

Synthesis of Compound a

One hundred and fifty (150) ml (1.1 mol) of boron trifluoride diethyl ether complex was dropwise added slowly to 100 g (1 mol) of t-butyl methyl ketone and 200 ml of acetic anhydride with maintaining the temperature at 0° C. The system was then stirred at room temperature for 3 hours, then extracted with chloroform and water to concentrate the organic phase. The extract was purified through a silica gel column chromatography to thereby obtain 72 g (yield: 38%) of Compound a.

Synthesis of Compound b

One hundred and eighty-eight (188) grams (1 mol) of Compound a and 178 ml (1 mol) of N,N-dimethylacetamide dimethylacetal were dissolved in 600 ml of N,N-dimethylacetamide, then 120 ml (1 mol) of 2,6-lutidine was added thereto, and the reaction system was stirred at room temperature for 5 hours. Water was added to the reaction solution, the solid precipitated was filtered out and dried, thereby 256 g (yield: 100%) of Compound b was obtained as an orange crystal.

Synthesis of Compound c

Two hundred and eighty (280) grams (1.08 mol) of Compound b was dissolved in 1,200 ml of ethanol and 200 ml of water, and 50 ml of concentrated hydrochloric acid was dropwise added to the solution. The reaction system was then stirred at room temperature for 9 hours, then extracted with ethyl acetate and water to concentrate the organic phase. The extract was purified through a silica gel column chromatography to thereby obtain 170 g (yield: 94%) of Compound c.

Synthesis of Compound d

Thirty point zero (30.0) grams (0.18 mol) of Compound c and 31.6 g (0.22 mol) of 1,3-indanedione were dissolved in 150 ml of acetic anhydride, the system was refluxed with heating for 8 hours, then the acetic anhydride was concentrated to 75 ml. The reaction solution was extracted with ethyl acetate and water to concentrate the organic phase. The extract was purified through a silica gel column chromatography, thereby 46.9 g (yield: 88%) of Compound d was obtained.

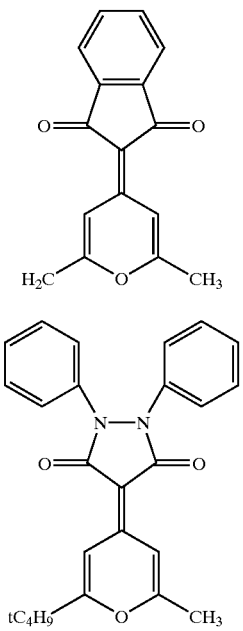

In place of Compound c, 28.5 g (0.23 mol) of 2,6-dimethyl-γ-pyron and 33.5 g (0.23 mol) of 1,3-indanedione were dissolved in 100 ml of acetic anhydride, and the system was refluxed with heating for 8 hours. The reaction solution was cooled to room temperature, ethanol was added thereto, and the solid precipitated was filtered out. The solid obtained was recrystallized with ethanol, thereby 39.0 g (yield: 67%) of Compound e was obtained.

Synthesis of Compound f

Three point six five (3.65) grams (22.8 mmol) of diethyl malonate and 4.00 g (21.7 mmol) of 1,2-diphenylhydrazine were dissolved in 10 ml of n-butanol, then 4.61 g (23.9 mmol) of a 28% methanol solution of sodium methoxide was added thereto, and the reaction system was heated at 100° C. for 10 hours. Subsequently, the solvent was distilled off under reduced pressure, 10 ml of water was added thereto and stirred, and then the reaction solution was filtered. An activated carbon was added to the recovered filtrate and stirred for 30 minutes. After stirring, the solution was filtered again to recover the filtrate. Four (4) ml of hydrochloric acid was added to the filtrate, and the precipitated solid was recovered by filtration. Thus, 3.76 g (yield: 60%) of 1,2-diphenyl-3,5-pyrazolidinedione was obtained.

Ten point one (10.1) grams (0.04 mmol) of 1,2-diphenyl-3,5-pyrazolidinedione and 6.64 g (0.04 mol) of Compound c were dissolved in 50 ml of acetic anhydride, and the solution was refluxed with heating for 8 hours. The acetic anhydride was concentrated to 30 ml, then the reaction solution was cooled to room temperature and allowed to stand overnight. The crystal precipitated was filtered, thereby 11.2 g (yield: 70%) of Compound f was obtained.

Synthesis of Exemplified Compound 1B

Five point zero (5.0) grams (20 mmol) of Compound e and 4.0 g (20 mmol) of 4-dimethylaminobenzaldehyde were dissolved in 100 ml of ethanol, 1.6 ml (16mmol) of piperidine was added thereto and the solution was refluxed with heating for 8 hours. The reaction solution was cooled to room temperature, and the solid precipitated was filtered out. The solid obtained was purified through a silica gel column chromatography, recrystallized with ethanol, thereby 3.6 g (yield: 10%) of exemplified Compound 1B was obtained. Melting Point: 242–244° C.

$^1$H-NMR (CDCl$_3$) δ (ppm)=2.6 (s, 3H), 3.1 (s, 6H), 6.6–6.8 (m, 3H), 7.3–7.8 (m, 7H), 8.2 (s, 1H), 8.4 (s, 1H).

Synthesis of Exemplified Compound 2B

Two point five two (2.52) grams (10 mmol) of Compound e and 2.01 g (10 mmol) of 9-formyleurholidine were dissolved in 75 ml of ethanol, 0.8 ml (8 mmol) of piperidine was added thereto and the solution was refluxed with heating for 8 hours. The reaction solution was cooled to room temperature, and the solid precipitated was filtered out. The solid obtained was recrystallized with ethanol, thereby 3.05 g (yield: 70%) of exemplified Compound 2B was obtained. Melting Point: 225° C.

$^1$H-NMR (CDCl$_3$) δ (ppm)=2.0 (m, 4H), 2.4 (s, 3H), 2.8 (t, 4H), 3.3 (t, 4H), 6.6 (d, 1H), 7.3 (d, 2H), 7.6–7.8 (m, 4H), 8.3 (s, 1H), 8.4 (s, 2H).

Synthesis of Exemplified Compound 8B

Two point five two (2.52) grams (10 mmol) of Compound e and 4.02 g (20 mmol) of 4-dimethylaminobenzaldehyde were dissolved in 50 ml of pyridine, 1.0 ml (10 mmol) of piperidine was added thereto and the solution was refluxed with heating for 16 hours. The reaction solution was cooled to room temperature, and the solid precipitated was filtered out. The solid obtained was recrystallized with pyridine, thereby 4.2 g (yield: 82%) of exemplified Compound 8B was obtained. Melting Point: 290° C.

$^1$H-NMR (CDCl$_3$) δ (ppm)=3.0 (s, 12H), 6.6–6.7 (m, 6H), 7.4–7.5 (m, 6H), 7.6 (m, 2H), 7.7 (m, 2H), 8.4 (s, 2H).

Synthesis of Exemplified Compound 22B

One point eight nine (1.89) grams (6.4 mmol) of Compound d and 0.96 g (6.4 mmol) of 4-dimethylaminobenzaldehyde were dissolved in 30 ml of ethanol, 0.16 ml (1.6 mmol) of piperidine was added thereto and the solution was refluxed with heating for 8 hours. The reaction solution was cooled to room temperature, and the solid precipitated was filtered out. The solid obtained was recrystallized with ethanol, thereby 1.49 g (yield: 55%) of exemplified Compound 22B was obtained. Melting Point: 253° C.

$^1$H-NMR (CDCl$_3$) δ (ppm)=1.4 (s, 9H), 3.1 (s, 6H), 6.7–6.8 (m, 3H), 7.4–7.8 (m, 10H), 8.4 (d, 2H).

Synthesis of Exemplified Compound 23B

Three point zero zero (3.00) grams (10.2 mmol) of Compound d and 1.80 g (10.2 mmol) of 6-formyl-1-methyl-1,2,3,4-tetrahydroquinoline (which can be synthesized according to the method described in J. Chem. Soc., p. 2147, (1948)) was dissolved in 50 ml of ethanol, 0.20 ml (2.25 mmol) of piperidine was added thereto and the solution was refluxed with heating for 4 hours. The reaction solution was cooled to room temperature, and the solid precipitated was filtered out. The solid obtained was recrystallized with ethanol, thereby 1.4 g (yield: 31%) of exemplified Compound 23B was obtained. Melting Point: 243–246° C.

$^1$H-NMR (CDCl$_3$) δ (ppm)=1.45 (S, 9H), 2.0 (m, 2H), 2.75 (t, 2H), 3.0 (s, 3H), 3.35 (t, 2H), 6.55–6.70 (m, 2H), 7.20–7.35 (m, 3H), 7.6 (m, 2H), 7.76 (m, 2H), 8.4 (d, 2H).

Synthesis of Exemplified Compound 24B

One point six seven (1.67) grams (4 mmol) of Compound d and 1.14 g (4 mmol) of 9-formyleurholidine were dissolved in 50 ml of ethanol, 0.32 ml (4 mmol) of piperidine was added thereto and the solution was refluxed with heating for 7 hours. The reaction solution was cooled to room temperature, and the solid precipitated was filtered out. The solid obtained was recrystallized with ethanol, thereby 2.20 g (yield: 81%) of exemplified Compound 24B was obtained. Melting Point: 220–222° C.

$^1$H-NMR (CDCl$_3$) δ (ppm)=1.45 (s, 9H), 1.97 (m, 4H), 2.78 (t, 4H), 3.22 (t, 4H), 6.57 (d, 1H), 7.04 (s, 2H), 7.29 (d, 1H), 7.52–7.79 (m, 4H), 8.40 (d, 2H).

Synthesis of Exemplified Compound 25B

Three point six (3.6) grams (9.0 mmol) of Compound f and 1.6 g (9.0 mmol) of 6-formyl-1-methyl-1,2,3,4-tetrahydroquinoline was dissolved in 50 ml of ethanol, 0.20 ml (2.25 mmol) of piperidine was added thereto and the solution was refluxed with heating for 4 hours. The reaction solution was cooled to room temperature, and the solid precipitated was filtered out. The solid obtained was recrystallized with ethanol, thereby 2.7 g (yield: 54%) of exemplified Compound 25B was obtained. Melting Point: 240–242° C.

$^1$H-NMR (CDCl$_3$) δ (ppm)=1.4 (s, 9H), 2.0 (m, 2H), 2.75 (t, 2H), 3.0 (s, 3H), 3.35 (t, 2H), 6.5–6.6 (m, 2H), 7.05–7.45 (m, 13H), 8.4 (d, 2H).

Synthesis of Exemplified Compound 26B

Two point zero zero (2.00) grams (5.0 mmol) of Compound f and 1.05 g (5.0 mmol) of 9-formyleurholidine were dissolved in 25 ml of ethanol, 0.12 ml (1.25 mmol) of piperidine was added thereto and the solution was refluxed with heating for 6 hours. The reaction solution was cooled to room temperature, and the solid precipitated was filtered out. The solid obtained was recrystallized with ethanol, thereby 1.60 g (yield: 55%) of exemplified Compound 26B was obtained. Melting Point: 219–222° C.

$^1$H-NMR (CDCl$_3$) δ (ppm)=1.4 (s, 9H), 2.0 (m, 4H), 2.4 (s, 3H), 2.8 (t, 4H), 3.3 (t, 4H), 6.6 (d, 1H), 7.0–7.5 (m, 13H), 8.4 (s, 2H).

Synthesis of Exemplified Compound 27B

Two point nine four (2.94) grams (10.0 mmol) of Compound d and 2.73 g (10.0 mmol) of 4-diphenylaminobenzaldehyde (which can be synthesized according to the method described in *J. Org. Chem.*, Vol. 30, p. 3714 (1965)) were dissolved in 20 ml of ethanol, 0.5 ml (5.1 mmol) of piperidine was added thereto and the solution was refluxed with heating for 8 hours. The reaction solution was cooled to room temperature, and the solid precipitated was filtered out. The solid obtained was recrystallized with ethanol, thereby 2.1 g (yield: 40%) of exemplified Compound 27B was obtained. Melting Point: 227–229° C.

$^1$H-NMR (CDCl$_3$) δ (ppm)=1.4 (s, 9H), 6.7 (d, 1H), 7.0–7.5 (m, 15H), 7.6 (m, 2H), 7.8 (m, 2H), 8.5 (s, 2H).

Synthesis of Exemplified Compound 29B

One point eight zero (1.80) grams (6.1 mmol) of Compound d and 1.36 g (6.1 mmol) of 9-ethylcarbazole-3-carvaldehyde were dissolved in 25 ml of ethanol, 0.10 ml (1.5 mmol) of piperidine was added thereto and the solution was refluxed with heating for 4 hours. The reaction solution was cooled to room temperature, and the solid precipitated was filtered out. The solid obtained was recrystallized with ethanol, thereby 1.50 g (yield: 50%) of exemplified Compound 29B was obtained. Melting Point: 249–250° C.

$^1$H-NMR (CDCl$_3$) δ (ppm)=1.5 (m, 12H), 4.4 (q, 2H), 6.9 (d, 1H), 7.3–7.8 (m, 10H), 8.1 (d, 1H), 8.3 (s, 1H), 8.5 (d, 2H).

Synthesis of Exemplified Compound 34B

One point eight zero (1.80) grams (6.1 mmol) of Compound d and 1.00 g (6.1 mmol) of 4-dimethylamino-2-methylbenzaldehyde were dissolved in 20 ml of ethanol, 0.20 ml (3.0 mmol) of piperidine was added thereto and the solution was refluxed with heating for 6 hours. The reaction solution was cooled to room temperature, and the solid precipitated was filtered out. The solid obtained was recrystallized with ethanol, thereby 1.23 g (yield: 46%) of exemplified Compound 34B was obtained. Melting Point: 278–280° C.

$^1$H-NMR (CDCl$_3$) δ (ppm)=1.40 (s, 9H), 2.47 (s, 3H), 3.04 (s, 6H), 6.50–6.67 (m, 3H), 7.56–7.77 (m, 6H), 8.43 (d, 2H).

Synthesis of Exemplified Compound 40B

Four point zero zero (4.00) grams (10.0 mmol) of Compound f and 2.73 g (10.0 mmol) of 4-diphenylaminobenzaldehyde were dissolved in 20 ml of ethanol, 0.5 ml (2.5 mmol) of piperidine was added thereto and the solution was refluxed with heating for 8 hours. The reaction solution was cooled to room temperature, and the solid precipitated was filtered out. The solid obtained was recrystallized with ethanol, thereby 4.7 g (yield: 72%) of exemplified Compound 40B was obtained. Melting Point: 216–217° C.

$^1$H-NMR (CDCl$_3$) δ (ppm) 1.4 (s, 9H), 6.7 (d, 1H), 7.0–7.6 (m, 25H), 8.5 (d, 2H).

Synthesis of Exemplified Compound 41B

Four point zero zero (4.00) grams (10.0 mmol) of Compound f and 2.23 g (10.0 mmol) of 9-ethylcarbazole-3-carvaldehyde were dissolved in 20 ml of ethanol, 0.25 ml (2.5 mmol) of piperidine was added thereto and the solution was refluxed with heating for 8 hours. The reaction solution was cooled to room temperature, and the solid precipitated was filtered out. The solid obtained was recrystallized with ethanol, thereby 2.6 g (yield: 43%) of exemplified Compound 41B was obtained. Melting Point: 238–239° C.

$^1$H-NMR (CDCl$_3$) δ (ppm)=1.4 (m, 12H), 4.4 (q, 2H), 6.9 (d, 1H), 7.1–8.3 (m, 18H), 8.5 (d, 2H).

The compound represented by formula (VI) of the present invention is described in detail below.

$R_1$, $R_2$, $R_3$, $R_4$, $R_5$, $R_6$, $R_7$, $R_8$, $R_9$ and R each represents a hydrogen atom or a substituent. Examples of the substituents represented by $R_1$, $R_2$, $R_3$, $R_4$, $R_5$, $R_6$, $R_7$, $R_8$, $R_9$ and R include an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, naphthyl), an amino group (preferably an amino group having from 0 to 20, more preferably from 0 to 10, and particularly preferably from 0 to 6, carbon atoms, e.g., amino, methylamino, dimethylamino, diethylamino, benzylamino), an alkoxyl group (preferably an alkoxyl group having from 1 to 20, more preferably from 1 to 12, and particularly preferably from 1 to 8, carbon atoms, e.g., methoxy, ethoxy, butoxy), an aryloxy group (preferably an aryloxy group having from 6 to 20, more preferably from 6 to 16, and particularly preferably from 6 to 12, carbon atoms, e.g., phenyloxy, 2-naphthyloxy), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e. g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), an acyloxy group (preferably an acyloxy group having from 2 to 20, more preferably from 2 to 16, and particularly preferably from 2 to 10, carbon atoms, e.g., acetoxy, benzoyloxy), an acylamino group (preferably an acylamino group having from 2 to 20, more preferably from 2 to 16, and particularly preferably from 2 to 10, carbon atoms, e.g., acetylamino, benzoylamino), an alkoxycarbonylamino group (preferably an alkoxycarbonylamino group having from 2 to 20, more preferably from 2 to 16, and particularly preferably from 2 to 12, carbon atoms, e.g., methoxycarbonylamino), an aryloxycarbonylamino group (preferably an aryloxycarbonylamino group having from 7 to 20, more preferably from 7 to 16, and particularly preferably from 7 to 12, carbon atoms, e.g., phenyloxycarbonylamino), a sulfonylamino group (preferably a sulfonylamino group having from 1 to 20, more preferably from 1 to 16, and particularly preferably from 1 to 12, carbon atoms, e.g., methanesulfonylamino, benzenesulfonylamino), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenylsulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenylcarbamoyl), an alkylthio group (preferably an alkylthio group having from 1 to 20, more preferably from 1 to 16, and particularly preferably from 1 to 12, carbon atoms, e.g., methylthio, ethylthio), an arylthio group (preferably an arylthio group having from 6 to 20, more preferably from 6 to 16, and particularly preferably from 6 to 12, carbon atoms, e.g., phenylthio), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), a ureido group (preferably a ureido group having from 1 to 20, more preferably from 1 to 16, and particularly preferably from 1 to 12, carbon atoms, e.g., ureido, methylureido, phenylureido), a phosphoric acid amido group (preferably a phosphoric acid amido group having from 1 to 20, more preferably from 1 to 16, and particularly preferably from 1 to 12, carbon atoms, e.g., diethylphosphoric acid amido, phenylphosphoric acid amido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, and a heterocyclic group (preferably a heterocyclic group having from 1 to 20, and more preferably from 1 to 12, carbon atoms; as hetero atoms, e.g., nitrogen, oxygen, sulfur, and specifically, e.g., imidazolyl, pyridyl, furyl, piperidyl, morpholino, benzoxazolyl, benzimidazolyl, benzothiazolyl can be exemplified). These substutuents may further be substituted. When there are two or more substituents, they may be the same or different. Substituents may be linked together to form a ring, if possible.

Preferred examples of the substituents include an alkyl group, an alkenyl group, an aralkyl group, an aryl group, an acyl group, an alkoxycarbonyl group, an aryloxycarbonyl group, a carbonylamino group, a sulfonylamino group, a sulfamoyl group, a carbamoyl group, a sulfonyl group, a cyano group, a halogen atom, a hydroxyl group, and a heterocyclic group, more preferred examples include an alkyl group, an alkenyl group, an aryl group, an acyl group, an alkoxycarbonyl group, a carbonylamino group, a sulfonylamino group, a sulfonyl group, a cyano group, a halogen atom, and a heterocyclic group, and still more preferred examples include an alkyl group, an aryl group, an acyl group, an alkoxycarbonyl group, a sulfonyl group, a cyano group, and an azole group.

$R_1$ and $R_3$ each preferably represents a hydrogen atom, an alkyl group, an alkoxyl group, an alkoxycarbonyl group, a cyano group, or a condensed ring formed by the linkage of $R_1$ with $R_2$, or $R_3$ with $R_4$, and more preferably a hydrogen atom.

$R_2$ and $R_4$ each preferably represents a hydrogen atom, an alkyl group, or a condensed ring formed by the linkage of $R_2$ with $R_1$, $R_4$ with $R_3$, $R_2$ with $R_5$, or $R_4$ with $R_6$, more preferably a hydrogen atom or a condensed ring formed by the linkage of $R_2$ with $R_5$, or $R_4$ with $R_6$, and still more preferably a hydrogen atom or a 6-membered ring formed by the linkage of $R_2$ with $R_5$, or $R_4$ with $R_6$, via an alkylene group.

$R_5$ and $R_6$ each preferably represents a hydrogen atom, an alkyl group, an alkylene group, or an aryl group, more preferably a hydrogen atom, an alkyl group, or an alkylene group, and still more preferably a hydrogen atom or a 6-membered ring formed by the linkage of $R_5$ with $R_2$, or $R_6$ with $R_4$, via an alkylene group.

$R_7$ preferably represents a hydrogen atom, an alkyl group, an aryl group, a halogen atom, or a cyano group, more preferably a hydrogen atom or an alkyl group, and still more preferably a hydrogen atom.

$R_8$ preferably represents a hydrogen atom, an alkyl group, an aryl group, a halogen atom, a cyano group, or a ring formed by linking with $R_9$, more preferably a hydrogen atom or an alkyl group, and still more preferably a hydrogen atom.

$R_9$ preferably represents a hydrogen atom, an alkyl group, an aryl group, a ring formed by linking with $R_8$, or

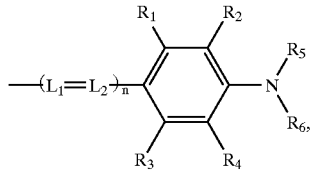

(wherein $R_1$, $R_2$, $R_3$, $R_4$, $R_5$, $R_6$, $L_1$, $L_2$, and n each has the same meaning as in formula (VI), and preferred range is also the same), more preferably a hydrogen atom, an alkyl group, or

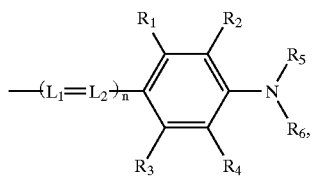

still more preferably a methyl group or

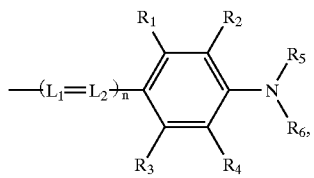

and particularly preferably a methyl group.

R preferably represents an electron-attractive group, e.g., a cyano group, a carbonyl group, a thiocarbonyl group, an aryl group (e.g., phenyl, naphthyl), an aromatic heterocyclic group (e.g., pyridyl, quinolyl, isoquinolyl, furyl, thienyl, oxazolyl, thiazolyl, imidazolyl, oxadiazolyl, thiadiazolyl, triazolyl, tetrazolyl, benzoxazolyl, benzimidazolyl, benzothiazolyl, benzoselenazolyl, pyrimidyl, pyrazinyl, phthalazinyl, quinoxalinyl, naphthyridinyl, indazolyl, quinazolinyl, cinnolinyl, pteridinyl, carbazolyl, indolyl), a sulfonyl group, a carbamoyl group, or a sulfamoyl group, more preferably a cyano group, a carbonyl group, a sulfonyl group, or an aromatic heterocyclic group, more preferably a cyano group, a carbonyl group, or an aromatic azolyl group, and particularly preferably a cyano group.

A represents a heterocyclic ring containing an aromatic ring, e.g., furyl, pyrrolyl, imidazolyl, pyrazolyl, pyridyl, pyrazinyl, pyrimidinyl, pyridazinyl, indolyl, isoindolyl, indolizinyl, phenoxazinyl, xanthenyl, indazolyl, purinyl, quinolyl, isoquinolyl, phthalazinyl, naphthyridinyl, quinoxalinyl, quinazolinyl, cinnolinyl, pteridinyl, carbazolyl, carbolinyl, phenanthridinyl, acridinyl, pteridinyl, phenanthrinyl, phenazinyl, isothiazolyl, isooxazolyl, phenothiazinyl, furazanyl, phenoxazinyl, oxazolyl, benzoxazolyl, thiazolyl, benzothiazolyl, selenazolyl, benzoselenazolyl, oxadiazolyl, thiadiazolyl, triazolyl, benzotriazolyl, tetrazolyl, tetraazaindenyl, or indolenyl. A preferably represents imidazolyl, pyridyl, pyrazinyl, pyrimidinyl, pyridazinyl, quinolyl, isoquinolyl, phthalazinyl, naphthyridinyl, quinoxalinyl, quinazolinyl, cinnolinyl, pteridinyl, oxazolyl, benzoxazolyl, thiazolyl, benzothiazolyl, oxadiazolyl, or thiadiazolyl, and more preferably represents benzoxazolyl, benzothiazolyl, or indolenyl.

X represents an oxygen atom, a sulfur atom, or $N-R_{10}$, wherein $R_{10}$ represents a hydrogen atom or a substituent. Examples of the substituents represented by $R_{10}$ include, for example, an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl, allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, naphthyl), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e.g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenylsulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenylcarbamoyl), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), and a heterocyclic group (preferably a heterocyclic group having from 1 to 20, and more preferably from 1 to 12, carbon atoms; as hetero atoms, e.g., nitrogen, oxygen, sulfur, and specifically, e.g., imidazolyl, pyridyl, furyl, piperidyl, morpholino, benzoxazolyl, benzimidazolyl, benzothiazolyl can be exemplified). These substutuents may further be substituted. When there are two or more substituents, they may be the same or different. Substituents may be linked together to form a ring, if possible.

Preferred examples of the substituents represented by $R_{10}$ include an alkyl group, an alkenyl group, an alkynyl group, an aryl group, and a heterocyclic group, more preferred are an alkyl group, an aryl group, and an aromatic heterocyclic group, and still more preferred examples are an alkyl group and an aryl group.

X preferably represents an oxygen atom or $N-R_{10}$, and more preferably an oxygen atom.

$L_1$ and $L_2$ each represents a substituted or unsubstituted methine group. $L_1$ and $L_2$ may respectively form 4- to 6-membered rings via the substituent of the substituted methine group, or $L_1$ and $L_2$ may be linked to each other to form a 4- to 6-membered ring.

As the substituents of the substituted methine group, e.g., those exemplified as the substituents for $R_1$ to $R_9$ can be applied, preferably an alkyl group, an aryl group, an aralkyl group, an alkoxyl group, an aryloxy group, an alkylthio group, an arylthio group, a cyano group, or a halogen atom, more preferably an alkyl group, an alkoxyl group, or a cyano group, and still more preferably a lower alkyl group (preferably having from 1 to 4 carbon atoms).

$L_1$ and $L_2$ each preferably represents an unsubstituted methine group, an alkyl-substituted methine group, or an alkoxyl-substituted methine group, and more preferably an unsubstituted methine group.

n represents 1 or 2, preferably 1.

The compound represented by formula (VI) is preferably represented by formula (VII):

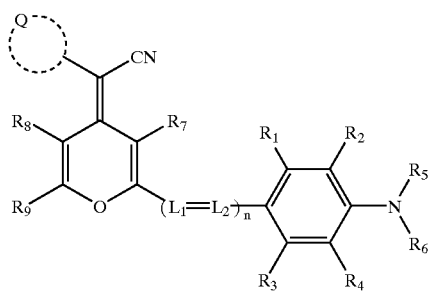

(VII)

wherein $R_1$, $R_2$, $R_3$, $R_4$, $R_5$, $R_6$, $R_7$, $R_8$, $R_9$, $L_1$, $L_2$ and n each has the same meaning as defined in formula (VI), and the preferred range is also the same. Q represents an aromatic azole group. Examples of the aromatic azole group represented by Q include, e.g., pyridine, imidazole, oxazole, thiazole, benzoxazole, benzothiazole, benzimidazole, and indolenine, preferably benzoxazole, benzothiazole, benzimidazole, and indolenine.

The compound represented by formula (VI) is more preferably represented by formula (VIII):

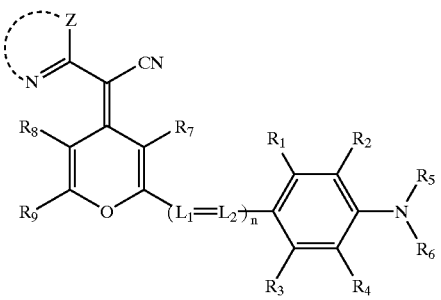

(VIII)

wherein $R_1$, $R_2$, $R_3$, $R_4$, $R_5$, $R_6$, $R_7$, $R_8$, $R_9$, $L_1$, $L_2$ and n each has the same meaning as defined in formula (VI), and the preferred range is also the same. Z represents an atomic group necessary for forming a 5- or 6-membered nitrogen-containing aromatic heterocyclic ring. Examples of the nitrogen-containing aromatic heterocyclic rings formed by Z include pyridine, imidazole, oxazole, thiazole, benzoxazole, benzothiazole, benzimidazole, and indolenine, preferably benzoxazole, benzothiazole, benzimidazole, and indolenine, and particularly preferably benzoxazole.

The compound represented by formula (VI) may be a low molecular weight compound, may be a high molecular weight compound the polymer main chain of which is connected with the residue represented by formula (VI) (preferably having a weight average molecular weight of from 1,000 to 5,000,000, more preferably from 5,000 to 2,000,000, and still more preferably from 10,000 to 1,000,000, calculated in terms of polystyrene), or may be a high molecular weight compound whose main chain has the skeleton of formula (VI) (preferably having a weight average molecular weight of from 1,000 to 5,000,000, more preferably from 5,000 to 2,000,000, and still more preferably from 10,000 to 1,000,000). The high molecular weight compound may be a homopolymer or a copolymer with other monomers.

The compound represented by formula (VI) is preferably a low molecular weight compound. Further, formula (VI) is conveniently represented as an extreme structural formula but the compound may be a tautomer.

Specific examples of the compound represented by formula (VI) are shown below but the present invention is not limited thereto.

1C

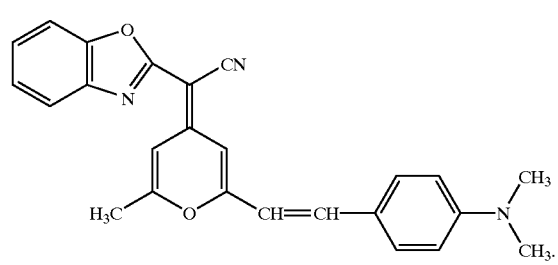

2C

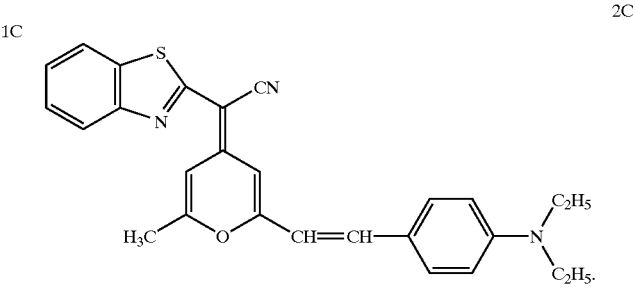

3C

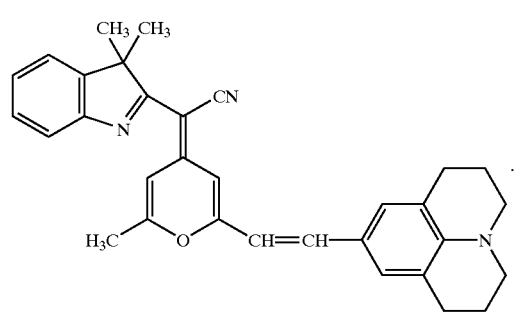

4C

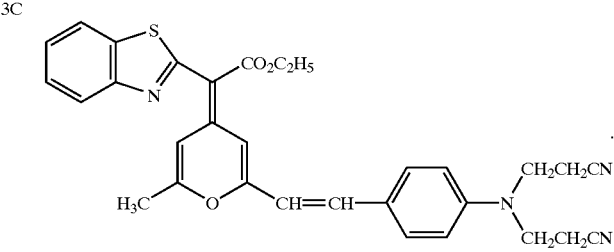

-continued
5C 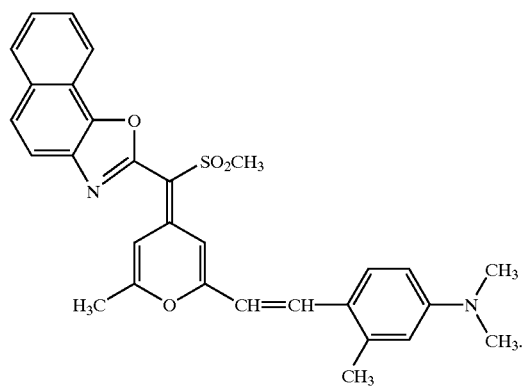
6C 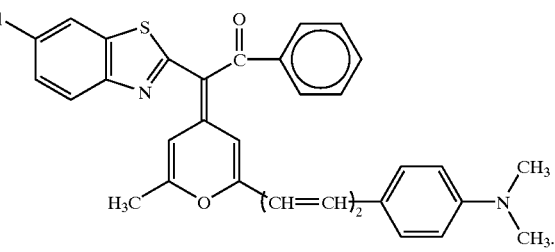
7C 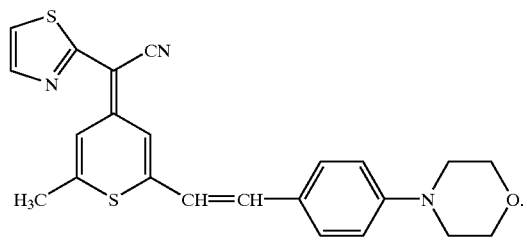
8C 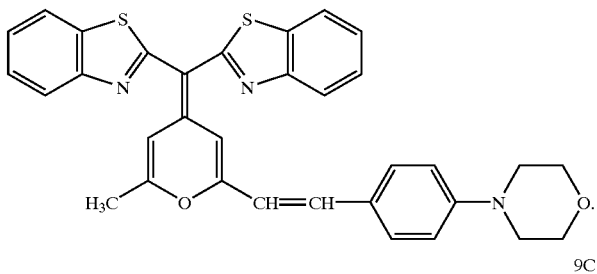
9C 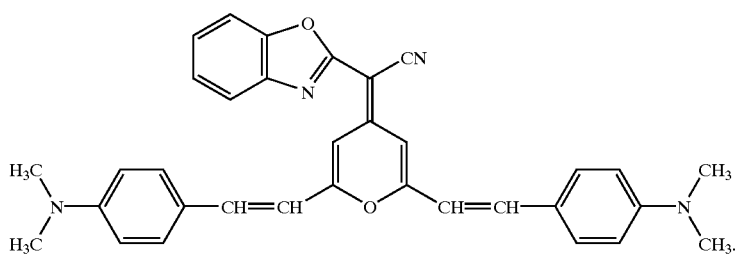
10C 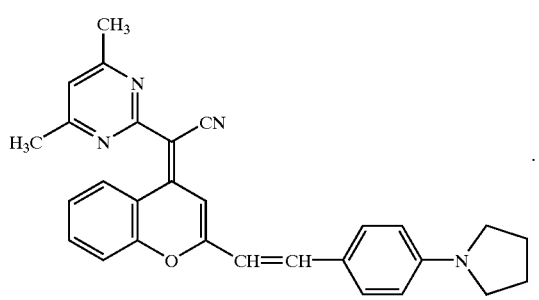
11C 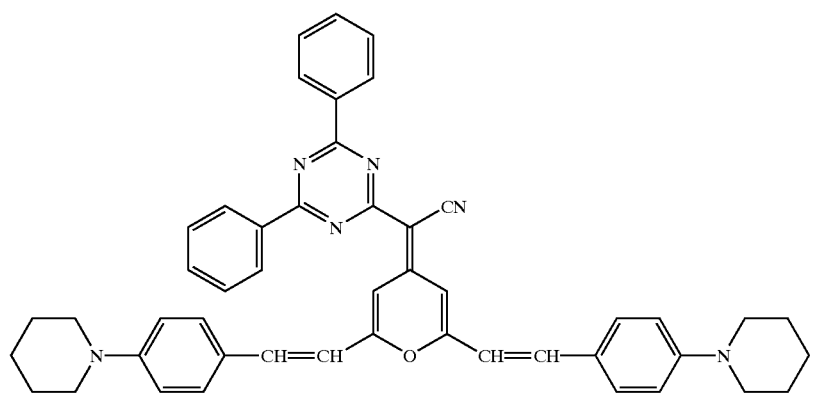

12C
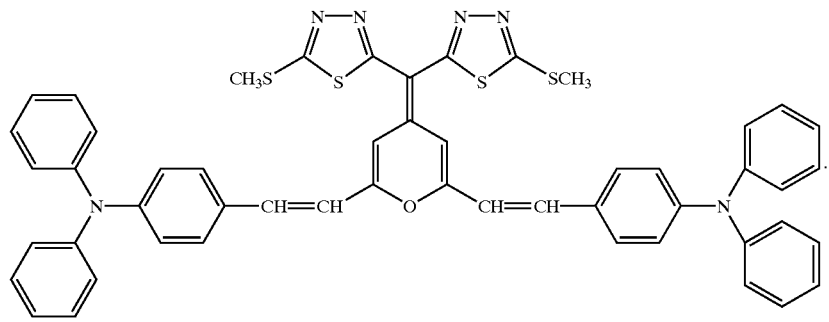
13C
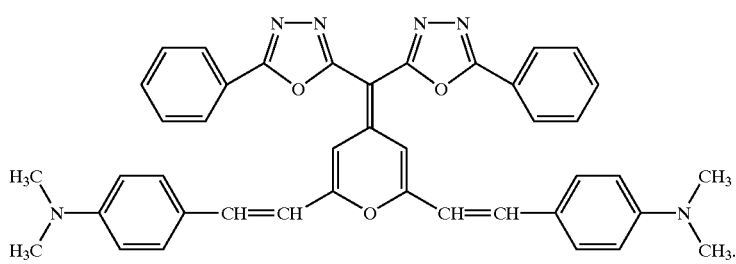
14C
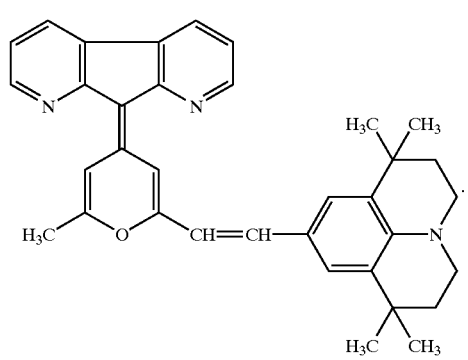
15C
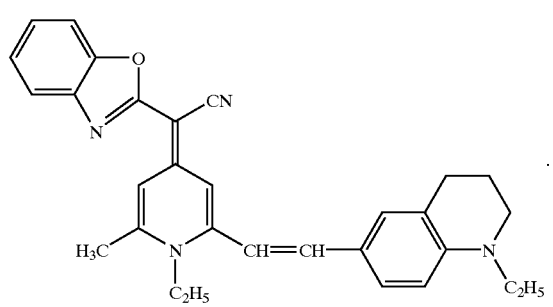
16C
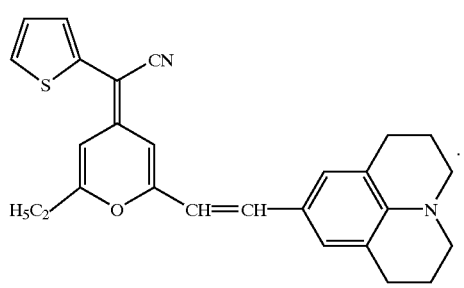
17C
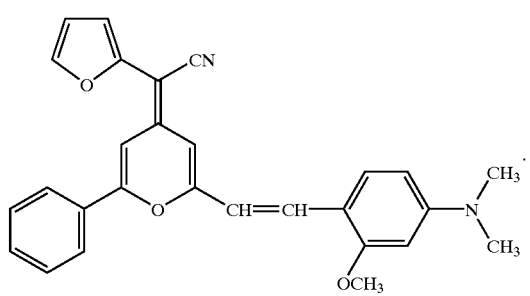
18C
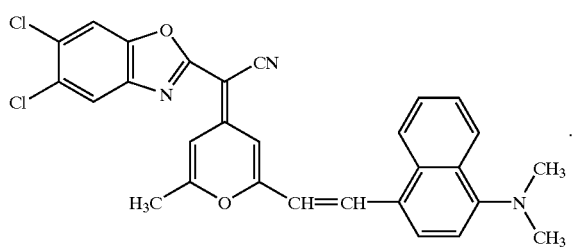
19C
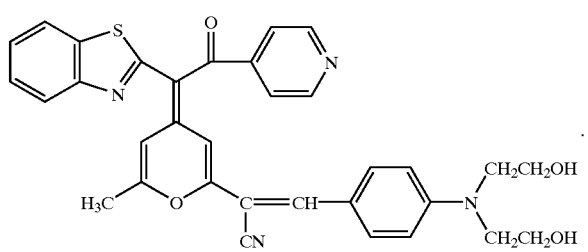

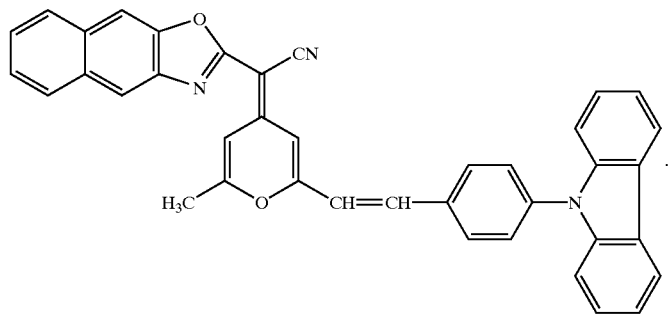

The above-described compounds may be tautomers thereof.

The compound represented by formula (VI) can be synthesized according to various synthesis methods, e.g., the compound can be synthesized with referring to the methods disclosed in JP-A-60-83035 (the term "JP-A" as used herein means an "unexamined published Japanese patent application").

A specific synthesis example of the compound represented by formula (VI) according to the present invention is described below.

SYNTHESIS EXAMPLE

Synthesis of Exemplified Compound 1C

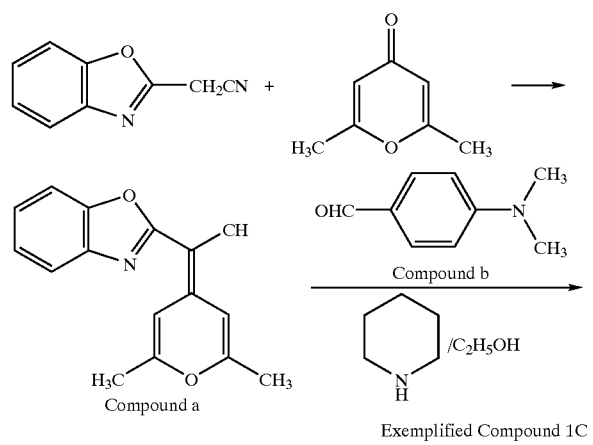

Synthesis of Compound a

Fifteen point seven (15.7) grams (0.126 mol) of 2,6-dimethyl-γ-pyrone and 20.0 g (0.126 mol) of 2-cyanomethylbenzoxazole were dissolved in 100 ml of acetic anhydride followed by reflux with heating for 6 hours. The reaction solution was cooled to room temperature, and extracted with an aqueous solution of ethyl acetate and sodium hydrogenbicarbonate. The organic layer was washed with saturated brine and then dried over magnesium sulfate anhydride. After the solvent was distilled off under reduced pressure, the reaction product was purified through silica gel column chromatography (developing solvent: n-hexane/ethyl acetate in the ratio of 8/2 (vol/vol)), and recrystallized with ethanol, thereby 16.6 g of Compound a was obtained.

Yield: 50%.

Synthesis of Exemplified Compound 1C

Two point six zero (2.60) grams (0.01 mol) of Compound a and 1.50 g (0.01 mol) of Compound b were dissolved in 75 ml of ethanol, and 1.0 ml (0.01 mol) of piperidine was added thereto followed by reflux with heating for 5 hours. The reaction solution was cooled to room temperature, water was added to the solution, and the solid precipitated was filtered. The solid obtained was purified through silica gel column chromatography (developing solvent: chloroform), and recrystallized with ethanol, thereby 1.22 g of Compound 1C was obtained. Yield: 31%. Melting Point: 210–211° C.

The luminescence element according to the present invention comprises a pair of electrodes of the anode and the cathode having formed therebetween a luminescent layer or a plurality of organic compound thin layers including a luminescent layer, and may comprise a positive hole-injecting layer, a positive hole-transporting layer, an electron-injecting layer, an electron-transporting layer, a protecting layer, etc., in addition to a luminescent layer. Each of these layers may have different functions. Various materials can be used to form each layer.

The anode is to supply positive holes to a positive hole-injecting layer, a positive hole-transporting layer, a luminescent layer, etc., and metals, alloys, metal oxides, electrically conductive compounds, or mixtures of these can be used therefor, materials having a work function of 4 eV or more are preferably used. Specific examples of the materials include electrically conductive metal oxides such as a tin oxide, a zinc oxide, an indium oxide, an indium tin oxide (ITO), etc., metals such as gold, silver, chromium, nickel, etc., mixtures or laminations of these metals with electrically conductive metal oxides, inorganic electrically conductive materials such as copper iodide, copper sulfide, etc., organic electrically conductive materials such as polyaniline, polythiophene, polypyrrole, etc., and laminations of these materials with ITO. Electrically conductive metal oxides are preferably used, and ITO is particularly preferably used in view of producibility, high conductivity and transparency. The film thickness of the anode can be selected arbitrarily according to materials used but is hgenerally preferably from 10 nm to 5 μm, more preferably from 50 nm to 1 μm, and still more preferably from 100 to 500 nm.

The anode generally comprises lamination formed on a soda-lime glass, non-alkali glass or transparent resin substrate. When a glass substrate is used, non-alkali glass is preferably used for lessening elution of ions from the glass.

Further, when soda-lime glass is used, it is preferred to provide a barrier coat such as silica. The thickness of the substrate is not particularly limited so long as it can sufficiently stand the physical strength. When glass is used, the thickness is generally 0.2 mm or more, preferably 0.7 mm or more.

Various processes are used in the manufacture of the anode according to the materials to be used. In the case of using ITO, for example, thin layers are formed by an electron beam process, a sputtering process, a resistance heating deposition process, a chemical reaction process (a sol-gel process), or the process of coating the dispersion of an indium tin oxide.

It is possible to reduce the driving voltage or increase the luminescent efficacy of the element by the process such as washing of the anode. In the case of using ITO, for example, UV-ozone processing is effective.

The cathode is to supply electrons to an electron-injecting layer, an electron-transporting layer, a luminescent layer, etc., and the cathode is selected taking into consideration the adhesion with the adjacent electron-injecting layer, electron-transporting layer, luminescent layer, etc., ionization potential and stability. As materials of the cathode, metals, alloys, metal oxides, electrically conductive compounds, or mixtures of these materials can be used. Specific examples include alkali metals (e.g., Li, Na, K) or fluorides of them, alkaline earth metals (e.g., Mg, Ca) or fluorides of them, gold, silver, lead, aluminum, sodium-potassium alloys or mixed metals of them, lithium-aluminum alloys or mixed metals of them, magnesium-silver alloys or mixed metals of them, and rare earth metals such as indium, ytterbium, etc., preferably materials having a work function of 4 eV or less, and more preferably aluminum, lithium-aluminum alloys or mixed metals of them, and magnesium-silver alloys or mixed metals of them. The film thickness of the cathode can be selected arbitrarily according to materials used but is generally preferably from 10 nm to 5 μm, more preferably from 50 nm to 1 μm, and still more preferably from 100 nm to 1 μm.

Processes such as an electron beam process, a sputtering process, a resistance heating deposition process, and a coating process are used in the manufacture of the cathode, and a single metal can be vapor deposited or two or more components can be deposited at the same time. Further, a plurality of metals can be deposited at the same time to form an alloy electrode, alternatively a previously prepared alloy can be deposited.

It is preferred that the sheet resistance of the anode and the cathode be low, preferably several hundred Ω/□ or less.

The luminescent layer may be made of any material so long as, when electric field is impressed, the luminescent layer formed does not prevent positive holes from being injected from the anode, the positive hole-injecting layer and the positive hole-transporting layer, electrons from being injected from the cathode, the electron-injecting layer and the electron-transporting layer, and offers the functions of transferring the electric charge injected and recombining the electrons and positive holes to effect emission. Preferably the luminescent layer contains the methine compound according to the present invention but luminescent materials other than the methine compound according to the present invention can also be used, and as such materials, e.g., benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perynone derivatives, oxadiazole derivatives, aldazine derivatives, pyrralidine derivatives, cyclopentadiene derivatives, bis-styrylanthracene derivatives, quinacridone derivatives, pyrrolopyridine derivatives, thiadiazolopyridine derivatives, cyclopentadiene derivatives, styrylamine derivatives, aromatic dimethylidyne compounds, various metal complexes represented by metal complexes of 8-quinolinol derivatives and rare earth metal complexes, and polymer compounds such as polythiophene, polyphenylene, and polyphenylenevinylene are exemplified. The film thickness of the luminescent layer is not particularly restricted but it is generally preferably from 1 nm to 5 μm, more preferably from 5 nm to 1 μm, and still more preferably from 10 nm to 500 nm.

The luminescent layer can be formed by any process, e.g., a resistance heating deposition process, an electron beam process, a sputtering process, a molecular lamination process, a coating process (a spin coating process, a cast coating process, a dip coating process), or an LB process is used, preferably a resistance heating deposition process and a coating process.

Materials of the positive hole-injecting layer and the positive hole-transporting layer are sufficient if they have any of the functions of injecting positive holes from the anode, transporting positive holes, and barriering off the electrons injected from the cathode. Specific examples of the materials include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, aniline-based copolymers, and electrically conductive high molecular weight oligomers such as tihophene oligomers and polythiophene. The film thickness of the positive hole-injecting layer and the positive hole-transporting layer is not particularly limited but it is generally preferably from 1 nm to 5 μm, more preferably from 5 nm to 1 μm, and still more preferably from 10 nm to 500 nm. The positive hole-injecting layer and the positive hole-transporting layer may be single layer structure comprising one or two or more of the above materials, or may be multilayer structure comprising a plurality of layers of the same composition or different compositions.

The positive hole-injecting layer and the positive hole-transporting layer are formed by a vacuum deposition process, an LB process, or the process of dissolving or dispersing the above-described positive hole-injecting and transporting agent in a solvent and coating (a spin coating process, a cast coating process, a dip coating process). In the case a coating process, a positive hole-injecting and transporting agent can be dissolved or dispersed with a resin component. Examples of such resin components include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, etc.

Materials of the electron-injecting layer and the electron-transporting layer are sufficient if they have any of the functions of injecting electrons from the cathode, transporting electrons, and barriering off the positive holes injected from the anode. Specific examples of the materials include triazole derivatives, oxazole derivatives, oxadiazole derivatives, fluorenone derivatives, anthraquinodimethane derivatives, anthrone derivatives, diphenylquinone derivatives thiopyran dioxide derivatives, carbodiimide derivatives, fluorenylidene methane derivatives, distyrylpyrazine derivatives, heterocyclic tetracarboxylic anhydride such as naphthaleneperylene, phthalocyanine derivatives, and various metal complexes represented by metal complexes such as metal complexes of 8-quinolinol derivatives and metal complexes having a ligand such as metal phthalocyanine, benzoxazole or benzothiazole. The film thickness of the electron-injecting layer and the electron-transporting layer is not particularly restricted but it is generally preferably from 1 nm to 5 μm, more preferably from 5 nm to 1 μm, and still more preferably from 10 nm to 500 nm. The electron-injecting layer and the electron-transporting layer may be single layer structure comprising one or two or more of the above materials, or may be multilayer structure comprising a plurality of layers of the same composition or different compositions.

The electron-injecting layer and the electron-transporting layer are formed by a vacuum deposition process, an LB process, or the process of dissolving or dispersing the above-described electron-injecting and transporting agent in a solvent and coating (a spin coating process, a cast coating process, a dip coating process). In the case a coating process, an electron-injecting and transporting agent can be dissolved or dispersed with a resin component. As the resin components, those exemplified in the positive hole-injecting and transporting layers can be applied.

Materials of the protective layer are sufficient if they have the function of preventing substances which accelerates the deterioration of the element, such as water or oxygen, from entering the element. Specific examples of the materials include metals, e.g., In, Sn, Pb, Au, Cu, Ag, Al, Ti, Ni, etc., metal oxides, e.g., MgO, SiO, $SiO_2$, $Al_2O_3$, GeO, NiO, CaO, BaO, $Fe_2O_3$, $Y_2O_3$, $TiO_2$, etc., metal fluorides, e.g., $MgF_2$, LiF, $AlF_3$, $CaF_2$, etc., polyethylene, polypropylene, polymethyl methacrylate, polyimide, polyurea, polytetrafluoroethylene, polychlorotrifluoroethylene, polydichlorodifluoroethylene, copolymers of chlorotrifluoroethylene and dichlorodifluoroethylene, copolymers obtained by copolymerizing monomer mixtures containing tetrafluoroethylene and at least one comonomer, fluorine-containing copolymers having cyclic structure at the main chain of the copolymer, water-absorbing substances having a water absorption coefficient of 1% or more, and moisture-proof materials having a water absorption coefficient of 0.1% or less.

The forming process of the protective layer is also not particularly restricted and, e.g., a vacuum deposition process, a sputtering process, a reactive sputtering process, an MBE (molecular beam epitaxy) process, a cluster ion beam process, an ion-plating process, a plasma polymerization process (a high frequency exciting ion-plating process), a plasma CVD process, a laser CVD process, a heat CVD process, a gas source CVD process, or a coating process can be applied.

EXAMPLES

The present invention is specifically described below with referring to examples, but the present invention is not limited thereto.

Example 1A

Synthesis of Exemplified Compound A

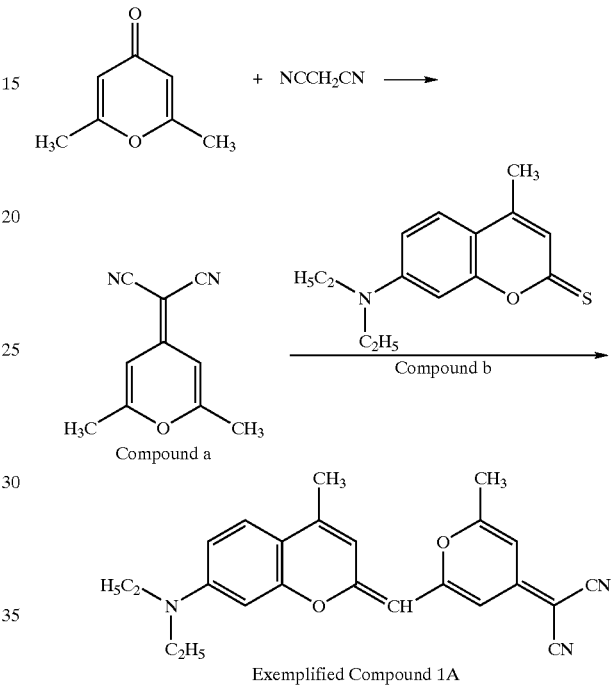

Synthesis of Compound a

One hundred and nineteen (119) grams (0.96 mol) of 2,6-dimethyl-γ-pyron and 70.0 g (1.06 mol) of malononitrile were dissolved in 500 ml of acetic anhydride followed by reflux with heating for 1 hour. The reaction solution was cooled to room temperature, and extracted with ethyl acetate and water. The organic layer was washed with saturated brine and then dried over magnesium sulfate anhydride. The reaction product was purified through silica gel column chromatography (developing solvent: dichloromethane), and recrystallized with ethyl acetate/n-hexane, thereby 92.0 g (0.53 mol) of Compound a was obtained. Yield: 55%.

Synthesis of Exemplified Compound 1A

One point seven two (1.72) grams (0.01 mol) of Compound a and 2.47 g (0.01 mol) of Compound b were dissolved in 10 ml of ethanol, and 1 ml (0.01 mol) of piperidine was added thereto followed by reflux with heating for 4 hours. The reaction solution was cooled to room temperature, then purified through silica gel column chromatography (developing solvent: dichloromethane), and recrystallized with chloroform/ethyl acetate, thereby 1.20 g (3.12 mmol) of exemplified Compound 1A was obtained.

Yield: 31%. Brown crystal: melting point 277° C. or more (decomposed).

Example 2A

Synthesis of Exemplified Compound 24A

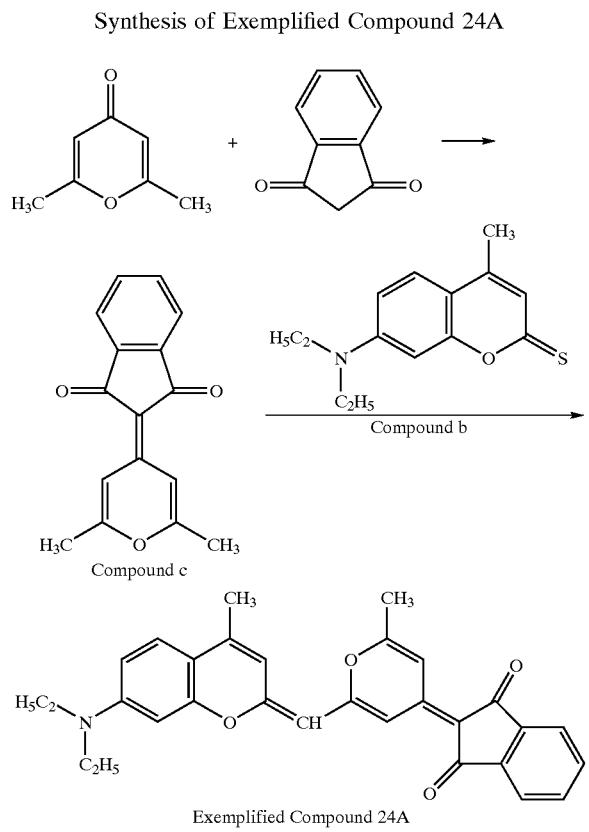

Example 3A

Synthesis of Exemplified Compound 3A

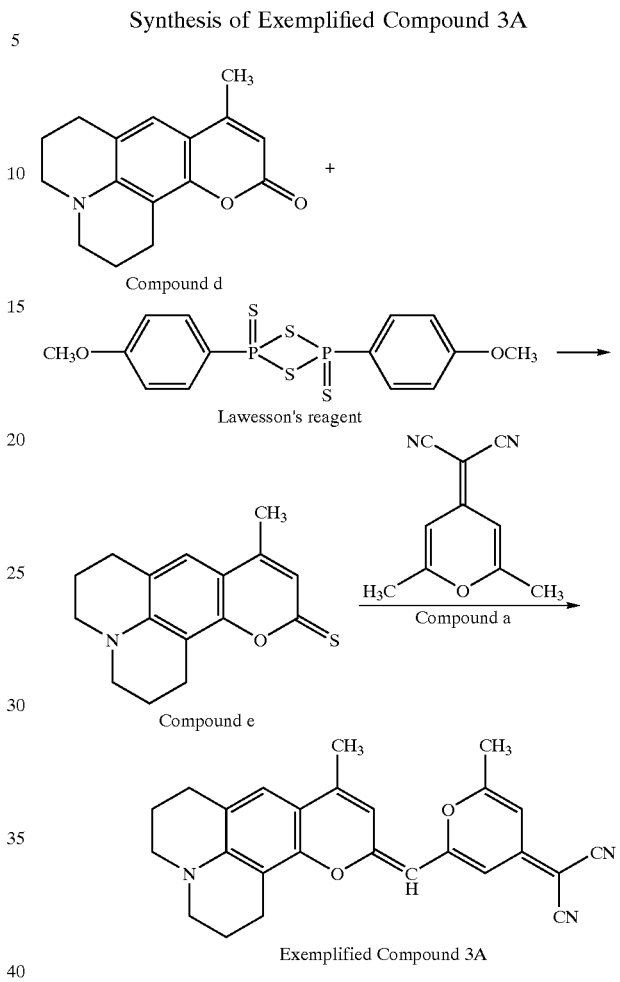

Black green crystal: melting point 238–240° C.

Synthesis of Compound c

Two point five zero (2.50) grams (0.02 mol) of 2,6-dimethyl-γ-pyron and 2.90 g (0.02 mol) of 1,3-indanedione were dissolved in 10 ml of acetic anhydride followed by reflux with heating for 8 hours. The reaction solution was cooled to room temperature, ethanol was added to the solution, and the solid precipitated was filtered out. The solid obtained was recrystallized with ethanol, thereby 3.4 g (0.013 mol) of Compound c was obtained. Yield: 67%.

Synthesis of Exemplified Compound 24A

Two point zero 2 (2.02) grams (8.00 mmol) of Compound c and 1.97 g (8.00 mol) of Compound b were dissolved in 10 ml of ethanol, and 1 ml (0.01 mol) of piperidine was added thereto followed by reflux with heating for 8 hours. The reaction solution was cooled to room temperature, and the solid precipitated was filtered out. The solid obtained was recrystallized with ethanol, thereby 840 ml (1.80 mmol) of exemplified Compound 24A was obtained. Yield: 23%.

Synthesis of Compound e

Twenty-eight point seven (28.7) grams (0.112 mol) of Compound d and 25.0 g (0.55 mol) of Lawesson's reagent were dissolved in 250 ml of toluene followed by reflux with heating for 3 hours. The reaction solution was cooled to room temperature, then purified through silica gel column chromatography (developing solvent: chloroform). The solid obtained was recrystallized with chloroform/n-hexane, thereby 19.2 g (0.070 mmol) of Compound e was obtained. Yield: 62%.

Synthesis of Exemplified Compound 3A

Six point six zero (6.60) grams (0.0383 mol) of Compound a was dissolved in 30 ml of dimethylacetamide, and 4.00 ml (0.040 mol) of piperidine and 8.60 g (0.0317 mol) of Compound e were added thereto while stirring the solution in nitrogen atmosphere. The reaction solution was stirred at outer temperature of 90° C. for 3 hours, then cooled to room temperature, and the reaction solution was poured into water. The solid precipitated was filtered out, purified through silica gel column chromatography (developing solvent: chloroform), and recrystallized with chloroform/n-hexane, thereby 4.23 g (0.010 mol) of exemplified Compound 3A was obtained. Yield: 27%. Brown crystal: melting point 260–263° C. (gradually decomposed).

EXAMPLE 4A

Synthesis of Exemplified Compound 61A

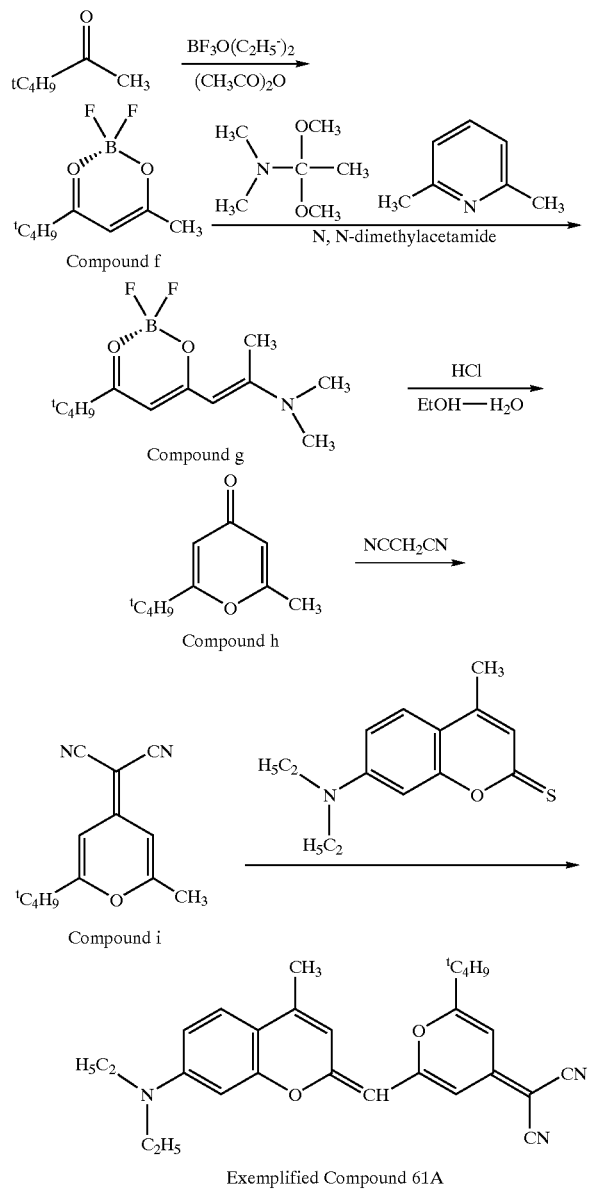

Synthesis of Compound f

One hundred and fifty (150) ml (1.1 mol) of boron trifluoride diethyl ether complex was dropwise added slowly to 100 g (1 mol) of t-butyl methyl ketone and 200 ml of acetic anhydride with maintaining the temperature at 0° C. The system was then stirred at room temperature for 3 hours, then extracted with chloroform and water to concentrate the organic phase. The extract was purified through a silica gel column chromatography to thereby obtain 72 g (yield: 38%) of Compound f.

Synthesis of Compound g

One hundred and eighty-eight (188) grams (1 mol) of Compound f and 178 ml (1 mol) of N,N-dimethylacetamide dimethylacetal were dissolved in 600 ml of N,N-dimethylacetamide, then 120 ml (1 mol) of 2,6-lutidine was added thereto, and the reaction system was stirred at room temperature for 5 hours. Water was added to the reaction solution, the solid precipitated was filtered out and dried, thereby 256 g (yield: 100%) of Compound g was obtained as an orange crystal.

Synthesis of Compound h

Two hundred and eighty (280) grams (1.08 mol) of Compound g was dissolved in 1,200 ml of ethanol and 200 ml of water, and 50 ml of concentrated hydrochloric acid was dropwise added to the solution. The reaction system was then stirred at room temperature for 9 hours, then extracted with ethyl acetate and water to concentrate the organic phase. The extract was purified through a silica gel column chromatography to thereby obtain 170 g (yield: 94%) of Compound h.

Synthesis of Compound i

Nine point eight (9.8) grams (0.59 mol) of Compound h and 4.7 g (0.071 mol) of malononitrile were dissolved in 60 ml of acetic anhydride, the solution was refluxed with heating for 5 hours, then cooled to room temperature, and the reaction solution was poured into water. The solid precipitated was filtered out and purified through silica gel column chromatography, and recrystallized with ethanol/water, thereby 10.8 g (yield: 86%) of Compound i was obtained.

Synthesis of Exemplified Compound 61A

Eight point six zero (8.60) grams (0.040 mol) of Compound i and 9.9 g (0.040 mol) of Compound b were dissolved in 200 ml of ethanol, and 4.00 ml (0.040mol) of piperidine was added thereto while stirring the solution in nitrogen atmosphere. The reaction solution was refluxed with heating for 14 hours, then cooled to room temperature and the reaction solution was concentrated. The solid precipitated was filtered out, purified through silica gel column chromatography (developing solvent: chloroform), and recrystallized with ethanol, thereby 3.08 g (0.0072 mol) of exemplified Compound 61A was obtained. Yield: 18%. Brown crystal: melting point 220–222° C.

Example 5A

Synthesis of Exemplified Compound 63A

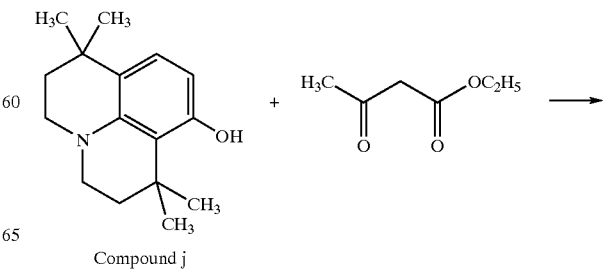

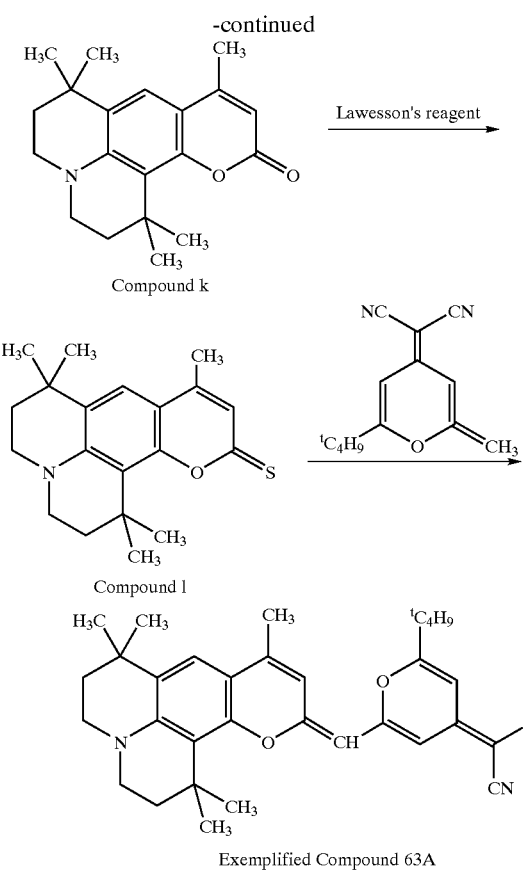

Synthesis of Compound k

Eighty point zero (80.0) grams (0.326 mol) of Compound j synthesized according to the method disclosed in U.S. Pat. No. 4,736,032, 47.0 g (0.361 mol) of ethyl acetate, and 22.1 g (0.162 mol) of zinc chloride were dissolved in 300 ml of ethanol, the solution was refluxed with heating for 16 hours, then cooled to room temperature, and the reaction solution was poured into dilute hydrochloric acid water. The solid precipitated was filtered out after stirring for 3 hours, thereby 83.0 g (0.267 mol) of Compound k was obtained. Yield: 82%.

Synthesis of Compound 1

Sixty-two point three (62.3) grams (0.20 mol) of Compound k and 42.4 g (0.105 mol) of Lawesson's reagent were dissolved in 250 ml of toluene and refluxed with heating for 4 hours. The reaction solution was cooled to room temperature, filtered through celite/activated carbon to concentrate the filtrate. The concentrate was recrystallized with ethanol, thereby 49.0 g (0.150 mol) of Compound 1 was obtained. Yield: 75%.

Synthesis of Exemplified Compound 63A

Seven point four zero (7.40) grams (0.0345 mol) of Compound i and 11.3 g (0.0345 mol) of Compound 1 were dissolved in 300 ml of ethanol, and 7.00 ml (0.080 mol) of piperidine was added thereto while stirring the solution in nitrogen atmosphere. The reaction solution was refluxed with heating for 20 hours, then cooled to room temperature to concentrate the reaction solution. The solid precipitated was filtered out, purified through silica gel column chromatography (developing solvent: chloroform), and recrystallized with ethanol, thereby 4.55 g (0.00896 mol) of exemplified Compound 63A was obtained. Yield: 26%. Brown crystal: melting point 211° C.—(decomposed).

Example 6A

Preparation of Luminescence Element and Evaluation

Example 6A-1

A transparent supporting substrate comprising a glass substrate of a size of 25 mm×25 mm×0.7 mm having coated thereon ITO in a film thickness of 150 nm (manufactured by Tokyo Sanyo Shinku Co., Ltd.) was used. After this transparent supporting substrate was subjected to etching and washing, 40 mg of poly(N-vinylcarbazole), 12 mg of PBD (2-(4-biphenylyl)-5-(4-tert-butylphenyl)-1,3,4-oxadiazole), and 0.5 mg of the compound described in Table 1A below were dissolved in 3 ml of 1,2-dichloroethane and spin-coated on the above-washed ITO substrate. The film thickness of the thus-formed organic thin layer was about 120 nm. A mask which had been subjected to patterning (a mask having a luminescent area of 5 mm×5 mm) was set up on the organic thin layer, and magnesium/silver in the ratio of 10/1 was vapor deposited in a thickness of 50 nm in a vapor deposition apparatus, then silver was deposited in a thickness of 50 nm.

Direct current constant voltage was impressed to the luminescence element to effect emission using source measuring unit model 2400 manufactured by Toyo Technica Co., Ltd., the luminance was measured using luminescent meter BM-8 manufactured by Topcon Co., Ltd., and the luminescent wavelength was measured using spectrum analyzer PMA-11 manufactured by Hamamatsu Photonics Co., Ltd. The results obtained are shown in Table 1A below.

TABLE 1A

| Element No. | Compound | Minimum Driving Voltage (V) | Maximum Luminance (cd/m²) | Luminescent Wavelength λmax (nm) | CIE Chromaticity Coordinates (x, y) | Remarks |
|---|---|---|---|---|---|---|
| 101A | Comparative Compound a | 14 | 80 | 596 | (0.50, 0.50) | Comparison |
| 102A | Comparative Compound b | 17 | 32 | 602 | (0.59, 0.40) | Comparison |
| 103A | Exemplified Compound 1A | 8 | 720 | 628 | (0.67, 0.32) | Invention |
| 104A | Exemplified Compound 3A | 8 | 580 | 642 | (0.68, 0.32) | Invention |

TABLE 1A-continued

| Element No. | Compound | Minimum Driving Voltage (V) | Maximum Luminance (cd/m$^2$) | Luminescent Wavelength λmax (nm) | CIE Chromaticity Coordinates (x, y) | Remarks |
|---|---|---|---|---|---|---|
| 105A | Exemplified Compound 14A | 9 | 420 | 603 | (0.63, 0.35) | Invention |
| 106A | Exemplified Compound 24A | 8 | 615 | 615 | (0.65, 0.34) | Invention |
| 107A | Exemplified Compound 25A | 8 | 563 | 633 | (0.66, 0.33) | Invention |
| 108A | Exemplified Compound 61A | 7 | 1,240 | 623 | (0.66, 0.33) | Invention |
| 109A | Exemplified Compound 63A | 7 | 1,070 | 644 | (0.68, 0.31) | Invention |

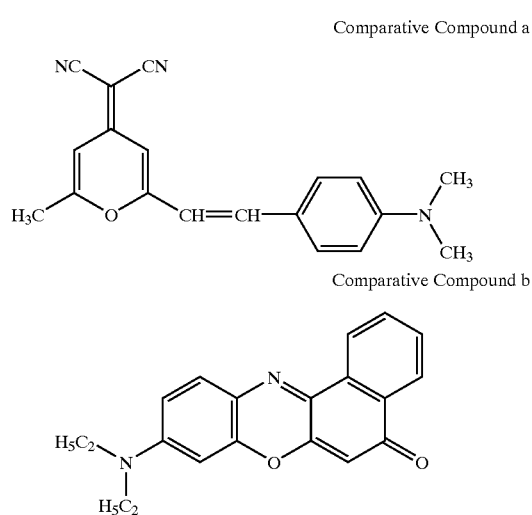

Comparative Compound a

Comparative Compound b

As is apparent from the results in Table 1A, the element in which the compound according to the present invention was used could exhibit high luminance emission with low driving voltage as compared with the element using the comparative compound even in a coating process where luminance is generally low and also showed red color luminescence with high color purity.

Example 6A-2

After ITO substrate was subjected to etching and washing in the same manner as in Example 6A-1, about 40 nm of TPD (N,N'-bis(3-methylphenyl)-N,N'-diphenylbenzidine), about 20 nm of the compound shown in Table 2A below, and about 40 nm of 2,5-bis(1-naphthyl)-1,3,4-oxadiazole were vapor deposited in order in vacuo of $10^{-5}$ to $10^{-6}$ Torr under the substrate temperature condition of room temperature. Subsequently, deposition of the cathode was performed in the same manner as in Example 6A-1 and evaluation was carried out. The results obtained are shown in Table 2A below.

TABLE 2A

| Element No. | Compound | Minimum Driving Voltage (V) | Maximum Luminance (cd/m$^2$) | Luminescent Wavelength λmax (nm) | CIE Chromaticity Coordinates (x, y) | Remarks |
|---|---|---|---|---|---|---|
| 201A | Comparative Compound a | 7 | 270 | 605 | (0.52, 0.48) | Comparison |
| 202A | Comparative Compound b | 8 | 160 | 620 | (0.60, 0.38) | Comparison |
| 203A | Exemplified Compound 1A | 3 | 1,210 | 635 | (0.67, 0.32) | Invention |
| 204A | Exemplified Compound 24A | 4 | 980 | 624 | (0.66, 0.34) | Invention |
| 205A | Exemplified Compound 61A | 3 | 3,080 | 629 | (0.66, 0.34) | Invention |
| 206A | Exemplified Compound 63A | 3 | 2,700 | 649 | (0.68, 0.31) | Invention |

Comparative Compounds a and b Were the Same as Used in Example 6A-1

As is apparent from the results in Table 2A, the element in which the compound according to the present invention was used could exhibit high luminance emission also in a vapor deposition process as compared with the element using the comparative compound and also showed red color luminescence with high color purity.

Example 6A-3

After ITO substrate was subjected to etching and washing in the same manner as in Example 6A-1, TPD was vapor deposited in a thickness of about 40 nm, and then the compound shown in Table 3A below and Alq(tris (8-hydroxyquinolinate)aluminum) were vapor deposited at depositing rate of 0.04 Å/sec and 4 Å/sec, respectively, in a film thickness of about 60 nm. Subsequently, deposition of the cathode was performed in the same manner as in Example 6A-1 and evaluation was carried out. The results obtained are shown in Table 3A below.

TABLE 3A

| Element No. | Compound | Maximum Luminance (cd/m$^2$) | Luminescent Wavelength λmax (nm) | CIE Chromaticity Coordinates (x, y) | Remarks |
| --- | --- | --- | --- | --- | --- |
| 301A | Comparative Compound a | 420 | 598 | (0.51, 0.48) | Comparison |
| 302A | Comparative Compound b | 370 | 610 | (0.60, 0.39) | Comparison |
| 303A | Exemplified Compound 1A | 2,230 | 632 | (0.67, 0.33) | Invention |
| 304A | Exemplified Compound 24A | 1,980 | 618 | (0.65, 0.34) | Invention |
| 305A | Exemplified Compound 61A | 5,800 | 627 | (0.66, 0.34) | Invention |
| 306A | Exemplified Compound 63A | 4,360 | 646 | (0.67, 0.31) | Invention |

Comparative Compounds a and b Were the Same as Used in Example 6A-1

As is apparent from the results in Table 3A, the element in which the compound according to the present invention was used could exhibit high luminance emission also with the doped system in a vapor deposition process as compared with the element using the comparative compound and also showed red color luminescence with high color purity.

Example 6A-4

After ITO substrate was subjected to etching and washing in the same manner as in Example 6A-1, TPD was vapor deposited in a thickness of about 40 nm, and then the exemplified compound 1A was deposited in a thickness of about 60 nm. Subsequently, deposition of the cathode was performed in the same manner as in Example 6A-1.

As a result of evaluation of the prepared element, it exhibited luminance of 101 cd/m$^2$ at 10 V, and red color luminescence with high color purity having λmax=636 nm and CIE chromaticity (x, y)=(0.68, 0.31) was observed, which shows that the compound according to the present invention is effective as an electron-injecting and transporting agent and also as a luminescent agent.

Example 6A-5

The solution obtained by dissolving 40 mg of poly(N-vinylcarbazole), 12 mg of 2,5-bis(1-naphthyl)-1,3,4-oxadiazole, 10 mg of tetraphenylbutadiene, 0.5 mg of DCM, and 0.1 mg of the exemplified compound 2A of the present invention in 3 ml of 1,2-dichloroethane was spin-coated on the ITO glass substrate which had been subjected to etching and washing in the same manner as in Example 6A-1. Subsequently, deposition of the cathode was performed in the same manner as in Example 6A-1.

Direct current voltage was impressed to this element and luminescent characteristics were measured with making the ITO electrode the anode and the Mg/Ag electrode the cathode. White luminescence (luminance of 1,420 cd/m$^2$) on CIE chromaticity diagram (x, y)=(0.34, 0.36) was obtained at 12 V, which showed the compound according to the present invention was effective for white luminescence.

The present invention can provide a novel methine compound which makes it possible to obtain red luminescence with high color purity as compared with conventionally used compounds. In particular, due to the compound of the present invention excellent luminescence characteristics can be obtained even in a coating process where luminance is generally low, therefore, a luminescence element can be produced advantageously from the viewpoint of the production cost. Further, as the compound of the present invention can function as a luminescent material and electron-injecting-transporting agent in one, a luminescence element can be produced easily.

Example 1B

A transparent supporting substrate comprising a glass substrate of a size of 25 mm×25 mm×0.7 mm having coated thereon ITO in a film thickness of 150 nm (manufactured by Tokyo Sanyo Shinku Co., Ltd.) was used. After this transparent supporting substrate was subjected to etching and washing, 40 mg of poly(N-vinylcarbazole), 12 mg of PBD (2-(4-biphenylyl)-5-(4-tert-butylphenyl)-1,3,4-oxadiazole), and 0.5 mg of the compound described in Table 1B below were dissolved in 3 ml of 1,2-dichloroethane and spin-coated on the above-washed ITO substrate. The film thickness of the thus-formed organic thin layer was about 120 nm. A mask which had been subjected to patterning (a mask having a luminescent area of 5 mm×5 mm) was setup on the organic thin layer, and magnesium/silver in the ratio of 10/1 was vapor deposited in a thickness of 50 nm in a vapor deposition apparatus, then silver was deposited in a thickness of 50 nm.

Direct current constant voltage was impressed to the luminescence element to effect emission using source measuring unit model 2400 manufactured by Toyo Technica Co., Ltd., the luminance was measured using luminescent meter BM-8 manufactured by Topcon Co., Ltd., and the luminescent wavelength was measured using spectrum analyzer PMA-11 manufactured by Hamamatsu Photonics Co., Ltd.

The results obtained are shown in Table 1B below.

TABLE 1B

| Element No | Compound | Minimum Driving Voltage (V) | Maximum Luminance (cd/m$^2$) | Luminescent Wavelength λmax (nm) | CIE Chromaticity Coordinates (x, y) | Remarks |
|---|---|---|---|---|---|---|
| 101B | Comparative Compound a | 14 | 80 | 596 | (0.50, 0.50) | Comparison |
| 102B | Exemplified Compound 1B | 9 | 780 | 615 | (0.64, 0.37) | Invention |
| 103B | Exemplified Compound 2B | 8 | 720 | 633 | (0.67, 0.32) | Invention |
| 104B | Exemplified Compound 4B | 8 | 530 | 651 | (0.68, 0.32) | Invention |
| 105B | Exemplified Compound 12B | 9 | 615 | 612 | (0.64, 0.38) | Invention |
| 106B | Exemplified Compound 13B | 8 | 620 | 630 | (0.66, 0.33) | Invention |

Comparative Compound a

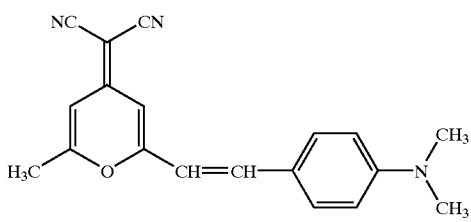

As is apparent from the results in Table 1B, the element in which the compound according to the present invention was used could exhibit high luminance emission with low driving voltage as compared with the element using the comparative compound even in a coating process where luminance is generally low and also showed red color luminescence with high color purity.

Example 2B

After ITO substrate was subjected to etching and washing in the same manner as in Example 1B, about 40 nm of TPD (N,N'-bis(3-methylphenyl)-N,N'-diphenylbenzidine), about 20 nm of the compound shown in Table 2B below, and about 40 nm of 2,5-bis(1-naphthyl)-1,3,4-oxadiazole were vapor deposited in order in vacuo of $10^{-5}$ to $10^{-6}$ Torr under the substrate temperature condition of room temperature. Subsequently, deposition of the cathode was performed in the same manner as in Example 1B and evaluation was carried out. The results obtained are shown in Table 2B below.

TABLE 2B

| Element No. | Compound | Minimum Driving Voltage (V) | Maximum Luminance (cd/m$^2$) | Luminescent Wavelength λmax (nm) | CIE Chromaticity Coordinates (x, y) | Remarks |
|---|---|---|---|---|---|---|
| 201B | Comparative Compound a | 7 | 270 | 605 | (0.52, 0.48) | Comparison |
| 202B | Exemplified Compound 1B | 3 | 1,380 | 624 | (0.65, 0.36) | Invention |
| 203B | Exemplified Compound 2B | 3 | 1,050 | 642 | (0.67, 0.32) | Invention |
| 204B | Exemplified Compound 8B | 4 | 1,120 | 624 | (0.66, 0.35) | Invention |

As is apparent from the results in Table 2B, the element in which the compound according to the present invention was used could exhibit high luminance emission also in a vapor deposition process as compared with the element using the comparative compound and also showed red color luminescence with high color purity.

Example 3B

After ITO substrate was subjected to etching and washing in the same manner as in Example 1B, TPD was vapor deposited in a thickness of about 40 nm, and then the compound shown in Table 3B below and Alq(tris (8-hydroxyquinolinate)aluminum) were vapor deposited at depositing rate of 0.04 Å/sec and 4 Å/sec, respectively, in a film thickness of about 60 nm. Subsequently, deposition of the cathode was performed in the same manner as in Example 1B and evaluation was carried out. The results obtained are shown in Table 3B below.

TABLE 3B

| Element No | Compound | Maximum Luminance (cd/m$^2$) | Luminescent Wavelength λmax (nm) | CIE Chromaticity Coordinates (x, y) | Remarks |
|---|---|---|---|---|---|
| 301B | Comparative Compound a | 420 | 598 | (0.51, 0.48) | Comparison |
| 302B | Exemplified Compound 1B | 1,980 | 616 | (0.66, 0.34) | Invention |
| 303B | Exemplified Compound 2B | 1,560 | 634 | (0.67, 0.32) | Invention |
| 304B | Exemplified Compound 8B | 710 | 672 | (0.66, 0.29) | Invention |
| 305B | Exemplified Compound 21B | 1,100 | 608 | (0.65, 0.35) | Invention |
| 306B | Exemplified Compound 22B | 1,548 | 663 | (0.69, 0.31) | Invention |
| 307B | Exemplified Compound 23B | 3,990 | 634 | (0.61, 0.37) | Invention |
| 308B | Exemplified Compound 24B | 600 | 709 | (0.67, 0.29) | Invention |
| 309B | Exemplified Compound 25B | 2,660 | 633 | (0.61, 0.37) | Invention |
| 310B | Exemplified Compound 26B | 1,200 | 634 | (0.61, 0.37) | Invention |
| 311B | Exemplified Compound 27B | 4,070 | 605 | (0.57, 0.51) | Invention |
| 312B | Exemplified Compound 29B | 910 | 640 | (0.58, 0.41) | Invention |
| 313B | Exemplified Compound 34B | 1,510 | 935 | (0.60, 0.37) | Invention |

Comparative Compound a was the same as used in Example 1B.

As is apparent from the results in Table 3B, the element in which the compound according to the present invention was used could exhibit high luminance emission also with the doped system in a vapor deposition process as compared with the element using the comparative compound and also showed red color luminescence with high color purity.

Example 4B

After ITO substrate was subjected to etching and washing in the same manner as in Example 1B, TPD was vapor deposited in a thickness of about 40 nm, and then the compound shown in Table 4B below was deposited in a thickness of about 60 nm. Subsequently, deposition of the cathode was performed in the same manner as in Example 1B. The results of evaluation are shown in Table 4B below.

TABLE 4B

| Element No | Compound | Minimum Driving Voltage (V) | Maximum Luminance (cd/m$^2$) | Luminescent Wavelength λmax (nm) | CIE Chromaticity Coordinates (x, y) | Remarks |
|---|---|---|---|---|---|---|
| 401B | Exemplified Compound 1 | 11 | 110 | 630 | (0.66, 0.33) | Invention |
| 402B | Exemplified Compound 22B | 11 | 120 | 630 | (0.66, 0.33) | Invention |
| 403B | Exemplified Compound 25B | 9 | 90 | 642 | (0.67, 0.32) | Invention |
| 404B | Exemplified Compound 27B | 9 | 70 | 676 | (0.62, 0.37) | Invention |
| 405B | Exemplified Compound 34B | 10 | 80 | 651 | (0.88, 0.31) | Invention |

As is apparent from the results in Table 4B, red color luminescence with high color purity is observed, which shows that the compound according to the present invention is effective as an electron-injecting and transporting agent and also as a luminescent agent.

Example 5B

The solution obtained by dissolving 40 mg of poly(N-vinylcarbazole), 12 mg of 2,5-bis(1-naphthyl)-1,3,4- oxadiazole, 10 mg of tetraphenylbutadiene, 0.5 mg of DCM, and 0.1 mg of the compound shown in Table 5B below in 3 ml of 1,2-dichloroethane was spin-coated on the ITO glass substrate which had been subjected to etching and washing in the same manner as in Example 1B. Subsequently, deposition of the cathode was performed in the same manner as in Example 1B. Direct current voltage was impressed to this element with making the ITO electrode the anode and the Mg/Ag electrode the cathode and evaluation was carried out. The results obtained are shown in Table 5B below.

TABLE 5B

| Element No. | Compound | Minimum Driving Voltage (V) | Maximum Luminance (cd/m²) | CIE Chromaticity Coordinates (x, y) | Remarks |
|---|---|---|---|---|---|
| 501B | Exemplified Compound 1B | 15 | 1,370 | (0.34, 0.37) | Invention |
| 502B | Exemplified Compound 22B | 15 | 2,100 | (0.33, 0.35) | Invention |
| 503B | Exemplified Compound 25B | 14 | 1,280 | (0.36, 0.34) | Invention |
| 504B | Exemplified Compound 34B | 15 | 1,850 | (0.35, 0.35) | Invention |

As is apparent from the results in Table 5B, it was found that the compound according to the present invention was effective for white luminescence.

The present invention can provide a novel methine compound which makes it possible to obtain red luminescence with high color purity as compared with conventionally used compounds. In particular, due to the compound of the present invention excellent luminescence characteristics can be obtained even in a coating process where luminance is generally low, therefore, a luminescence element can be produced advantageously from the viewpoint of the production cost. Further, as the compound of the present invention can function as a luminescent material and electron-injecting-transporting agent in one, a luminescence element can be produced easily.

washing, 40 mg of poly(N-vinylcarbazole), 12 mg of PBD (2-(4-biphenylyl)-5-(4-tert-butylphenyl)-1,3,4-oxadiazole), and 0.5 mg of the compound described in Table 1C below were dissolved in 3 ml of 1,2-dichloroethane and spin-coated on the above-washed ITO substrate. The film thickness of the thus-formed organic thin layer was about 120 nm. A mask which had been subjected to patterning (a mask having a luminescent area of 5 mm×5 mm) was set up on the organic thin layer, and magnesium/silver in the ratio of 10/1 was vapor deposited in a thickness of 50 nm in a vapor deposition apparatus, then silver was deposited in a thickness of 50 nm.

Direct current constant voltage was impressed to the luminescence element to effect emission using source measuring unit model 2400 manufactured by Toyo Technica Co., Ltd., the luminance was measured using luminescent meter BM-8 manufactured by Topcon Co., Ltd., and the luminescent wavelength was measured using spectrum analyzer PMA-11 manufactured by Hamamatsu Photonics Co., Ltd. The results obtained are shown in Table 1C below.

Comparative Compound a

TABLE 1C

| Element No. | Compound | Minimum Driving Voltage (V) | Maximum Luminance (cd/m²) | Luminescent Wavelength λmax (nm) | CIE Chromaticity Coordinates (x, y) | Remarks |
|---|---|---|---|---|---|---|
| 101C | Comparative Compound a | 14 | 80 | 596 | (0.50, 0.50) | Comparison |
| 102C | Exemplified Compound 1C | 8 | 760 | 609 | (0.64, 0.37) | Invention |
| 103C | Exemplified Compound 2C | 9 | 700 | 623 | (0.67, 0.36) | Invention |
| 104C | Exemplified Compound 3C | 9 | 582 | 618 | (0.68, 0.38) | Invention |
| 105C | Exemplified Compound 8C | 9 | 624 | 606 | (0.65, 0.38) | Invention |
| 106C | Exemplified Compound 9C | 8 | 750 | 612 | (0.64, 0.36) | Invention |

Example 1C

A transparent supporting substrate comprising a glass substrate of a size of 25 mm×25 mm×0.7 mm having coated thereon ITO in a film thickness of 150 nm (manufactured by Tokyo Sanyo Shinku Co., Ltd.) was used. After this transparent supporting substrate was subjected to etching and

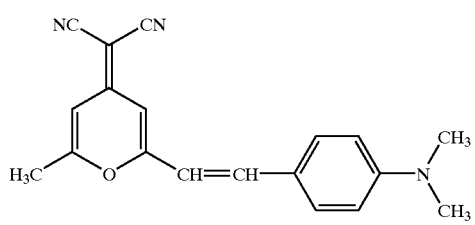

As is apparent from the results in Table 1C, the element in which the compound according to the present invention was used could exhibit high luminance emission with low driving voltage as compared with the element using the comparative compound even in a coating process where luminance is generally low and also showed red color luminescence with high color purity.

Example 2C

After ITO substrate was subjected to etching and washing in the same manner as in Example 1C, about 40 nm of TPD (N,N'-bis(3-methylphenyl)-N,N'-diphenylbenzidine), about 20 nm of the compound shown in Table 2C, and about 40 nm of 2,5-bis(1-naphthyl)-1,3,4-oxadiazole were vapor deposited in order in vacuo of $10^{-5}$ to $10^{-6}$ Torr under the substrate temperature condition of room temperature. Subsequently, deposition of the cathode was performed in the same manner as in Example 1C and evaluation was carried out. The results obtained are shown in Table 2C.

Comparative Compound a Was the Same as Used in Example 1C.

As is apparent from the results in Table 2C, the element in which the compound according to the present invention was used could exhibit high luminance emission also in a vapor deposition process as compared with the element using the comparative compound and also showed red color luminescence with high color purity.

Example 3C

After ITO substrate was subjected to etching and washing in the same manner as in Example 1C, TPD was vapor deposited in a thickness of about 40 nm, and then the compound shown in Table 3C and Alq (tris(8-hydroxyquinolinate)aluminum) were vapor deposited at depositing rate of 0.04 Å/sec and 4 Å/sec, respectively, in a film thickness of about 60 nm. Subsequently, deposition of the cathode was performed in the same manner as in Example 1C and evaluation was carried out. The results obtained are shown in Table 3C.

TABLE 2C

| Element No. | Compound | Minimum Driving Voltage (V) | Maximum Luminance (cd/m$^2$) | Luminescent Wavelength λmax (nm) | CIE Chromaticity Coordinates (x, y) | Remarks |
|---|---|---|---|---|---|---|
| 201C | Comparative Compound a | 7 | 270 | 605 | (0.52, 0.48) | Comparison |
| 202C | Exemplified Compound 1C | 3 | 1,365 | 625 | (0.67, 0.34) | Invention |
| 203C | Exemplified Compound 2C | 4 | 1,150 | 638 | (0.67, 0.35) | Invention |
| 204C | Exemplified Compound 8C | 4 | 1,080 | 633 | (0.68, 0.33) | Invention |

TABLE 3C

| Element No. | Compound | Maximum Luminance (cd/m$^2$) | Luminescent Wavelength λmax (nm) | CIE Chromaticity Coordinates (x, y) | Remarks |
|---|---|---|---|---|---|
| 301C | Comparative Compound a | 420 | 598 | (0.51, 0.48) | Comparison |
| 302C | Exemplified Compound 1C | 1,870 | 615 | (0.65, 0.35) | Invention |
| 303C | Exemplified Compound 2C | 1,640 | 626 | (0.68, 0.35) | Invention |
| 304C | Exemplified Compound 3C | 1,328 | 621 | (0.68, 0.36) | Invention |

Comparative Compound a Was the Same as Used in Example 1C.

As is apparent from the results in Table 3C, the element in which the compound according to the present invention was used could exhibit high luminance emission also with the doped system in a vapor deposition process as compared with the element using the comparative compound and also showed red color luminescence with high color purity.

After ITO substrate was subjected to etching and washing in the same manner as in Example 1C, TPD was vapor deposited in a thickness of about 40 nm, and then the exemplified compound 1C was deposited in a thickness of about 60 nm. Subsequently, deposition of the cathode was performed in the same manner as in Example 1C.

As a result of evaluation of the prepared element, it exhibited luminance of 130 cd/m$^2$ at 12 V, and red color luminescence with high color purity having $\lambda$max=611 nm and CIE chromaticity (x, y)=(0.65, 0.32) was observed, which shows that the compound according to the present invention is effective as an electron-injecting and transporting agent and also as a luminescent agent.

Example 5C

The solution obtained by dissolving 40 mg of poly(N-vinylcarbazole), 12 mg of 2,5-bis(1-naphthyl)-1,3,4-oxadiazole, 10 mg of tetraphenylbutadiene, 0.5 mg of DCM, and 0.1 mg of the exemplified compound 2C of the present invention in 3 ml of 1,2-dichloroethane was spin-coated on the ITO glass substrate which had been subjected to etching and washing in the same manner as in Example 1C. Subsequently, deposition of the cathode was performed in the same manner as in Example 1C.

Direct current voltage was impressed to this element and luminescent characteristics were measured with making the ITO electrode the anode and the Mg/Ag electrode the cathode. White luminescence (luminance of 1,405 cd/m$^2$) on CIE chromaticity diagram (x, y)=(0.35, 0.37) was obtained at 14 V, which showed the compound according to the present invention was effective for white luminescence.

The present invention can provide a novel methine compound which makes it possible to obtain red EL luminescence with high color purity as compared with conventionally used compounds. In particular, due to the compound of the present invention excellent luminescence characteristics can be obtained even in a coating process where luminance is generally low, therefore, a luminescence element can be produced advantageously from the viewpoint of the production cost. Further, as the compound of the present invention can function as a luminescent material and electron-injecting-transporting agent in one, a luminescence element can be produced easily.

What is claimed is:

1. An organic luminescence element comprising a pair of electrodes having therebetween at least one organic compound thin layer including a luminescent layer, wherein at least one organic compound thin layer is a layer comprising a methine compound represented by formula (VI):

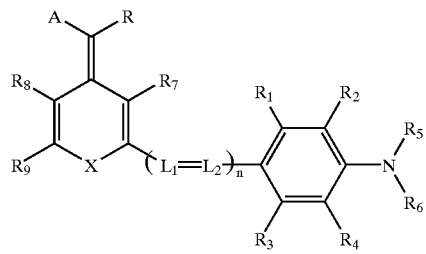

(VI)

wherein $R_1$, $R_2$, $R_3$, $R_4$, $R_5$, $R_6$, $R_7$, $R_8$, $R_9$ and R each represents a hydrogen atom or a substituent; A represents a heterocyclic ring containing an aromatic ring; X represents an oxygen atom, a sulfur atom, or N—$R_{10}$, wherein $R_{10}$ represents a hydrogen atom or a substituent; $L_1$ and $L_2$ each represents a substituted or unsubstituted methine group; and n represent 1 or 2.

2. The organic luminescence element of claim 1, wherein at least one organic compound thin layer is a layer further comprising a polymer.

3. The organic luminescence element of claim 1, wherein at least one organic compound thin layer is a layer in which the methine compound represented by formula (VI) is dispersed in a polymer.

4. The organic luminescence element of claim 1, wherein $R_9$ represents a hydrogen atom, a substituted or unsubstituted alkyl group, a substituted or unsubstituted aryl group, a ring formed by linking with $R_8$, or

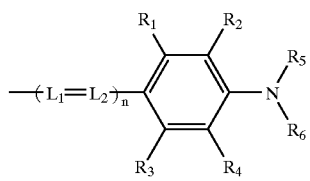

(wherein $R_1$, $R_2$, $R_3$, $R_4$, $R_5$, $R_6$, $L_1$, $L_2$, and n each has the same meaning as in formula (VI).

5. The organic luminescence element of claim 4, wherein $R_9$ represents a hydrogen atom, a substituted or unsubstituted alkyl group, a substituted or unsubstituted aryl group, or a ring formed by linking with $R_8$.

6. The organic luminescence element of claim 1, wherein A represents furyl, pyrrolyl, imidazolyl, pyrazolyl, pyridyl, pyrazinyl, pyrimidinyl pyridazinyl, indolyl, isoindolyl, indolizinyl, phenoxazinyl, xanthenyl, indazolyl, purinyl, quinolyl, isoquinolyl, phthalazinyl, naphthyridinyl, quinoxalinyl, quinazolinyl, cinnolinyl pteridinyl, carbazolyl, carbolinyl, phenanthridinyl, acridinyl, phenanthrinyl, phenazinyl, isothiazolyl, isooxazolyl, phenothiazinyl, furazanyl, oxazolyl, benzoxazolyl, thiazolyl, beuzothiazolyl, selenazolyl, benzoselenazolyl, oxadiazolyl, thiadiazolyl, triazolyl, benzotriazolyl, tetrazolyl, tetraazaindenyl, or indolenyl.

7. The organic luminescence element of claim 6, wherein A represents imidazolyl, pyridyl, pyrazinyl, pyrimidinyl, pyridazinyl, quinolyl, isoquinolyl, phthalazinyl, naphthyridinyl, quinoxalinyl, quinazolinyl, cinnolinyl, pteridinyl, xazolyl, benzoxazolyl, thiazolyl, benzothiazolyl, oxadiazolyl, or thiadiazolyl.

8. The organic luminescence element of claim 1, wherein $L_1$ and $L_2$ each represents an unsubstituted methine group, an alkyl-substituted methine group, or an alkoxyl-substituted methine group.

9. The organic luminescence element of claim 1, wherein R represents an electron-attractive group.

10. The organic luminescence element of claim 1, wherein R represents a cyano group, a carbonyl group, a thiocarbonyl group, an aryl group an aromatic heterocyclic group, a sulfonyl group, a carbamoyl group, or a sulfamoyl group.

11. The organic luminescence element of claim 1, wherein R represents a cyano group, a carbonyl group, a sulfonyl group, or an aromatic heterocyclic group.

* * * * *

UNITED STATES PATENT AND TRADEMARK OFFICE
CERTIFICATE OF CORRECTION

PATENT NO. : 6,835,474 B2
DATED : December 28, 2004
INVENTOR(S) : Okada et al.

It is certified that error appears in the above-identified patent and that said Letters Patent is hereby corrected as shown below:

<u>Title page</u>,
Item [*] Notice, should read
-- [*] Notice:     Subject to any disclaimer, the term of this patent is extended or adjusted under 35 U.S.C. 154(b) by 75 days. --

Signed and Sealed this

Seventeenth Day of May, 2005

JON W. DUDAS
*Director of the United States Patent and Trademark Office*